United States Patent [19]
Chucholowski et al.

[11] Patent Number: 5,830,920
[45] Date of Patent: Nov. 3, 1998

[54] SULFURIC ACID ESTERS OF SUGAR ALCOHOLS

[75] Inventors: Alexander Chucholowski, Grenzach-Wyhlen; Jürgen Fingerle, Rheinfelden, both of Germany; Niggi Iberg, Basel, Switzerland; Hans Peter Märki, Basel, Switzerland; Rita Müller, Basel, Switzerland; Michael Pech, Hartheim, Germany; Marianne Rouge, Basel, Switzerland; Gérard Schmid, Kienberg, Switzerland; Thomas Tschopp, Ettingen, Switzerland; Hans Peter Wessel, Heitersheim, Germany

[73] Assignee: Hoffmann-La Roche Inc., Nutley, N.J.

[21] Appl. No.: 639,986

[22] Filed: Apr. 26, 1996

[30] Foreign Application Priority Data

May 5, 1995 [CH] Switzerland ............... 1310/95

[51] Int. Cl.$^6$ ................... A61K 31/045; C07C 205/00
[52] U.S. Cl. ............... 514/730; 514/25; 514/724; 536/4.1; 536/120; 568/705; 568/715; 568/808; 568/809
[58] Field of Search ................ 536/4.1, 120, 22.1; 574/25, 738, 739; 514/42, 599, 730, 724, 613, 616; 568/705, 715, 809, 808

[56] References Cited

U.S. PATENT DOCUMENTS 4,438,260 3/1984 Peterson ................... 536/13.9

(List continued on next page.)

FOREIGN PATENT DOCUMENTS 56575 1/1982 European Pat. Off. .

(List continued on next page.)

OTHER PUBLICATIONS

Bioorg. Med. Chem. Lett. 4, pp. 1419–1422 (1994).

(List continued on next page.)

*Primary Examiner*—Elli Peselev
*Attorney, Agent, or Firm*—George W. Johnston; Patricia S. Rocha-Tramaloni

[57] ABSTRACT

Compounds of the formula

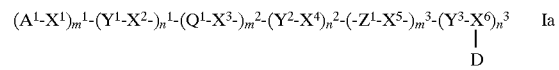
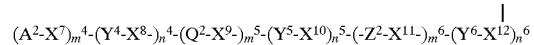
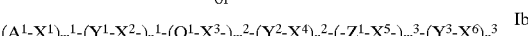
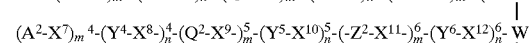
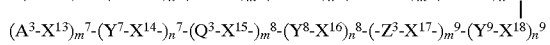

wherein
 $n^1-n^9$ are each independently 0 or 1;
 $m^1-m^9$ are each independently 0 or 1, but with the proviso that at least one of $m^1$, $m^2$ and $m^3$, at least one of $m^4$, $m^5$ and $m^6$ and, when present, at least one of $m^7$, $m^8$ and $m^9$ is 1; and wherein
 $X^1-X^{18}$ each independently is —O—, —CONR$^1$,— NR$^1$CO— or —NR$^1$—;
 $R^1$ is hydrogen or lower alkyl;
 W is a benzene or s-triazine;
 $Y^1-Y^9$ each independently is an aromatic ring systems;
 $A^1-A^3$ each independently is a residue of a sugar alcohol devoid of the 1-hydroxy group or a derivative thereof, a residue of a sugar acid devoid of the 1-carboxy group or a derivative thereof or tris-(hydroxymethyl)-methyl;
 D is the di-residue of a sugar alcohol devoid of 2 hydroxy groups or a derivative thereof or the di-residue of a sugar dicarboxylic acid devoid of 2 carboxy group or a derivative thereof;
 $Q^1-Q^3$ and $Z^1-Z3$ each independently are the di-residue of a sugar alcohol devoid of 2 hydroxy groups or a derivative thereof or the di-residue of a sugar dicarboxylic acid devoid of 2 carboxy groups or a derivative thereof or didesoxyglycopyranoside or a derivative thereof, wherein at least one hydroxy group of residues $A^1-A^3$, D, $Q^1-Q^3$ and $Z^1-Z^3$ is esterified with sulfuric acid, and pharmaceutically usable salts thereof are useful for the treatment of disorders which are characterized by excessive or destructive proliferation of smooth muscle cells.

27 Claims, 1 Drawing Sheet

U.S. PATENT DOCUMENTS

| | | | |
|---|---|---|---|
| 5,008,247 | 4/1991 | Meinetsberger | 514/23 |
| 5,037,973 | 8/1991 | Meinetsberger | 536/53 |
| 5,298,616 | 3/1994 | Hosang et al. | 536/118 |
| 5,447,919 | 9/1995 | Hosang et al. | 514/53 |
| 5,521,160 | 5/1996 | Chucholowski et al. | 514/42 |

FOREIGN PATENT DOCUMENTS

| | | |
|---|---|---|
| 247721 | 4/1987 | European Pat. Off. . |
| 312086 | 10/1988 | European Pat. Off. . |
| 6603997 | 3/1966 | Netherlands . |

OTHER PUBLICATIONS

O. Mitsunobu, Synthesis 12, pp. 1–28 (1981).

R. F. Heck, Organic Reactions 27, pp. 345–390 (1982).

Teien et al. Thrombosis Research 10, pp. 399–410 (1977).

Bayer 98(7) (1982):54399d.

Fisons AG/CA Pharmaceuticals Ltd. 26th Sep. 1966, CA 67:100002d.

B. Lamm et al. Acta Chem. Scand. B 41, pp. 202–207 (1987).

R. A.Murphy et al. J. Med. Chem. 33, pp. 171–178 (1990).

H. Kapitza & R. Zentel, Makromol Chem. 192, pp. 1859–1872 (1991).

Y. Le Merrer et al. Heterocycles 25 pp. 541–548 (1987).

E. Hungerbühler & D. Seebach, Helvetica Chimica Acta 64 pp. 687–702 (1981).

E. Weber et al., Chem. Ber. 122 pp. 959–967 (1989).

Meyer zu Reckendorf, Chem. Ber 107, pp. 869–875 (1974).

SULFURIC ACID ESTERS OF SUGAR ALCOHOLS

SUMMARY OF THE INVENTION

The present invention relates to esters of sugar alcohols and sugar alcohol-like compounds of formulas

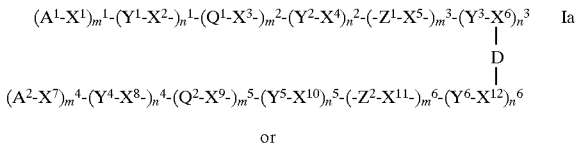

wherein
- $n^1$–$n^9$ are each independently 0 or 1;
- $m^1$–$m^9$ are each independently 0 or 1, but with the proviso that at least one of $m^1$, $m^2$ and $m^3$, at least one of $m^4$, $m^5$ and $m^6$ and, when present, at least one of $m^7$, $m^8$ and $m^9$ is 1; and wherein
- $X^1$–$X^{18}$ each independently are —O—, —CONR$^1$—, —NR$^1$CO— or —NR$^1$—;
- $R^1$ is hydrogen or lower alkyl;
- W is a benzene group or a s-triazine group;
- $Y^1$–$Y^9$ each independently are aromatic ring systems;
- $A^1$–$A^3$ each independently are a residue of a sugar alcohol devoid of the 1-hydroxy group or a derivative thereof, a residue of a sugar acid devoid of the 1-carboxy group or a derivative thereof or the tris-(hydroxymethyl)-methyl group;
- D is the di-residue of a sugar alcohol devoid of 2 hydroxy groups or a derivative thereof or the di-residue of a sugar dicarboxylic acid devoid of 2 carboxy group or a derivative thereof;
- $Q^1$–$Q^3$ and $Z^1$–$Z^3$ each independently are the di-residue of a sugar alcohol devoid of 2 hydroxy groups or a derivative thereof or the di-residue of a sugar dicarboxylic acid devoid of 2 carboxy groups or a derivative thereof or a didesoxyglycopyranoside residue or a derivative thereof, with at least one hydroxy group of residues $A^1$–$A^{14}$, D, $Q^1$–$Q^3$ and $Z^1$–$Z^3$ being esterified with sulfuric acid, and pharmaceutically usable salts thereof.

A carbon atom which is not present in a ring system and which carries a free hydroxy group or a hydroxy group esterified with sulfuric acid should not be simultaneously bonded to a further hetero atom.

In another aspect, the invention relates to pharmaceutical preparations containing a compound of formula Ia or Ib or a salt thereof; the use of the compounds of formula Ia or Ib and their salts as medicaments, especially for the treatment and/or prophylaxis of disorders which are characterized by excessive or destructive proliferation of smooth muscle cells and of artereosclerotic vascular wall changes, for example, for preventing restenosis after coronary or peripheral angioplasty or after bypass operations, and, respectively, for the production of medicaments for the said indications; as well as a process for the manufacture of the compounds of formula Ia or Ib and their salts.

DETAILED DESCRIPTION OF THE INVENTION

Figure 1:
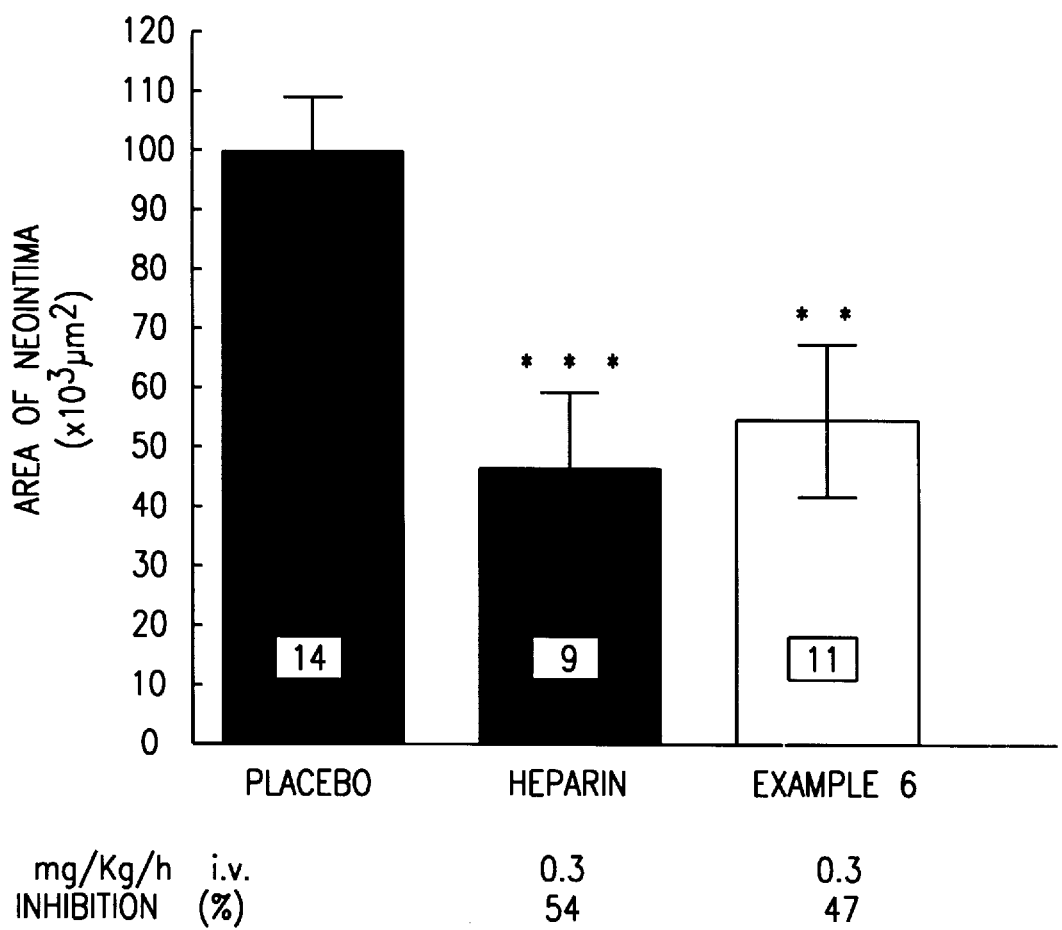
FIG. 1 is a bar graph of the cross sectional area of the neointima in rat carotids of animals administered a compound of the invention compared to animals administered heparin and placebo.

The present invention relates to compounds of the formula

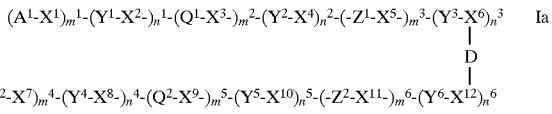

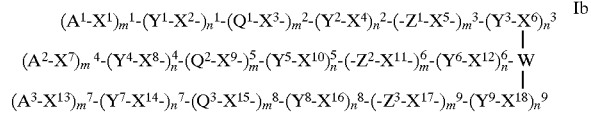

wherein
- $n^1$–$n^9$ are each independently 0 or 1;
- $m^1$–$m^9$ are each independently 0 or 1, but with the proviso that at least one of $m^1$, $m^2$ and $m^3$, at least one of $m^4$, $m^5$ and $m^6$ and, when present, at least one of $m^7$, $m^8$ and $m^9$ is 1; and wherein
- $X^1$–$X^{18}$ each independently is —O—, —CONR$^1$—, —NR$^1$CO— or —NR$^1$—;
- $R^1$ is hydrogen or lower alkyl;
- W is a benzene or s-triazine;
- $Y^1$–$Y^9$ each independently is an aromatic ring system;
- $A^1$–$A^3$ each independently is a residue of a sugar alcohol devoid of the 1-hydroxy group or a derivative thereof, a residue of a sugar acid devoid of the 1-carboxy group or a derivative thereof or tris-(hydroxymethyl)-methyl;
- D is the di-residue of a sugar alcohol devoid of 2 hydroxy groups or a derivative thereof or the di-residue of a sugar dicarboxylic acid devoid of 2 carboxy group or a derivative thereof;
- $Q^1$–$Q^3$ and $Z^1$–$Z^3$ each independently is the di-residue of a sugar alcohol devoid of 2 hydroxy groups or a derivative thereof or the di-residue of a sugar dicarboxylic acid devoid of 2 carboxy groups or a derivative thereof or didesoxyglycopyranoside or a derivative thereof, wherein at least one hydroxy group of residues $A^1$–$A^3$, D, $Q^1$–$Q^3$ and $Z^1$–$Z^3$ are esterified with sulfuric acid with the proviso that a carbon atom which is not present in an aromatic ring system and which is bonded to hydroxy or hydroxy esterified with sulfuric acid is not bonded to another hetero atom, and pharmaceutically usable salts thereof.

The following structural elements are features of compounds of formulas Ia and Ib:

a) Mono-residues of sugar alcohols or sugar acids which are linked via a suitable functional group, for example, $A^1$—$X^1$, $A^2$—$X^7$ and the like.

b) di-residues of sugar alcohols or sugar acids or of didesoxyglycopyranosides which are linked via two suitable functional groups, for example, $X^6$—D—$X^{12}$, $X^2$—$Q^1$—$X^3$, $X^4$—$Z^1$—$X^5$ and the like.

c) aromatic units which are linked via two suitable functional groups, for example, $X^1$—$Y^1$—$X^2$, $X^3$—$Y^2$—$X^4$ and the like.

d) aromatic units which are linked via three suitable functional groups, for example,

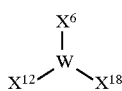

Compounds of different molecular size can be synthesized by linking these structural elements.

Compounds of the invention contain at least three groups which are derived from a sugar alcohol, a sugar acid or from a glyco-pyranoside.

In a preferred embodiment of a compound of formula Ia or Ib the two or, respectively, three side chains are identical; each of $Y^1$–$Y^9$ are a)
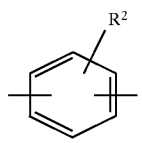

b)
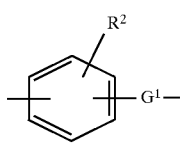

c)
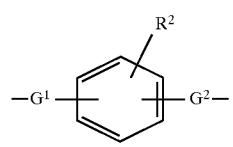

e)
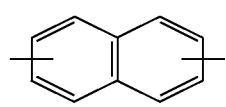

f)
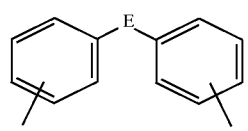

g)
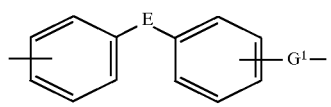

or d)
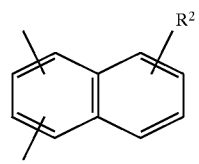

h)
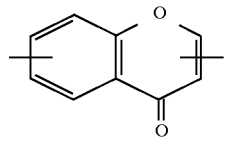

wherein $R^2$ is hydrogen, halogen, nitro, lower alkyl, lower alkoxy, lower aralkoxy, carbamoyl or glycerol, wherein the hydroxy groups present are optionally sulfated, $G^1$ and $G^2$ are lower alkylene, lower alkenylene, lower alkynylene or lower alkyleneoxy;

E is a carbon-carbon bond; —O—, —CO—, —CH$_2$—, —CH$_2$—CH$_2$—, —CH=CH—, —C≡C—, NR$^3$—CO— or —CO—NR$^3$—; and $R^3$ is hydrogen or lower alkyl; and $A^1$–$A^3$, D, $Q^1$–$Q^3$, $Z^1$–$Z^3$ are derived from a hexitol, a pentitol, a tetritol, glycerol or tris-(hydroxymethyl)-methane.

In the aromatic units which are linked via three suitable functional groups there are preferred compounds of formula Ib in which $m^2$, $m^{3,}$ $m^5$, $m^6$, $m^8$, $m^9$ and $n^2$, $n^3$, $n^5$, $n^6$, $n^8$ and $n^9$ are O.

Any conventional sugar alcohol can be used. Examples of suitable sugar alcohols from which the residues $A^1$–$A^3$, D, $Q^1$–$Q^3$ and $Z^1$–$Z^3$ are derived are hexitols such as glucitol, galactitol, mannitol and gulitol; pentitols such as arabinitol, ribitol and xylitol; tetritols such as threitol and erythritol or glycerol. Derivatives of such sugar alcohols can be mono- or multiply-desoxygenated sugar alcohols such as L-rhamnitol.

Ribonic acid, gluconic acid and gulonic acid are examples of sugar carboxylic acids from which residues $A^1$–$A^3$ are derived.

Tartaric acid, galactaric acid and glucaric acid are examples of sugar dicarboxylic acids from which residues D, $Q^1$–$Q^3$ and $Z^1$–$Z^3$ are derived These sugar alcohols and sugar carboxylic acids can be present in the D- or L-form or as racemates, with the naturally occurring form or the form which corresponds to the basic, naturally occurring sugar being preferred.

Preferably, residues $A^1$–$A^3$ are derived from glucitol, arabinitol, glycerol or from tris-(hydroxymethyl)-methane.

A derivative of a sugar alcohol is, for example, a corresponding ether at $C_1$ or a cyclic compound of the formula

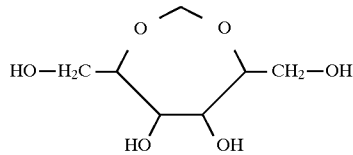

A derivative of a didesoxyglycopyranoside residue is, for example, a corresponding ether at $C_1$.

Examples of aromatic ring systems $Y^1$–$Y^9$ in formula Ia or Ib are residues of formulas a)–h):

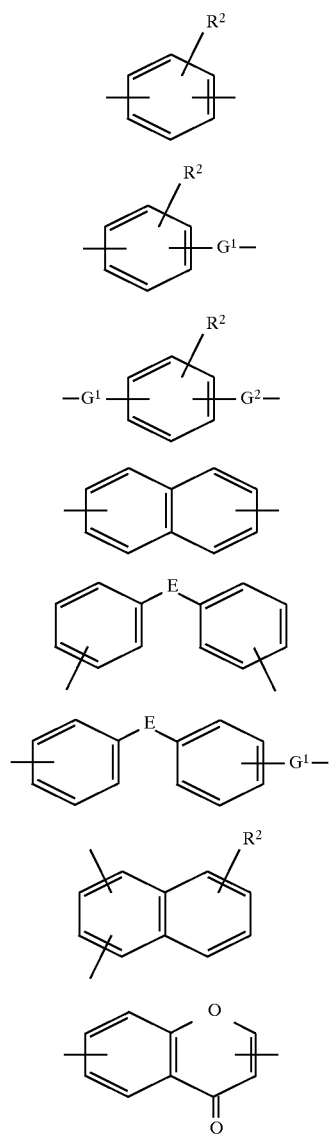

a)
b)
c)
e)
f)
g)
d)
h)

wherein
R² is hydrogen, halogen, nitro, lower alkyl, lower alkoxy, lower aralkoxy, carbamoyl or glycerol, with hydroxy groups present also being optionally sulfated,
G¹ and G² are lower alkylene, lower alkenylene, lower alkynylene or lower alkyleneoxy;

E is a carbon-carbon bond; —O—, —CO, —CH₂—, —CH₂—CH₂—, —CH=CH—, —C≡C—, —NR³—CO— or —CO—NR³—; and R³ is hydrogen or lower alkyl.

The term "lower alkyl" and "lower alkylene" means straight-chain or branched saturated hydrocarbon groups with up to 7, preferably up to 4, carbon atoms such as methyl, ethyl, n-propyl, isopropyl, n-butyl, isobutyl, tert.butyl and the like.

In an analogous manner, the terms "lower alkenyl" and "lower alkenylene" as well as "lower alkynyl" and "lower alkynylene" mean unsaturated hydrocarbon groups which contain a double or, respectively, triple bond and which have up to 7, preferably up to 4, carbon atoms such as vinyl, allyl, ethynyl, propargyl and the like.

The term "lower alkoxy" and "lower alkyleneoxy" mean alkyloxy groups and, respectively, alkyleneoxy groups in the sense of the above description of the terms "lower alkyl" and, respectively, "lower alkylene".

The term "aralkoxy" means alkoxy groups substituted by phenyl and biphenyl groups.

The term "halogen" means fluorine, chlorine, bromine and iodine, of which bromine is preferred.

Phenylene groups of formulae a)–c) are preferably 1,4-phenylene groups.

In formulae f) and g) the bonds emanating from the rings are preferably situated in the p-position to one another.

Examples of salts of compounds of formulas Ia or Ib are alkali metal salts such as Na or K salts, ammonium salts and salts of tertiary amines such as triethylamine or pyridinium or imidazolium salts or quaternary ammonium salts such as dodecyl-trimethyl-ammonium, ethylpyridinium and benzethonium salts; as well as alkaline earth metal salts such as Ca or Mg salts.

Preferred compounds of formula I are:
1,6-Bis-O-[6-methoxy-3-(2,3,4,5,6-penta-O-sulfo-D-glucit-1-ylcarbamoyl)-naphthalen-2-yl]-2,3,4,5-tetra-O-sulfo-galactitol tetradecasodium salt (Example 20);

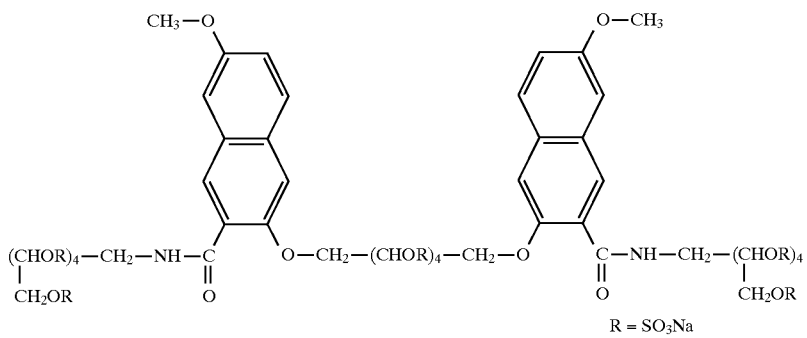

1,6-Bis-O-[8-methoxy-3-(2,3,4,5,6-penta-O-sulfo-D-glucit-1-ylcarbamoyl)-naphthalen-2-yl]-2,3,4,5-tetra-O-sulfo-galactitol tetradecasodium salt (Example 21);

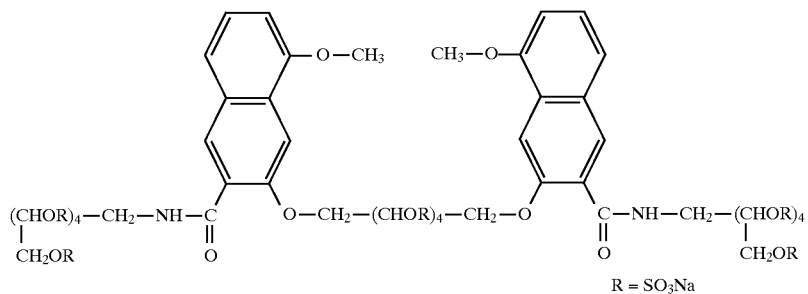
1,6-Bis-O-[4-[4-O-[3-(2,3,4,5,6penta-O-sulfo-D-glucit-1-ylcarbamoyl)-naphthalen-2-yl]-2,3,-di-O-sulfo-L-threit-1-yloxy]-phenyl]-2,3,4,5-tetra-O-sulfo-galactitol octadecasodium salt (Example 50);
1,6-Bis-O-[3-[4-O-[3-(2,3,4,5,6penta-O-sulfo-D-glucit-1-ylcarbamoyl)-naphthalene-2-yl]-2,3-di-0-sulfo-L-threit-1-yloxy]-naphthalen-2-yl]-2,3,4,5-tetra-O-sulfo-galactitol octadecasodium salt (Example 54);
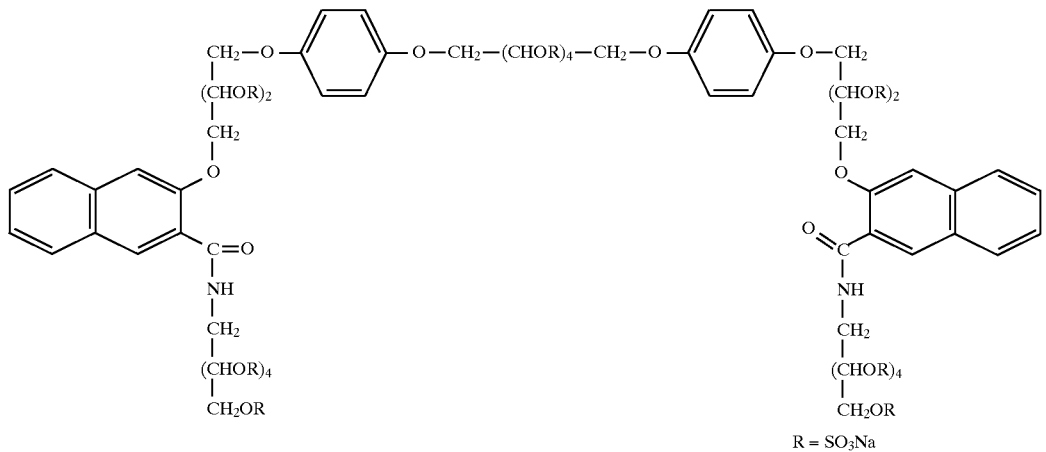

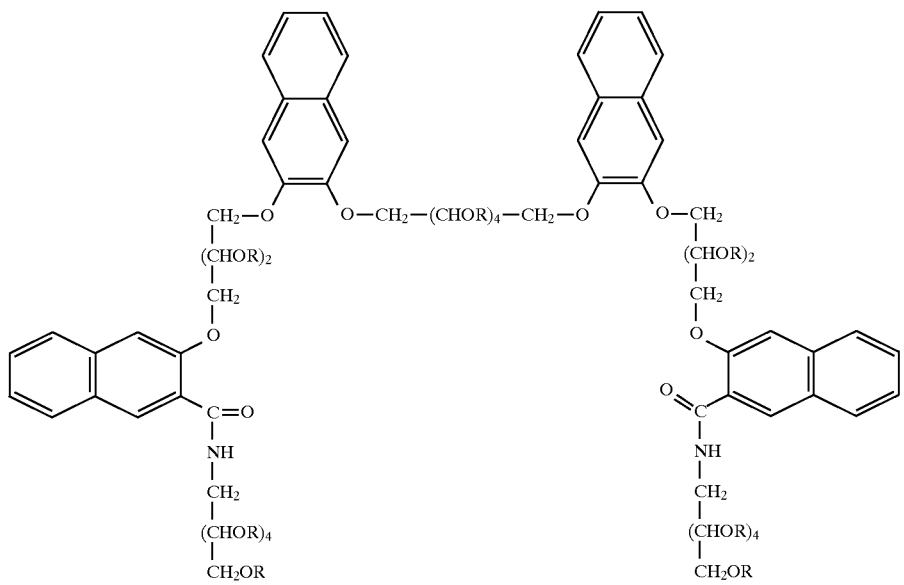
1,6Bis-O-[4-[(E)-2-[benzyl-2,6-didesoxy-6-(2,3,4,5,6-penta-O-sulfo-D-gluconoylamino)-3,4-di-O-sulfo-a-D-glucopyranosid-2-ylcarbamoyl]-vinyl]-phenyl]-2,3,4,5-tetra-O-sulfo-galactitol octadecasodium salt (Example 57);
Especially preferred compounds of general formula I are:
1,6-Bis-O-[4-[2-(2,3,4,5,6-penta-O-sulfo-D-glucit-1-ylcarbamoyl)-ethyl]-phenyl]-2,3,4,5-tetra-O-sulfo-galactitol tetradecasodium salt (Example 6),
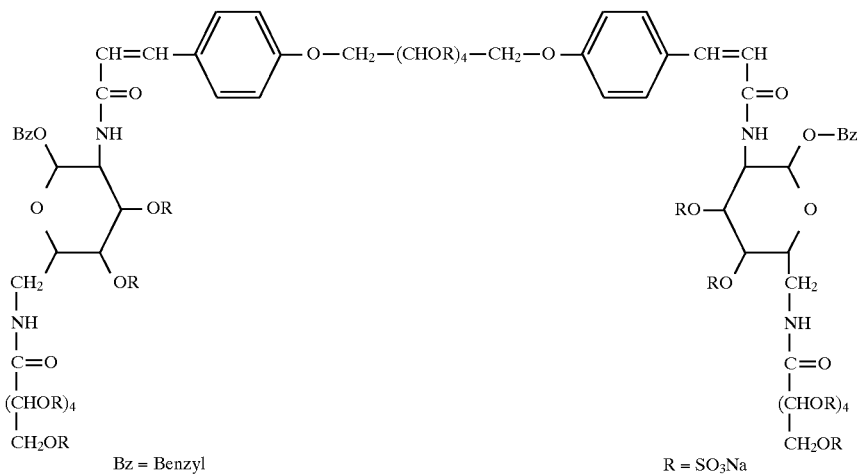
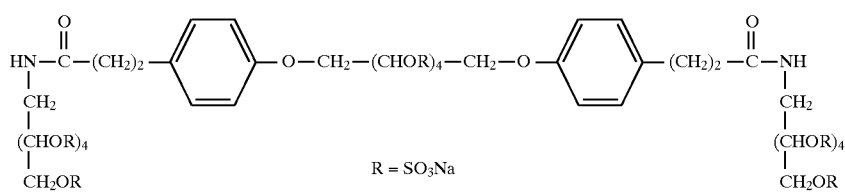

11

1,6-Bis-O-[4-[2-[4-(2,3,4,5,6-penta-O-sulfo-D-glucit-1ylcarbamoyl)-phenyl]-ethyl]-phenyl]-2,3,4,5-tetra-O-sulfo-galactitol tetradecasodium salt (Example 11),

12

1,6-Bis-O-[6-[(S)-2,3-bis-sulfoxy-propoxy]-3-(2,3,4,5,6-penta-O-sulfo-D-glucit-1-ylcarbamoyl)-naphthalen-2-yl]-2,3,4,5-tetra-O-sulfo-galactitol octadecasodium salt (Example 22),

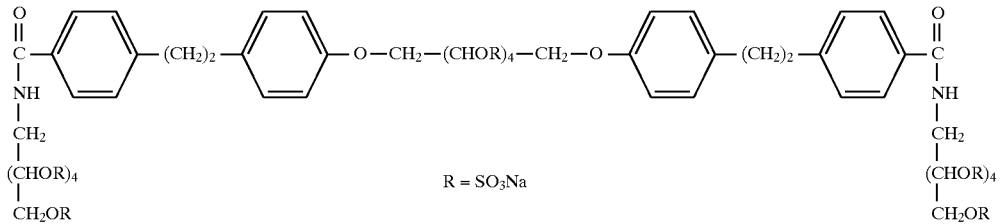

1,6-Bis-O-[3-(2,3,4,5,6-penta-O-sulfo-D-glucit-1-ylcarbamoyl)-naphthalen-2-yl]-2,3,4,5-tetra-O-sulfo-galactitol tetradecasodium salt (Example 14),

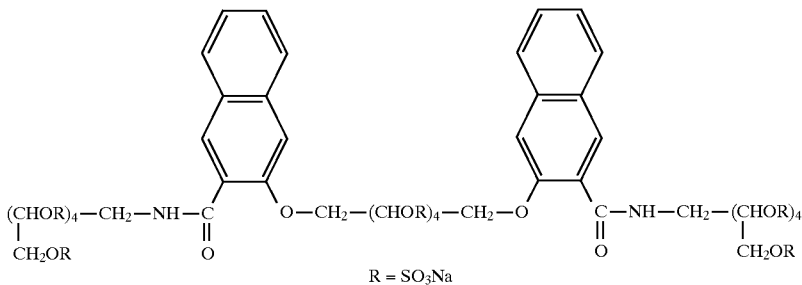

1,6-Bis-O-[6-(2,3,4,5,6-penta-O-sulfo-D-glucit-1-ylcarbamoyl)-naphthalen-2-yl]-2,3,4,5-tetra-O-sulfo-galactitol tetradecasodium salt (Example 16),

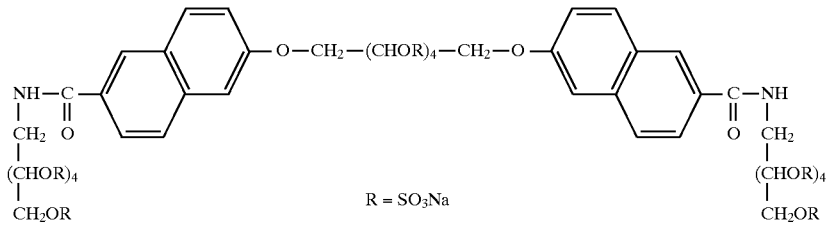

1,6-Bis-O-[3-biphenyl-4-ylmethoxy-5-(2,3,4,5,6-penta-O-sulfo-D-glucit-1-ylcarbamoyl)-phenyl]-2,3,4,5-tetra-O-sulfo-galactitol tetradecasodium salt (Example 17),

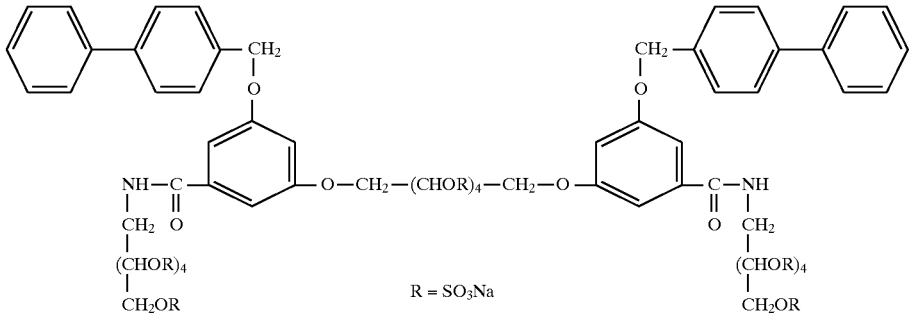

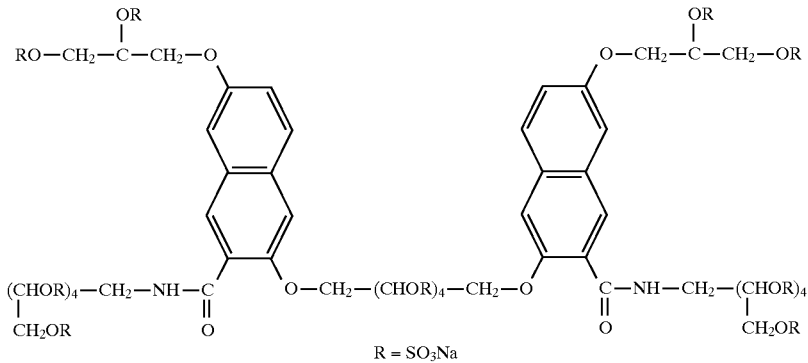

1,6-Bis-O-[3-(2,3,4,5-tetra-O-sulfo-D-arabinit-1-yloxy)-naphthalen-2-yl]-2,3,4,5-tetra-O-sulfo-galactitol dodecasodium salt (Example 40),

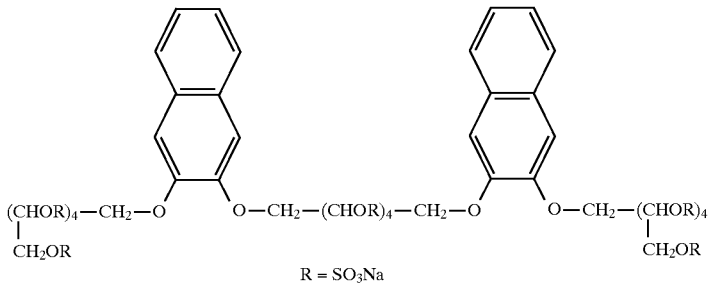

2,3,4,5-Tetra-O-sulfo-1,6-bis-O-[4-[4-(2,3,4,5-tetra-O-sulfo-D-arabinit-1-yloxy)-benzyl]-phenyl]-D-mannitol dodecasodium salt (Example 43),

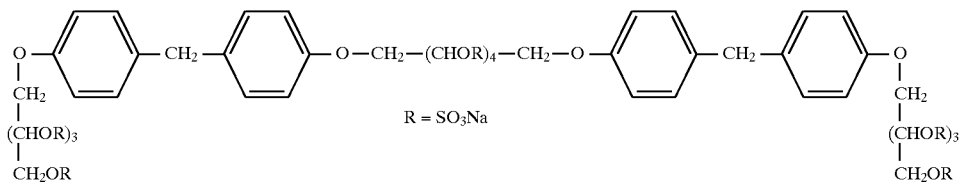

1,6-Didesoxy-2,3,4,5-tetra-O-sulfo-1,6-bis-[3-(2,3,4,5-tetra-O-sulfo-D-arabinit-1-yloxy)-naphthalen-2-ylcarbonylamino]-galactitol dodecasodium salt (Example 45),

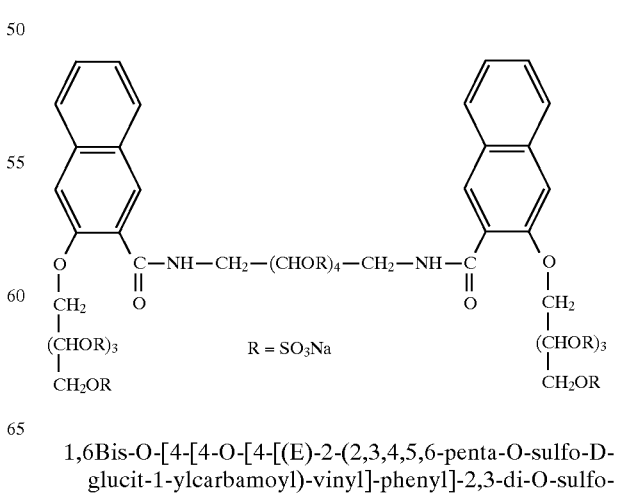

1,6Bis-O-[4-[4-O-[4-[(E)-2-(2,3,4,5,6-penta-O-sulfo-D-glucit-1-ylcarbamoyl)-vinyl]-phenyl]-2,3-di-O-sulfo- D-threit-1-yloxy]-phenyl]-2,3,4,5-tetra-O-sulfo-galactitol octadecasodium salt (Example 48), glucopyranosid-2-ylcarbamoyl]-naphthalen-1-yl]-2,3,4,5-tetra-O-sulfo-galactitol octadecasodium salt

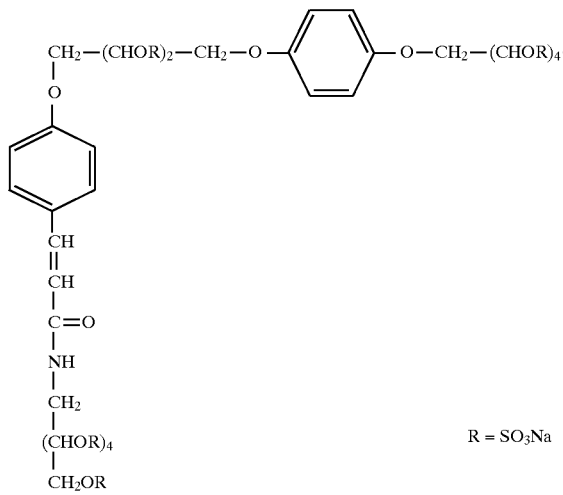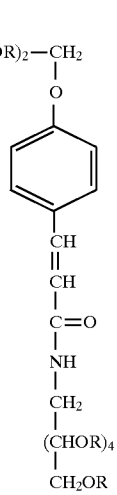

1,6Bis-O-[4-[4-O-[4-[(E)-2-[methyl-(2,3,4,5,6-penta-O-sulfo-D-glucit-1-yl)-carbamoyl]-vinyl]-phenyl]-2,3-di-O-sulfo-D-threit-1-yloxy]-phenyl]-2,3,4,5-tetra-O-sulfo-galactitol octadecasodium salt (Example 52),

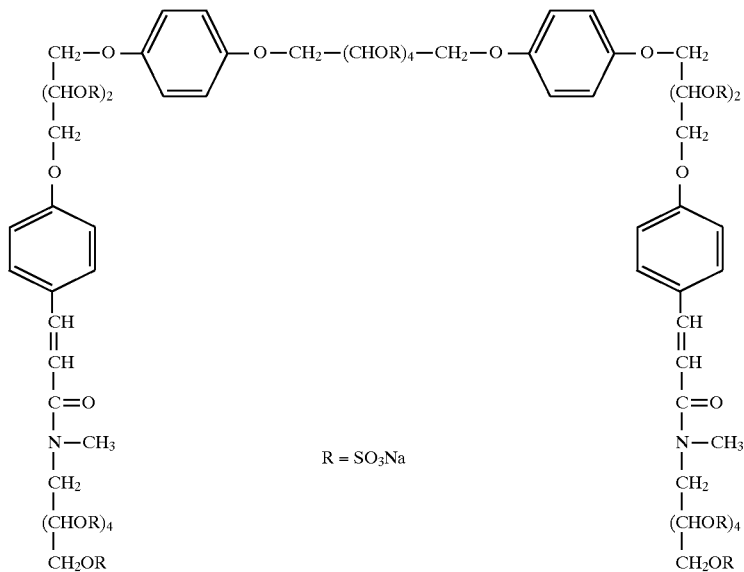

1,6Bis-O-[3-[benzyl-2,6-didesoxy-6-(2,3,4,5,6-penta-O-sulfo-D-gluconoylamino)-3,4-di-O-sulfo-a-D-

(Example 56),

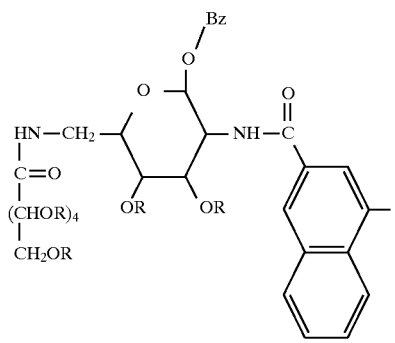
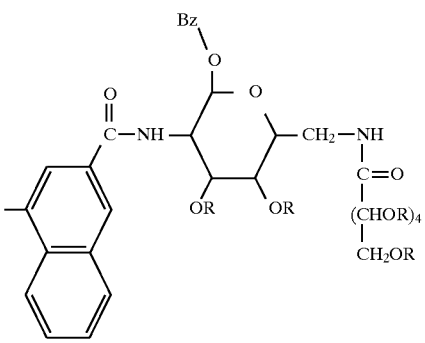

R = SO₃Na    Bz = Benzyl 1,6-Bis-O-[4-[2-[benzyl-2,6-didesoxy-6-(2,3,4,5,6-penta-O-sulfo-D-gluconoylamino)-3,4-di-O-sulfo-a-D-glucopyranosid-2-ylcarbamoyl]-ethyl]-phenyl]-2,3,4,5-tetra-O-sulfo-galactitol octadecasodium salt (Example 58), 1,6-Bis-O-[6-[benzyl-2,6-didesoxy-2-[3-nitro-4-(2,3,4,5,6-penta-O-sulfo-D-glucit-1-ylamino)-benzoylamino]-3,4-di-O-sulfo-a-D-glucopyranosid-6-ylcarbamoyl]-naphthalen-2-yl]-2,3,4,5-tetra-O-sulfo-galactitol octadecasodium salt (Example 59),

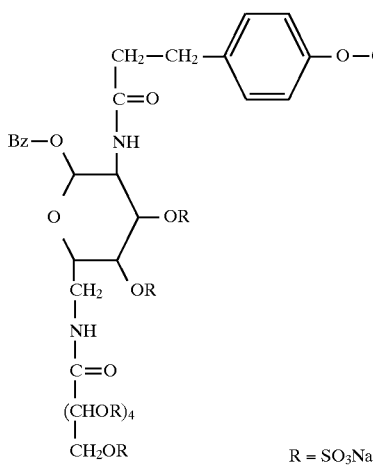
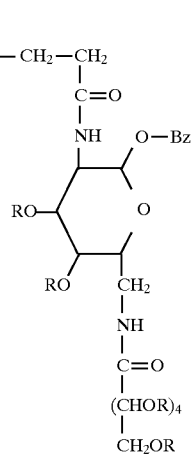

R = SO₃Na    Bz = Benzyl

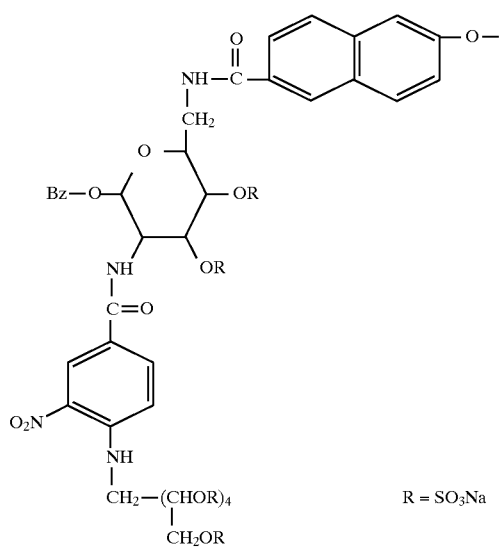
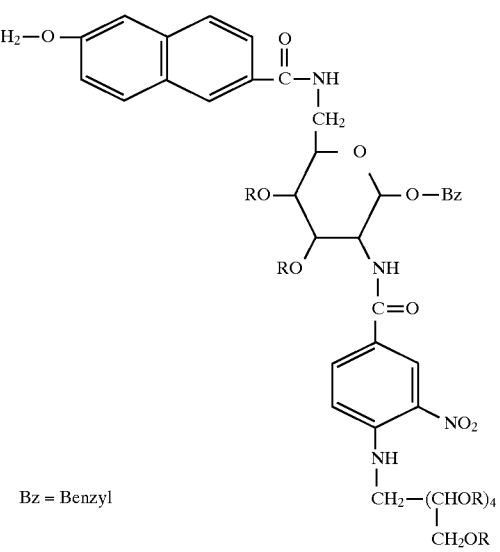

R = SO₃Na   Bz = Benzyl 1,6-Bis-O-[4-[(E)-2-[benzyl-2,6-didesoxy-2-[4-(2,3,4,5,6-penta-O-sulfo-D-glucit-1-ylamino)-3-nitro-benzoylamino]-3,4-di-O-sulfo-a-D-glucopyranosid-6-ylcarbamoyl]-vinyl]-phenyl]-2,3,4,5-tetra-O-sulfo-galactitol octadecasodium salt (Example 61),

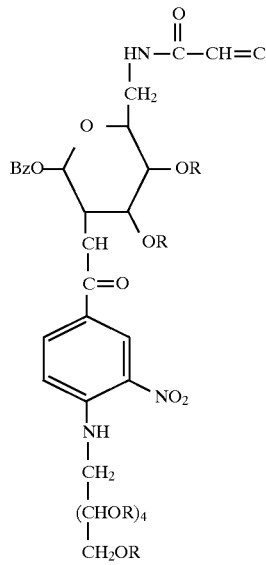
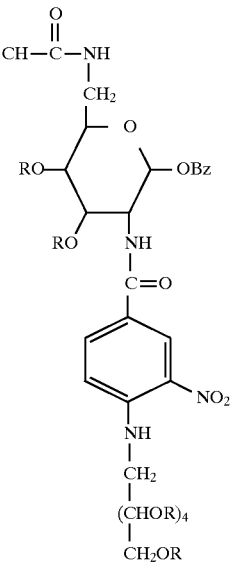

R = SO₃Na   Bz = Benzyl

The compounds defined hereinbefore can be prepared by reacting a corresponding, non-sulfated compound with a sulfating agent.

The sulfation in accordance with the invention can be performed using methods which are known per se for the sulfation of hydroxy groups. Examples of sulfating agents are $SO_3$ complexes such as $SO_3$.pyridine, $SO_3$.trimethylamine, $SO_3$.dioxan and $SO_3$.dimethylformamide. Further examples of sulfating agents are chlorosulfonic acid, mixtures of chlorosulfonic acid and sulfuric acid, and piperidine N-sulfate.

The reaction is conveniently effected in a suitable solvent, especially a polar solvent, for example, dimethylformamide, dimethyl sulfoxide or hexamethylphosphortriamide. The reaction can be carried out at room temperature or at an elevated temperature, for example, at 20°–70° C., whereby the degree of sulfation can be influenced by varying the reaction duration and temperature. The degree of sulfation achieved in each case can be determined by HPLC. In a preferred embodiment, all or practically all free hydroxy groups are sulfated by suitable choice of reaction duration and temperature. The working up of the reaction mixture and, respectively, the isolation of the reaction product can be effected according to known methods, for example, by gel filtration or ultrafiltration. Conveniently, the reaction mixture is treated, prior to the working up, with a compound which is sufficiently basic to be capable of forming a salt with the sulfonic acid groups in the compounds defined hereinbefore, for example, with an alkali metal acetate such as sodium acetate, and the compound of formula Ia or Ib is isolated in salt form, for example, as the sodium salt.

The starting materials for the process in accordance with the invention, that is, the non-sulfated compounds corresponding to the compounds of formulas Ia and Ib, can be prepared as described in the Examples hereinafter or in analogy thereto. The various intermediates via which substances of formulas Ia and Ib are prepared can in general be prepared stepwise as follows beginning with known compounds or compounds which are readily accessible in analogy to known compounds:

Residues of sugar alcohols, didesoxyglycopyranosides or the tris-(hydroxymethyl)-methyl residue as well as derivatives of sugar mono- and di-carboxylic acids, hydroxy functions of which are free or are protected by usual protecting groups such as acetonides, methylene acetals, aryl methyl ethers, alkyl or aryl esters, and the like, having desoxy sites can be closed to oxirane rings or with carboxylic acid functions to 5- or 6-membered lactones, and which carry one or, respectively, two functional groups suitable for the subsequent reaction can be linked according to different linkage patterns and in variable sequence by the simultaneous formation of one or more new bonds per reaction step with likewise suitably functionalized aromatic units $Y^1$–$Y^9$ or to the aromatics W or in their absence with other suitable mono- or difunctional polyol derivatives. Before the linkage reaction is repeated, the functional groups required for the linkage reaction must in each case be prepared for the next linkage reaction by removing a protecting group, including also the reduction of a nitro group, or by introducing a suitable activating function unless bifunctional compounds are reacted selectively at only one functional site. When repeating the linkage reaction, at least one of the units to be linked is already a more complex compound, which not only has polyol derivatives but also aromatic sub-units; optionally now the fresh linkage reaction can also be carried out between two aromatic sub-units. The non-sulfated precursors to formulas Ia and Ib are obtained after the structure has been synthesized and after the protecting groups have been removed.

When the linkage reaction comprises the formation of an amide bond, then this can be formed by reacting a component having a free amino function with the second component in the form of an aliphatic ester, lactone, an acid chloride or an acid function activated according to known methods in peptide chemistry (mixed anhydride or active ester).

When the linkage reaction is the formation of an ether function, then free hydroxy functions can be linked to a sugar residue with a phenol or a benzylic or allylic alcohol according to known methods either without previous activation of the alcohol function according to Mitsunobu (O. Mitsunobu, Synthesis 12, 1 (1981)) or after activation of the alcohol function. Such an activation can be effected by conversion into halides or alkylsulfonates or arylsulfonates or by formation of an epoxide with an adjacent hydroxy function.

When the linkage reaction is the formation of an arylamine, then this can be achieved by known methods for reacting aminoglycitols with activated aromatics.

The synthesis of aromatic residues with synthones which already contain polyol derivatives—optionally protected at the hydroxy functions—can be carried out using C—C bond-forming reactions. Thereby, there are preferably used reactions which can proceed under mild reaction conditions, such as by palladium-catalyzed vinylation and acetylynation reactions of the "Heck" type (R. F. Heck, Organic Reactions 27, 345 (1982)).

The removal of any protecting groups still present after synthesis of the structure is effected according to generally conventional methodology.

Solid carrier reaction technology is especially suitable for the synthesis of asymmetric compounds. Thereby, a first synthesis unit is bonded to a suitably functionalized resin via a labile function, for example, a labile amide function. After subsequent liberation of a suitable functional group by removing a protecting group which may be present, a monoreaction can now be achieved selectively not only with a mono- but also with a difunctional synthone in excess. Thereby, a functional group remains in the compound bonded to the resin and a further reaction with a second bifunctional unit can follow directly. This procedure can be repeated several times. A monofunctional polyol derivative can finally be used to break the chain. A possible linkage reaction, to which this principle can be applied, is the formation of ether functions. Thereby, the aforementioned reaction conditions for the formation of ether bonds are used. The compound bonded to the resin can finally be cleaved off from the resin by a specific cleavage reaction, for example, under acidic conditions; then after removing any protecting groups still present at non-sulfated precursor of the compounds defined hereinbefore is obtained.

The compounds in accordance with the invention inhibit the migration and proliferation of smooth muscle cells of the vascular wall. They thus are useful for the treatment and/or prophylaxis of disorders which are characterized by excessive or destructive proliferation of smooth muscle cells and of arteriosclerotic changes of the vascular wall, especially for the prevention of restenosis after coronary or peripheral angioplasty or after bypass operations. In principle, these substances can be used for the treatment and/or prophylaxis of all conditions in which migration or proliferation of smooth muscle cells plays a role.

In contrast to heparin, these compounds have no $AT_{III}$ activity (antithrombin III) and therefore no inhibiting effect on coagulation factors IIa and Xa. Accordingly, their blood coagulation-inhibiting activity is very much lower than that of heparin and thus the risk of bleeding in the case of therapy with these substances is minimal.

Since heparin-binding proteins play an important role in various illnesses, heparin-like substances such as the compounds in accordance with the invention can, in addition, also be used for the treatment of these illnesses: for example, infection by various viruses (herpes, HIV) is inhibited by such substances, arterial thrombosis (vWF, platelet adhesion) is inhibited by such substances, activation of the complementary system (for example, in the case of reperfusion) can be diminished and various growth factors or cytokines (for example, bFGF in tumors) can be inhibited.

The pharmacological activities of the compounds in accordance with the invention can be demonstrated in the test procedures described hereinafter:

Antiproliferative activity

The antiproliferative activity of a substance is expressed as the $r_i$ value which is a comparative value to the corresponding activity of heparin and which was determined in cell cultures as follows: rat smooth muscle cells were applied to cell culture plates in a density of $8\times10^3$ cells/well, medium: DMEM (Dulbecco Modified Eagle Medium) with 10% FCS (fetal calf serum); cultivation at 37° C. and 5% $CO_2$. After 4 hours, the number of adhered cells was determined and the substances to be tested (100 µg/ml, dissolved in $H_2O$) were added. The controls were a) cells to which test compound was not added and b) cells which had been treated with heparin (100 µg/ml). Subsequently, the cells were incubated for 48 h. and thereafter the cell count was determined once more.

The inhibition i of the cell growth, that is, the reduction in the growth rate of the cells in per cent compared to the control, was calculated from these values.

$$i = 100 - \frac{\mu \text{ substance}}{\mu \text{ control}} \cdot 100$$

with the growth rate $\mu$ being calculated as $$\mu = \frac{\Delta \ln Z}{\Delta t_{[d]}} = \ln \frac{Z_{(t2)}}{Z_{(t1)}} * \frac{1}{\Delta t_{[d]}} \; [d^{-1}]$$

in which Z is the number of cells and d is the time in days.

Finally, $r_i$—the relative inhibitory activity—which expresses the activity of a substance (at 100 μg/ml) in comparison to the activity of heparin in the same concentration in the same experiment, was calculated $$r_i = \frac{i \text{ substance}}{i \text{ heparin}}$$

Blood coagulation inhibition

The blood coagulation-inhibiting activity was determined as follows:

Inhibition of thrombin or factor Xa in the chromogenic substrate assay (Teien et al., Thrombosis Research 10, 399–410 (1977)): The determination was effected in a Cobas-Bio centrifugal automatic spectrophotometer. The buffer solution used consisted of 50 mM Tris buffer, 180 mM NaCl, 7.5 mM EDTA Na$_2$, 1% PEG 6000 and 0.02% Tween 80, pH 8.4. The assay solution consisted of 50 μl of buffer, 30 μl of antithombin III (1 U/ml, Kabi Diagnostica) and 20 μl of plasma which contained various concentrations of test compounds. 30 μl of sample solution and 20 μl of water with 180 μl of thrombin (1 U/ml, thrombin reagent, Roche Basle) were added to the test cuvette in the automatic analyzer. After incubation at 37° C. for 240 seconds, 60 μl of S-2238 (H-D-Phe-Pip-Arg-NH.pNA, Kabi Diagnostica, Möndal, Sweden, 0.75 mM in water) and 20 μl of water were added. The liberation of pNA (p-nitro-aniline) was followed during 60 seconds at 405 nM in 10 second intervals in comparison to water as the blank. The inhibitory activity is given as the IC$_{50}$, which is the concentration [μg/ml] at which the amidolytic activity of thrombin is reduced by 50% in comparison to the plasma control value.

The inhibition of factor Xa was measured in the same manner using a solution of factor Xa (2.8 nkat/ml and 2 mM S-2222 (Bz-CO-Ile-Glu-Arg-NH.pNA, Kabi Diagnostica) in water in place of thrombin and, respectively, S-2238.

The activity data obtained in the previously described test procedures with a representative number of compounds of formula I are given in the following Table:

| Example | Antiproliferative Activity $r_i$ | Anticoagulavite Activity IC$_{50}$ [μg/ml] | |
| --- | --- | --- | --- |
| | | Thrombin | Factor Xa |
| 6 | 0.7 | >1000 | >1000 |
| 11 | 2.2 | >1000 | >1000 |
| 14 | 1.5 | >1000 | >1000 |
| 16 | 2.1 | >1000 | >1000 |
| 17 | 1.5 | >1000 | >1000 |
| 22 | 2.1 | >1000 | >1000 |
| 40 | 1.4 | >1000 | >1000 |
| 43 | 1.3 | >1000 | >1000 |
| 45 | 1.4 | >1000 | >1000 |
| 48 | 2.7 | >1000 | >1000 |
| 52 | 0.8 | >1000 | >1000 |
| 56 | 1.7 | >1000 | >1000 |
| 58 | 1.8 | >1000 | >1000 |
| 59 | 1.8 | >1000 | >1000 |
| 61 | 2.4 | >1000 | >1000 |
| Heparin | 1.0 | 1.9 | 2.7 |

In vivo assay for determining the antiproliferative activity of the compounds in accordance with the invention in damaged rat carotids.

The left carotids of male Wistar Kyoto rats (300–400 g) were, after narcosis, damaged with a 2F embolectomy catheter by pulling the catheter in the pumped-up state through the vessel three times. After wound management, the animals were kept in pairs with standard feed and water ad libidum.

The compounds were administered in concentrations of 0.3–1 mg/kg/h i.v. For this purpose, an osmotic minipump was implanted under the dorsal skin of the animals during the narcosis and was connected with the jugular vein. Thus, the compounds could be administered constantly during the entire test period of 14 days.

After 14 days, proliferative tissue (neointima) had formed, the size of which could be determined morphometrically on histological cross-sections. In order to do this, the rats were sacrificed and perfusion-fixed with glutaraldehyde.

The cross sectional area of the neointima in rat carotids 14 days after balloonisation was significantly reduced (p<0.01, t-test) after i.v. administration of the compound of Example 6 (0.3 mg/kg/h). Thus, Example 6 achieved a comparable effect to that of concentrated heparin (the number of animals n is given in the FIG. 1; average±SEM).

The test results show that the compounds in accordance with the invention possess an antiproliferative activity which corresponds to (or approximates) or is greater than that of heparin, but in contrast to heparin they show no or only a much lower anti-coagulation activity.

The medicaments based on the compounds in accordance with the invention can be administered enterally, for example, orally in the form of tablets, coated tablets, dragées, hard and soft gelatin capsules, solutions, emulsions or suspensions, or rectally, for example, in the form of suppositories. The administration is, however, preferably effected parenterally, for example, in the form of injection solutions.

The active substance can be mixed with pharmaceutically inert, inorganic or organic excipients for the production of tablets, coated tablets, dragées and hard gelatine capsules. Lactose, corn starch or derivatives thereof, talc, stearic acid or its salts can be used for example, as such excipients for tablets, dragées and hard gelatin capsules. Suitable excipients for soft gelatin capsules are, for example, vegetable oils, waxes, fats, semi-solid and liquid polyols; depending on the nature of the active ingredient no excipients are, however, usually required in the case of soft gelatin capsules. Suitable excipients for the production of solutions and syrups are, for example, water, polyols, sucrose, invert sugar and glucose, suitable excipients for injection solutions are, for example, water, alcohols, polyols, glycerol and vegetable oils. Suitable excipients for suppositories are for example, natural or hardened oils, waxes, fats and semi-liquid or liquid polyols.

The pharmaceutical preparations can also contain preservatives, solubilizers, stabilizers, wetting agents, emulsifiers, sweeteners, colorants, flavorants, salts for varying the osmotic pressure, buffers, coating agents or antioxidants. In the case of enteral administration the resorption of the active ingredient can be enhanced with the aid of liposomes.

The dosage of the active ingredient can vary within wide limits and will, of course, be fitted to the individual requirements in each particular case. In general, in the case of parenteral administration a dosage of about 0.1 to 100 mg/kg, preferably of about 1.5 to 15 mg/kg, per day should be appropriate for adults, although the upper limit just given can also be exceeded when this is found to be indicated.

The invention is illustrated by the following Examples.

EXAMPLE 1

A. 1.024 g of 4,4'-dioxo-5,5'-(2-hydroxy-propane-1,3-diyldioxy)-di-4H-1-benzopyran-2-carboxylic acid disodium salt) (Neth. Appl. NL 6,603,997, Preparation of dichromonyl derivatives, Fisons Pharmaceuticals Ltd., 26th Sep. 1966, CA 67:100002d) were suspended in 15 ml of acetonitrile and 5 ml of dimethylformamide, subsequently treated with 0.5 ml of 4-methylmorpholine at 0°–5° C. with the exclusion of moisture and stirred intensively for 10 minutes. Thereupon, 0.704 g of solid 2-chloro-4,6-dimethoxy-1,3,5-triazine was added and the mixture was stirred at 0°–5° C. for a further 2 hours. Subsequently, 0.73 g of D-glucamine followed by 10 ml of dimethylformamide were added and the mixture was stirred at room temperature for a further 18 hours. Thereupon, the reaction mixture was diluted several times with water and evaporated several times at 40°–50° C. under reduced pressure, and the residue was treated with 20 ml of pyridine and 20 ml of acetic anhydride and stirred at room temperature for a further 60 hours. Then, this reaction mixture was again concentrated, the residue was treated with ice-water and 1N hydrochloric acid and extracted with methylene chloride. The combined methylene chloride phases were dried over magnesium sulfate and concentrated, and the residue was chromatographed on silica gel with ethyl acetate. The product fraction thereby obtained was dissolved in 11 ml of methanol and 3 ml of tetrahydrofuran and treated with 0.75 ml of 1 molar sodium methylate solution in methanol. The reaction mixture was stirred at room temperature for 2 hours. 5-[2-Hydroxy-3-[2-(D-glucit-1-ylcarbamoyl)-4-oxo-4H-1-benzopyran-5-yloxy]-propoxy]-4-oxo-4H-1-benzopyran-2-carboxylic acid D-glucit-1-ylamide was obtained as a colorless powder, MS: m/z 795.4 ([M+H]$^+$).

B. A suspension of 3.2 g of 5-[2-hydroxy-3-[2-(D-glucit-1-ylcarbamoyl)-4-oxo-4H-1-benzopyran-5-yloxy]-propoxy]-4-oxo-4H-1-benzopyran-2-carboxylic acid D-glucit-1-ylamide and 12.0 g of sulfur trioxide trimethylamine complex in 40 ml of absolute dimethylformamide was stirred at 70° C. for 18 hours. After cooling, the mixture was treated with 10 g of sodium acetate and 50 ml of water and evaporated, and the residue was treated several times with water and again evaporated. The thus-obtained residue was suspended in 300 ml of absolute methanol and mixed intensively. The insoluble residue was filtered off, dried in a vacuum, then taken up in water and chromatographed on SP Sephadex® C-25. The product fractions free from sodium sulfate were lyophilized and gave 4-oxo-5-[3-[4-oxo-2-(2,3,4,5,6-penta-O-sulfo-D-glucit-1-ylcarbamoyl)-4H-1-benzopyran-5-yloxy]-2-sulfooxy-propoxy]-4H-1-benzopyran-2-carboxylic acid 2,3,4,5,6-penta-O-sulfo-D-glucit-1-ylamide undecasodium salt, [a]–4.8° (c 0.6; water).

EXAMPLE 2

A. 184 mg of cyanuric chloride, 543.5 mg of D-glucamine and 450 mg of potassium carbonate were stirred at room temperature in 10 ml of water for three days. The thus-obtained crude product was thereupon chromatographed on LiChroprep RP-18 silica gel with water and subsequently with water containing an increasing amount of methanol. The relevant fractions were lyophilized; N,N',N"-(1,3,5-triazine-2,4,6-triyl)-tris-(1-amino-1-desoxy-D-glucitol) was thus obtained as a colorless powder, MS: m/z 619.2 ([M+H]$^+$).

B. The N,N',N"-(1,3,5-triazine-2,4,6-triyl)-tris-(1-amino-1-desoxy-D-glucitol) obtained above was converted analogously to Example 1.b. into N,N',N"-(1,3,5-triazine-2,4,6-triyl)-tris-(1-amino-1-desoxy-2,3,4,5,6-penta-O-sulfo-D-glucitol) pentadecasodium salt, [a]–1.4° (c 0.9; water), MS: m/z 2126.0 (reconstructed M), (tetradecasodium salt monosulfonic acid).

EXAMPLE 3

A. 2.5 g of 2,3:4,5-di-O-isopropylidene-1,6-bis-O-(4-methyl-phenylsulfonyl)-galactitol (E.P. 56575 A1, Bayer AG/CA 98(7)(1982):54399d), 2.4 g of methyl (E)-3-(4-hydroxy-phenyl)-acrylate and 1.85 g of finely ground anhydrous potassium carbonate were suspended in 30 ml of dimethylformamide and stirred at 130° C. under argon for 18 hours. The reaction mixture was subsequently diluted with water. The crystals formed were filtered off and subsequently chromatographed on silica gel with 5% ether in methylene chloride. 2,3:4,5-Di-O-isopropylidene-1,6-bis-O-[(E)-4-(2-methoxycarbonyl-vinyl)-phenyl]-galactitol was thus obtained in the form of colorless crystals. MS: m/z 582 ([M]$^+$).

B. 1.89 g of 2,3:4,5-di-O-isopropylidene-1,6-bis-O-[(E)-4-(2-methoxycarbonyl-vinyl)-phenyl]-galactitol, 30 ml of methanol and 30 ml of concentrated aqueous sodium hydroxide solution were heated under reflux at 110° C. for 18 hours. Thereupon, the majority of the methanol was distilled off under reduced pressure. The residue was diluted with ice-water and acidified with 1N aqueous hydrochloric acid. The crystals thereby formed were filtered off and gave 1,6-bis-O-[4-[(E)-2-carboxy-vinyl]-phenyl]-2,3:4,5-di-O-isopropylidene-galactitol in the form of colorless crystals, MS: m/z 554 ([M]$^+$).

C. 0.28 g of 1,6-bis-O-[4-[(E)-2-carboxy-vinyl]-phenyl]-2,3:4,5-di-O-isopropylidene-galactitol in 5 ml of dimethylformamide was treated with 0.1 ml of 4-methylmorpholine at 0°–5° C. with the exclusion of moisture and stirred intensively for 10 minutes. Thereupon, 0.20 g of solid 2-chloro-4,6-dimethoxy-1,3,5-triazine was added and the mixture was stirred at 0°–5° C. for a further 2 hours. Subsequently, 0.19 g of D-glucamine was added and the mixture was stirred at room temperature for a further 18 hours. Thereupon, the reaction mixture was diluted several times with water and evaporated at 40°–50° C. under reduced pressure, the residue was treated with 6 ml of water and 0.5 ml of triethylamine and the mixture was heated and filtered; there was thus obtained 1,6-bis-[4-[(E)-2-D-glucit-1-ylcarbamoyl-vinyl]-phenyl]-2,3:4,5-di-O-isopropylidene-galactitol as a colorless powder, MS: m/z 881.6 ([M+H]$^+$).

D. 1.0 g of 1,6-bis-[4-[(E)-2-D-glucit-1-ylcarbamoyl-vinyl]-phenyl]-2,3:4,5-di-O-isopropylidene-galactitol was suspended in 17 ml of dioxan, 2 ml of trifluoroacetic acid and 5 ml of water and heated under reflux at 110° C. for 4 hours. Thereupon, the reaction mixture was concentrated to dryness; 1,6-bis-[(E)-4-(2-D-glucit-1-ylcarbamoylvinyl)-phenyl]-galactitol thereby resulted as a colorless solid which was used directly in the next step.

E. The 1,6-bis-[(E)-4-(2-D-glucit-1-ylcarbamoyl-vinyl)-phenyl]-galactitol obtained above was converted analogously to Example 1.B. into 1,6-bis-[4-[(E)-2-(2,3,4,5,6-penta-O-sulfo-D-glucit-1-ylcarbamoyl)-vinyl]-phenyl]-2,3,4,5-tetra-O-sulfo-galactitol tetradecasodium salt, [a]–1.7° (c 0.7; water), MS: m/z 2229.0 (reconstructed M).

EXAMPLE 4

A. 0.69 g of methyl 4'-hydroxy-biphenyl-4-carboxylate and 0.44 g of finely ground potassium carbonate suspended in 2.5 ml of dimethylformamide were treated with 0.54 g of 3,4-O-methoxymethylene-2,5-O-methylene-1,6-bis-O-(4-methyl-phenylsulfonyl)-D-mannitol (B. Lamm et al., Acta Chem. Scand. B 41, 202 (1987)). The reaction mixture was stirred at 130° C. under argon for 18 hours. The reaction solution was subsequently poured into water. The precipitate which separated was filtered off and chromatographed on silica gel with methylene chloride/methanol. There was thus obtained 1,6-bis-O-(4'-methoxycarbonyl-biphenyl-4-yl)-3,4-O-methoxymethylene-2,5-O-methylene-D-mannitol as a colorless solid, MS: m/z 656 ([M]$^+$).

B. 1.0 g of 1,6-bis-O-(4'-methoxycarbonyl-biphenyl-4-yl)-3,4-O-methoxymethylene-2,5-O-methylene-D-mannitol dissolved in 20 ml of methanol was treated with 6 ml of conc. sulfuric acid and heated under reflux for 16 hours. The reaction mixture was subsequently poured into water and the separated crystals were filtered off. There was thus obtained 1,6-bis-O-(4'-methoxy-carbonyl-biphenyl-4-yl)-2,5-O-methylene-D-mannitol as a colorless solid, MS: m/z 614 ([M]$^+$).

C. 0.67 g of 1,6-bis-O-(4'-methoxycarbonyl-biphenyl-4-yl)-2,5-O-methylene-D-mannitol was heated under reflux for 16 hours in 15 ml of concentrated sodium hydroxide solution and 15 ml of methanol; thereupon the mixture was evaporated and the residue was acidified with dilute hydrochloric acid. The precipitate of 1,6-bis-O-(4'-carboxy-biphenyl-4-yl)-2,5-O-methylene-D-mannitol which thereby formed was filtered off, dissolved in 5 ml of acetic anhydride and 5 ml of pyridine and stirred at room temperature for 16 hours. Now, the mixture was again evaporated, the residue was poured into dilute hydrochloric acid and the mixture was filtered; there was thus obtained 3,4-di-O-acetyl-1,6-bis-O-(4'-carboxy-biphenyl-4-yl)-2,5-O-methylene-D-mannitol in the form of colorless crystals, MS: m/z 669.4 ([M–H]$^-$).

D. 0.78 g of 3,4-di-O-acetyl-1,6-bis-O-(4'-carboxy-biphenyl-4-yl)-2,5O-methylene-D-mannitol in 15 ml of dimethylformamide was treated with 0.26 ml of 4-methylmorpholine at 0°–5° C. with the exclusion of moisture and stirred intensively for 10 minutes. Thereupon, 0.47 g of solid 2-chloro-4,6-dimethoxy-1,3,5-triazine was added and the reaction mixture was stirred at 0°–5° C. for a further 2 hours. Subsequently, 0.49 g of D-glucamine was added and the reaction mixture was stirred at room temperature for a further 18 hours. Thereupon, the mixture was diluted several times with water and evaporated at 40°–50° C. under reduced pressure, the residue was treated with 15 ml of pyridine and 15 ml of acetic anhydride and the mixture was stirred for a further 18 hrs. Then, the reaction mixture was again concentrated and the residue was treated with ice-water and 1N hydrochloric acid. The thus-obtained precipitate was filtered off and dissolved in methylene chloride, the solution was washed with water, dried over magnesium sulfate and concentrated, and the residue was chromatographed on silica gel with methylene chloride/methanol. There was thus obtained 3,4-di-O-acetyl-1,6-bis-[4'-(2,3,4,5,6-penta-O-acetyl-D-glucit-1-ylcarbamoyl)-biphenyl-4-yl]-2,5-O-methylene-D-mannitol as a colorless solid, MS: m/z 1417.4 ([M+H]$^+$).

E. 1.2 g of 3,4-di-O-acetyl-1,6-bis-[4'-(2,3,4,5,6-penta-O-acetyl-D-glucit-1-ylcarbamoyl)-biphenyl-4-yl]-2,5-O-methylene-D-mannitol were dissolved in 25 ml of methanol and 5 ml of tetrahydrofuran and treated with 1.2 ml of 1 molar sodium methylate solution in methanol. The reaction mixture was stirred at room temperature for 2.5 hours. The precipitate which thereby formed was filtered off and washed with methanol. There was thus obtained 1,6-bis-O-(4'-D-glucit-1-ylcarbamoyl-biphenyl-4-yl)-2,5-O-methylene-D-mannitol in the form of colorless crystals and was used directly in the following reaction step.

F. The 1,6-bis-O-(4'-D-glucit-1-ylcarbamoyl-biphenyl-4-yl)-2,5-O-methylene-D-mannitol obtained above was converted analogously to Example 1.B. into 1,6-bis-[4'-(2,3,4,5,6-penta-O-sulfo-D-glucit-1-ylcarbamoyl)-biphenyl-4-yl]-2,5-O-methylene-3,4-di-O-sulfo-D-mannitol dodecasodium salt, [a]–7.6° (c 0.7; water), MS: m/z 2137.0 (reconstructed M).

EXAMPLE 5

A. 2.92 g of methyl 4'-hydroxy-biphenyl-4-carboxylate and 1.77 g of finely ground potassium carbonate suspended in 25 ml of dimethylformamide were treated with 2,0 g of 2,3-O-isopropylidene-1,4-bis-O-(4-methyl-phenylsulfonyl)-L-threitol. The reaction mixture was stirred at 130° C. under argon for 18 hours. The reaction solution was subsequently poured on to ice-water and the separated precipitate was filtered off and chromatographed on silica gel with methylene chloride/methanol. There was thus obtained 2,3-O-isopropylidene-1,4-bis-O-(4'-methoxycarbonyl-biphenyl-4-yl)-L-threitol as a colorless solid, MS: m/z 582 ([M]$^+$).

B. 1.77 g of 2,3-O-isopropylidene-1,4-bis-O-(4'-methoxycarbonyl-biphenyl-4-yl)-L-threitol were heated under reflux for 18 hours in 40 ml of methanol and 40 ml of concentrated sodium hydroxide solution. Subsequently, the methanol was distilled off. The residue was treated with ice-water, acidified and the precipitate formed was filtered off; there was thus obtained 1,4-bis-O-(4'-carboxy-biphenyl-4-yl)-2,3-O-isopropylidene-L-threitol as a colorless solid, MS: m/z 554 ([M]$^+$).

C. 1.5 g of 1,4-bis-O-(4'-carboxy-biphenyl-4-yl)-2,3-O-isopropylidene-L-threitol in 30 ml of dimethylformamide were treated with 0.6 ml of 4-methylmorpholine at 0°–50° C. with the exclusion of moisture and stirred intensively for 10 minutes. Thereupon, 1.04 g of solid 2-chloro-4,6-dimethoxy-1,3,5-triazine were added and the mixture was stirred at 0°–5° C. for a further 2 hours. Subsequently, 1.07 g of D-glucamine were added and the mixture was stirred at room temperature for a further 18 hours. Thereupon, the reaction mixture was diluted several times with water and evaporated at 40°–50° C. under reduced pressure, the residue was treated with 1 ml of triethylamine and 5 ml of water, the mixture was boiled briefly and the insoluble precipitate was filtered off. There was thus obtained 1,4-bis-O-(4'-D-glucit-1-ylcarbamoyl-biphenyl-4-yl)-2,3-O-isopropylidene-L-threitol as a colorless solid, MS: m/z 881.2 ([M+H]$^+$).

D. 1.0 g of 1,4-bis-O-(4'-D-glucit-1-ylcarbamoyl-biphenyl-4-yl)-2,3-O-isopropylidene-L-threitol was suspended in 15 ml of dioxan, 1.5 ml of trifluoroacetic acid and 5 ml of water and heated under reflux at 110° C. for 4 hours. The reaction mixture was subsequently concentrated to dryness. There was thus obtained 1,4-bis-O-(4'-D-glucit-1-ylcarbamoyl-biphenyl-4-yl)-L-threitol as a colorless solid, MS: m/z 841.6 ([M+H]$^+$).

E. The 1,4-bis-O-(4'-D-glucit-1-ylcarbamoyl-biphenyl-4-yl)-L-threitol obtained above was converted analogously to Example 1.B into 1,4-bis-O-[4-(2,3,4,5,6-penta-O-sulfo-D-glucit-1-ylcarbamoyl)-biphenyl-4-yl]-2,3-di-O-sulfo-L-threitol dodecasodium salt, [a]+0.85° (c 0.7; water), MS: m/z 2065.0 (reconstructed M).

EXAMPLE 6

A. 0.6 g of 1,6-bis-O-[4-[(E)-2-(2,3,4,5,6-penta-O-sulfo-D-glucit-1-ylcarbamoyl)-vinyl]-phenyl]-2,3,4,5-tetra-O-sulfo-galactitol tetradecasodium salt (Example 3.E.) were exhaustively hydrogenated in 9 ml of distilled water with the addition of 80 mg of palladium on charcoal (10%) in a hydrogen atmosphere. Subsequently, the reaction mixture was filtered over a 0.8μ cellulose filter and the filtrate was lyophilized; there was thus obtained 1,6-bis-O-[4-[2-(2,3,4,5,6-penta-O-sulfo-D-glucit-1-ylcarbamoyl)-ethyl]-phenyl]-2,3,4,5-tetra-O-sulfo-galactitol tetrasodium salt, [a]–3.2° (c 0.7; water), MS: m/z 2233.0 (reconstructed M).

EXAMPLE 7

A. 2.0 g of 2,3-O-isopropylidene-1,4-bis-O-(4-methyl-phenyl-sulfonyl)-L-threitol, 2.3 g of methyl (E)-3-(4-hydroxy-phenyl)-acrylate and 1.77 g of finely ground anhydrous potassium carbonate were suspended in 30 ml of dimethylformamide. The reaction mixture was stirred at 130° C. under argon for 18 hours. Subsequently, the reaction mixture was diluted with water and extracted with methylene chloride. The combined methylene chloride phases were dried over magnesium sulfate and concentrated. The residue was chromatographed on silica gel with 5% ether in methylene chloride. There was thus obtained 2,3-O-isopropylidene-1,4-bis-[4-[(E)-2-methoxycarbonyl-vinyl]-phenyl]-L-threitol in the form of colorless crystals, MS: m/z 482 ([M]$^+$).

B. 0.24 g of 2,3-O-isopropylidene-1,4-bis-[4-[(E)-2-methoxy-carbonyl-vinyl]-phenyl]-L-threitol was stirred at room temperature in 2 ml of acetonitrile and 3 ml of 2N sodium hydroxide solution for 70 hours. The acetonitrile was subsequently distilled off. The residue was treated with ice-water, acidified and the precipitate formed was filtered off. There was thus obtained 1,4-O-bis-[4-[(E)-2-carboxy-vinyl]-phenyl]-2,3-O-isopropylidene-L-threitol as a colorless solid, MS: m/z 454 ([M]$^+$).

C. 1.0 g of 1,4-O-bis-[4-[(E)-2-carboxy-vinyl]-phenyl]-2,3-O-isopropylidene-L-threitol in 20 ml of dimethylformamide was treated with 0.5 ml of 4-methylmorpholine at 0°–5° C. with the exclusion of moisture and stirred intensively for 10 minutes. Thereupon, 0.85 g of solid 2-chloro-4,6-dimethoxy-1,3,5-triazine was added and the mixture was stirred at 0°–5° C. for a further 2 hours. Subsequently, 0.87 g of D-glucamine was added and the mixture was stirred at room temperature for a further 18 hours. Thereupon, the reaction mixture was diluted several times with water and evaporated at 40°–50° C. under reduced pressure, the residue was treated with 17 ml of pyridine and 17 ml of acetic anhydride and the mixture was stirred for a further 18 hours. Then, the reaction mixture was again concentrated, the residue was treated with ice-water and 1N hydrochloric acid and the mixture was extracted with methylene chloride. The combined methylene chloride phases were dried over magnesium sulfate and concentrated, and the residue was chromatographed on silica gel with methylene chloride/methanol. The product fraction was dissolved in 30 ml of methanol and 7 ml of tetrahydrofuran, the solution was treated with 2 ml of 1 molar sodium methylate solution in methanol and the mixture was stirred at room temperature for 18 hours. The precipitate which thereby formed was filtered off after the addition of a small amount of acetic acid and partial distillation of the methanol. There was thus obtained 1,4-bis-O-[4-[(E)-2-D-glucit-1-ylcarbamoyl-vinyl]-phenyl]-2,3-O-isopropylidene-L-threitol as a colorless solid, MS: m/z 781.5 ([M+H]$^+$).

D. 0.33 g of 1,4-bis-O-[4-[(E)-2-D-glucit-1-ylcarbamoyl-vinyl]-phenyl]-2,3-O-isopropylidene-L-threitol was suspended in 5 ml of dioxan, 1 ml of trifluoroacetic acid and 1.5 ml of water and heated under reflux at 110° C. for 1.5 hours. The reaction mixture was subsequently concentrated to dryness. There was thus obtained 1,4-bis-O-[4-[(E)-2-D-glucit-1-ylcarbamoyl-vinyl]-phenyl]-L-threitol as a colorless solid, MS: m/z 741.6 ([M+H]$^+$).

E. The 1,4-bis-O-[4-[(E)-2-D-glucit-1-ylcarbamoyl-vinyl]-phenyl]-L-threitol obtained above was converted analogously to Example 1.B. into 1,4-bis-O-[4-[(E)-2-(2,3,4,5,6-penta-O-sulfo-D-glucit-1-ylcarbamoyl)-vinyl]-phenyl]-2,3-di-O-sulfo-L-threitol dodecasodium salt, [a]–0.86° (c 0.7; water), MS: m/z 1966.0 (reconstructed M).

EXAMPLE 8

A. 0.2 g of 1,4-bis-O-[4-[(E)-2-(2,3,4,5,6-penta-O-sulfo-D-glucit-1-ylcarbamoyl)-vinyl]-phenyl]-2,3-di-O-sulfo-L-threitol dodecasodium salt was exhaustively hydrogenated in 10 ml of distilled water with the addition of 40 mg of palladium on charcoal (10%) in a hydrogen atmosphere. Subsequently, the reaction mixture was filtered over a 0.8μ cellulose filter and the filtrate was lyophilized; there was thus obtained 1,4-bis-O-[4-[2-(2,3,4,5,6-penta-O-sulfo-D-glucit-1-ylcarbamoyl)-ethyl]-phenyl]-di-O-sulfo-L-threitol dodecasodium salt, [a]–0.17°(c 0.6; water), MS: m/z 1970.0 (reconstructed M).

EXAMPLE 9

A. A solution of 4.91 g of (4-methoxycarbonyl-benzyl)-triphenylphosphonium bromide in 50 ml of tetrahydrofuran was treated at 0°–5° C. with the exclusion of moisture and under argon with 1.91 g of 4-benzyloxy-benzaldehyde and subsequently slowly with 10 ml of 1N sodium methylate solution in methanol. After stirring at room temperature for 30 minutes, the reaction mixture was filtered over Dicalite and concentrated, and the residue was chromatographed on silica gel with hexane/ethyl acetate (3:1). There was thus obtained methyl (Z)-4-[2-(4-benzyloxy-phenyl)-vinyl]-benzoate as a yellowish solid, MS: m/z 344 ([M]$^+$).

B. 1.5 g of (Z)-4-[2-(4-benzyloxy-phenyl)-vinyl]-benzoate were exhaustively hydrogenated in 20 ml of methanol and 20 ml of ethyl acetate with the addition of 150 mg of palladium on charcoal (10%) in a hydrogen atmosphere. The reaction mixture was subsequently filtered over a 0.8μ cellulose filter and the filtrate was concentrated; there was thus obtained methyl 4-[2-(4-hydroxy-phenyl)-ethyl]-benzoate as a colorless solid, MS: m/z 256 ([M]$^+$).

C. 0.71 g of 2,3-O-isopropylidene-1,4-bis-O-(4-methyl-phenylsulfonyl)-L-threitol, 1.0 g of methyl 4-[2-(4-hydroxy-phenyl)-ethyl]-benzoate and 0.54 g of finely ground anhydrous potassium carbonate were suspended in 20 ml of dimethylformamide and stirred at 130° C.

under argon for 18 hours. Subsequently, the reaction mixture was diluted with water and extracted with ethyl acetate. The combined ethyl acetate phases were dried over magnesium sulfate and concentrated. The residue was chromatographed on silica gel with 5% ether in methylene chloride. There was thus obtained 2,3-O-isopropylidene-1,4-bis-O-[4-[2-(4-methoxycarbonyl-phenyl)-ethyl]-phenyl]-L-threitol in the form of colorless crystals, MS: m/z 638 ([M]$^+$).

D. 0.7 g of 2,3-O-isopropylidene-1,4-bis-O-[4-[2-(4-methoxycarbonyl-phenyl)-ethyl]-phenyl]-L-threitol was stirred under reflux for 18 hours in 20 ml of methanol and 20 ml of concentrated sodium hydroxide solution. The methanol was subsequently distilled off. The residue was treated with ice-water, acidified with dilute hydrochloric acid and the precipitate formed was filtered off; there was thus obtained 1,4-bis-O-[4-[2-(4-carboxy-phenyl)-ethyl]-phenyl]-2,3-O-isopropylidene-L-threitol as a colorless solid, MS: m/z 609.4 ([M–H]$^-$).

E. 0.52 g of 1,4-bis-O-[4-[2-(4-carboxyphenyl)-ethyl]-phenyl]-2,3-O-isopropylidene-L-threitol in 10 ml of dimethylformamide was treated with 0.21 ml of 4-methylmorpholine at 0°–5° C. with the exclusion of moisture and stirred intensively for 10 minutes. Thereupon, 0.33 g of solid 2-chloro-4,6-dimethoxy-1,3,5-triazine was added and the mixture was stirred at 0°–5° C. for a further 2 hours. Subsequently, 0.34 g of D-glucamine was added and the mixture was stirred at room temperature for a further 18 hours. Thereupon, the reaction mixture was diluted with water and concentrated, the residue was treated with 10 ml of water and 0.5 ml of triethylamine and the mixture was boiled briefly and filtered. The residue which was thereby obtained was triturated in 20 ml of methanol and 20 ml of methylene chloride and again filtered. There was thus obtained 1,4-bis-O-[4-[2-(4-D-glucit-1-ylcarbamoyl-phenyl)-ethyl]-phenyl]-2,3-O-isopropylidene-L-threitol as a colorless solid, MS: m/z 959.6 ([M+Na]$^+$).

F. 0.52 g of 1,4-bis-O-[4-[2-(4-D-glucit-1-ylcarbamoyl-phenyl)-ethyl]-phenyl]-2,3-O-isopropylidene-L-threitol was suspended in 7 ml of dioxan, 2 ml of trifluoroacetic acid and 3 ml of water and heated under reflux at 110° C. for 18 hours. Subsequently, the reaction mixture was concentrated to dryness, the residue was treated with 6 ml of acetic anhydride and 6 ml of pyridine and the mixture was stirred at room temperature for 18 hours. Then, the reaction mixture was again concentrated and the residue was treated with ice-water and 1N hydrochloric acid. The precipitate which thereby formed was filtered off and chromatographed on silica gel with methylene chloride/isopropanol. There was thus obtained 2,3- di-O-acetyl-1,4-bis-O-[4-[2-[4-(2,3,4,5,6-penta-O-acetyl-D-glucit-1-ylcarbamoyl)-phenyl]-ethyl]-phenyl]-L-threitol as a colorless solid, MS: m/z 1424.9 ([M+Na]$^+$).

G. 0.36 g of 2,3-di-O-acetyl-1,4-bis-O-[4-[2-[4-(2,3,4,5,6-penta-O-acetyl-D-glucit-1-ylcarbamoyl)-phenyl]-ethyl]-phenyl]-L-threitol was dissolved in 5 ml of ethanol and 5 ml of tetrahydrofuran, treated with 0.4 ml of 1 molar sodium methylate solution in methanol and stirred at room temperature for 18 hours. The precipitate which thereby formed was filtered off. There was thus obtained 1,4-bis-O-[4-[2-(4-D-glucit-1-ylcarbamoyl-phenyl)-ethyl]-phenyl]-L-threitol as a colorless solid, MS: m/z 919.3 ([M+Na]$^+$).

H. The 1,4-bis-O-[4-[2-(4-D-glucit-1-ylcarbamoyl-phenyl)-ethyl]-phenyl]-L-threitol obtained above was converted analogously to Example 1.B. into 1,4-bis-O-[4-[2-[4-(2,3,4,5,6-penta-O-sulfo-D-glucit-1-ylcarbamoyl)-phenyl]-ethyl]-phenyl]-2,3-di-O-sulfo-L-threitol dodecasodium salt, [a]–0.57° (c 0.7; water).

EXAMPLE 10

A. 1,4-Bis-O-(4'-D-glucit-1-ylcarbamoyl-biphenyl-4-yl)-D-threitol was obtained as a colorless solid, MS: m/z 864.6 ([M+Na]+), analogously to Example 5.A.–D. from methyl 4'-hydroxy-biphenyl-4-carboxylate and 2,3-O-isopropylidene-1,4-bis-O-(4-methyl-phenylsulfonyl)-D-threitol in place of 2,3-O-isopropylidene-1,4-bis-O-(4-methylphenylsulfonyl)-L-threitol via the following intermediates:

2,3-O-Isopropylidene-1,4-bis-O-(4'-methoxycarbonyl-biphenyl-4-yl)-D-threitol, colorless solid, MS: m/z 582 ([M]$^+$);

1,4-bis-O-(4'-carboxy-biphenyl-4-yl)-2,3-O-isopropylidene-D-threitol, colorless solid, MS: m/z 553.5 ([M–H]$^-$);

1,4-bis-O-(4'-D-glucit-1-ylcarbamoyl-biphenyl-4-yl)-2,3-O-isopropylidene-D-threitol, colorless solid, MS: m/z 881.5 ([M+H]$^+$).

B. The 1,4-bis-O-(4'-D-glucit-1-ylcarbamoyl-biphenyl-4-yl)-D-threitol obtained above was converted analogously to Example 1.B. into 1,4-bis-O-[4-(2,3,4,5,6-penta-O-sulfo-D-glucit-1-ylcarbamoyl)-biphenyl-4-yl]-2,3-di-O-sulfo-D-threitol dodecasodium salt, [a]–9.80° (c 0.8; water), MS: m/z 2066.0 (reconstructed M).

EXAMPLE 11

A. 1,6Bis-O-[4-[2-(4-D-glucit-1-ylcarbamoyl-phenyl)-ethyl]-phenyl]-galactitol was obtained as a colorless solid, MS: m/z 979.5 ([M+Na]$^+$), analogously to Example 9.C.–9.G. from methyl 4-[2-(4-hydroxy-phenyl)-ethyl]-benzoate and 2,3:4,5-di-0-isopropylidene-1,6-bis-O-(4-methyl-phenylsulfonyl)-galactitol in place of 2,3-O-isopropylidene-1,4-bis-O-(4-methyl-phenylsulfonyl)-L-threitol via the following intermediates:

2,3:4,5-Di-O-isopropylidene-1,6-bis-O-[4-[2-(4-methoxycarbonyl-phenyl)-ethyl]-phenyl]-galactitol, colorless solid, MS: m/z 738 ([M]$^+$);

1,6-bis-O-[4-[2-(4-carboxy-phenyl)-ethyl]-phenyl]-2,3:4,5-di-O-isopropylidene-galactitol, colorless solid, MS: m/z 709.4 ([M–H]$^-$);

1,6-bis-O-[4-[2-(4-D-glucit-1-ylcarbamoyl-phenyl)-ethyl]-phenyl]-2,3:4,5-di-O-isopropylidene-galactitol, colorless solid, MS: m/z 1037.6 ([M+H]$^+$);

2,3,4,5-tetra-O-acetyl-1,6-bis-O-[4-[2-[4-(2,3,4,5,6-penta-O-acetyl-D-glucit-1-ylcarbamoyl)-phenyl]-ethyl]-phenyl]-galactitol, colorless solid, MS: m/z 773.8 ([M+2H]$^{2+}$).

B. The 1,6-bis-O-[4-[2-(4-D-glucit-1-ylcarbamoyl-phenyl)-ethyl]-phenyl]-galactitol obtained above was converted analogously to Example 1.B. into 1,6-bis-O-[4-[2-[4-(2,3,4,5,6-penta-O-sulfo-D-glucit-1-ylcarbamoyl)-phenyl]-ethyl]-phenyl]-2,3,4,5-tetra-O-sulfo-galactitol tetradecasodium salt, [a]–3.3° (c 0.6; water), MS: m/z 2385.0 (reconstructed M).

EXAMPLE 12

A. 1.33 g of 2,3:4,5-di-O-isopropylidene-1,6-bis-O-(4-methyl-phenylsulfonyl)-galactitol, 1.6 g of methyl 4'-hydroxy-biphenyl-4-carboxylate and 0.97 g of finely ground anhydrous potassium carbonate were suspended in 20 ml of dimethylformamide and stirred at 130° C. for 18 hours under argon. The reaction mixture was subsequently diluted with water and the thus-formed crystals were filtered off. There was thus obtained 2,3:4,5-di-O-isopropylidene-1,6-bis-(4'-methoxycarbonyl-biphenyl-4-yl)-galactitol in the form of colorless crystals, MS: m/z 682 ([M]$^+$).

B. 1.2 g of 2,3:4,5-di-O-isopropylidene-1,6-bis-(4'-methoxy-carbonyl-biphenyl-4-yl)-galactitol, 25 ml of methanol and 25 ml of concentrated aqueous sodium hydroxide solution were heated under reflux at 110° C. for 18 hours. Thereupon, the majority of the methanol was distilled off under reduced pressure, the residue was diluted with ice-water, acidified with dilute aqueous hydrochloric acid and the crystals which thereby formed were filtered off. There was thus obtained 1,6-bis-(4'-carboxy-biphenyl-4-yl)-2,3:4,5-di-O-isopropylidene-galactitol in the form of colorless crystals, MS: m/z 653.5 ([M–H]$^-$).

C. 1.0 g of 1,6-bis-(4'-carboxy-biphenyl-4-yl)-2,3:4,5-di-O-isopropylidene-galactitol was suspended in 17 ml of dioxan, 4 ml of trifluoroacetic acid and 5 ml of water and heated under reflux at 110° C. for 17 hours. Thereupon, the reaction mixture was concentrated, and the residue was treated with methanol and filtered. There was thus obtained 1,6-bis-(4'-carboxy-biphenyl-4-yl)-galactitol as a colorless solid, elementary analysis calculated for $C_{32}H_{30}O_{10}$x0.31$H_2O$: C=66.25%, H =5.32%: found: C=66.12%, H=5.24%.

D. 0.8 g of 1,6-bis-(4'-carboxy-biphenyl-4-yl)-galactitol was stirred at 100° C. for 5 hours in a mixture of 20 ml of acetic anhydride and 20 ml of pyridine. Thereupon, the reaction mixture was concentrated, the residue was treated with ice-water and dilute hydrochloric acid and the thus-formed precipitate was filtered off. There was thus obtained 2,3,4,5-tetra-O-acetyl-1,6-bis-O-(4'-carboxy-biphenyl-4-yl)-galactitol as a colorless solid, MS: m/z 741.4 ([M–H]$^-$).

E. 0.84 g of 2,3,4,5-tetra-O-acetyl-1,6-bis-O-(4'-carboxy-biphenyl-4-yl)-galactitol in 20 ml of dimethylformamide was treated with 0.3 ml of 4-methylmorpholine at 0°–5° C. with the exclusion of moisture and stirred intensively for 10 minutes. Thereupon, 0.44 g of solid 2-chloro-4,6-dimethoxy-1,3,5-triazine was added and the mixture was stirred at 0°–5° C. for a further 2 hours. Subsequently, 0.45 g of D-glucamine was added and the mixture was stirred at room temperature for a further 18 hours. Thereupon, the reaction mixture was diluted several times with water and evaporated at 40°–50° C. under reduced pressure, the residue was treated with 12 water and 0.5 ml of triethylamine and the mixture was heated and filtered. For further purification, the thus-obtained crude 2,3,4,5-tetra-O-acetyl-1,6-bis-O-(4'-D-glucit-1-ylcarbamoyl-biphenyl-4-yl)-galactitol was treated with 10 ml of pyridine and 10 ml of acetic anhydride and stirred at room temperature for 24 hours. Then, this reaction mixture was concentrated, the residue was treated with ice-water and 1N hydrochloric acid and the mixture was extracted with methylene chloride. The combined methylene chloride phases were dried over magnesium sulfate, concentrated and the residue was chromatographed on silica gel with methylene chloride/isopropanol. There was obtained 2,3,4,5-tetra-O-acetyl-1,6-bis-O-[4'-(2,3,4,5,6-penta-O-acetyl-D-glucit-1-ylcarbamoyl)-biphenyl-4-yl]-galactitol as a colorless solid, MS: m/z 1489.4 ([M+H]$^+$).

F. 0.6 g of 2,3,4,5-tetra-O-acetyl-1,6-bis-O-[4'-(2,3,4,5,6-penta-O-acetyl-D-glucit-1-ylcarbamoyl)-biphenyl-4-yl]-galactitol was dissolved in 5 ml of methanol and 5 ml of tetrahydrofuran, treated with 0.4 ml of 1 molar sodium methylate solution in methanol and stirred at 60° C. for 2 hours and at room temperature for 18 hours. The precipitate which thereby formed was filtered off. There was obtained 1,6-bis-O-(4'-D-glucit-1-ylcarbamoyl-biphenyl-4-yl)-galactitol as a colorless solid, MS: m/z 923.2 ([M+Na]$^+$).

G. The 1,6-bis-O-(4'-D-glucit-1-ylcarbamoyl-biphenyl-4-yl)-galactitol obtained above was converted analogously to Example 1.B. into 1,6-bis-O-[4'-(2,3,4,5,6-penta-O-sulfo-D-glucit-1-ylcarbamoyl)-biphenyl-4-yl]-2,3,4,5-tetra-O-sulfo-galactitol tetradecasodium salt, [a]–2.4° (c 0.7; water), MS: m/z 2330.0 (reconstructed M).

EXAMPLE 13

A. 1,4-Bis-O-(3-D-glucit-1-ylcarbamoyl-naphthalen-2-yl)-L-threitol was obtained as a colorless solid, MS: m/z 789.7 ([M+H]$^+$), analogously to Example 5.A.–D. from methyl 3-hydroxy-naphthalene-2-carboxylate and 2,3-O-isopropylidene-1,4-bis-O-(4-methyl-phenylsulfonyl)-L-threitol via the following intermediates:

2,3-0-isopropylidene-1,4-bis-O-(3- methoxycarbonyl-naphthalen-2-yl)-L-threitol, colorless solid, MS: m/z 530 ([M]$^+$);

1,4-bis-O-(3-carboxy-naphthalen-2-yl)-2,3-O-isopropylidene-L-threitol, colorless solid, MS: m/z 501.4 ([M–H]$^-$);

1,4-bis-O-(3-D-glucit-1-ylcarbamoyl-naphthalen-2-yl)-2,3-O-isopropylidene-L-threitol, colorless solid, MS: m/z 830.0 ([M+H]$^+$).

B. The 1,4-bis-O-(3-D-glucit-1-ylcarbamoyl-naphthalen-2-yl)-L-threitol obtained above was converted analogously to Example 1.B. into 1,4-bis-O-[3-(2,3,4,5,6-penta-O-sulfo-D-glucit-1-ylcarbamoyl)-naphtalen-2-yl]-2,3-di-O-sulfo-L-threitol dodecasodium salt, [a]–3.9° (c 0.7; water), MS: m/z 2013.5 (reconstructed M).

EXAMPLE 14

A. 1,6-Bis-O-(3-D-glucit-1-ylcarbamoyl-naphthalen-2-yl)-galactitol was obtained as a colorless solid, MS: m/z 849.7 ([M+H]$^+$), analogously to Example 12.A.-F. from methyl 3-hydroxy-naphthalene-2-carboxylate and 2,3:4,5-di-O-isopropylidene-1,6-bis-O-(4-methyl-phenylsulfonyl)-galactitol via the following intermediates:

2,3:4,5-Di-O-isopropylidene-1,6-bis-O-(2-methoxycarbonyl-naphthalen-2-yl)-galactitol, yellowish solid, MS: m/z 630 ([M]$^+$);

1,6-bis-O-(3-carboxy-naphthalen-2-yl)-2,3:4,5-di-O-isopropylidene-galactitol, colorless solid, MS: m/z 601.3 ([M–H]$^-$);

1,6-bis-O-(3-carboxy-naphthalen-2-yl)-galactitol, colorless solid, MS: m/z 545.3 ([M+Na]$^+$);

2,3,4,5-tetra-O-acetyl-1,6-bis-O-(3-carboxy-naphthalen-2-yl)-galactitol, colorless solid, MS: m/z 713.4 ([M+Na]$^+$);

2,3,4,5-tetra-O-acetyl-1,6-bis-O-(3-D-glucit-1-ylcarbamoyl-naphthalen-2-yl)-galactitol, colorless solid, MS: m/z 1017.6 ([M+H]$^+$).

B. The 1,6-bis-O-(3-D-glucit-1-ylcarbamoyl-naphthalen-2-yl)-galactitol obtained above was converted analogously to Example 1.B. into 1,6-bis-O-[3-(2,3,4,5,6-penta-O-sulfo-D-glucit-1-ylcarbamoyl)-naphthalen-2-yl]-2,3,4,5-tetra-O-sulfo-galactitol tetradecasodium salt, [a]–6.3° (c 0.7; water), MS: m/z 2277.5 (reconstructed M).

EXAMPLE 15

A. 0.4 g of bis-(4-hydroxy-phenyl)-methane dissolved in 8 ml of acetonitrile was treated under argon with 0.3 g of powdered potassium carbonate and 0.4 g of tert.-butyl bromoacetate and stirred at room temperature for 2.5 hours. Subsequently, a further 0.13 g of tert.-butyl bromoacetate was added and the mixture was stirred at room temperature for 70 hours. Thereupon, the reaction mixture was concentrated and the residue was chromatographed on silica gel with methylene chloride/ether (95:5); there was thus obtained tert.-butyl 4-(4-hydroxy-benzyl)-phenoxyacetate as a colorless solid, MS: m/z 314 ([M]$^+$).

B. 1,4-Bis-O-[4-(4-D-glucit-1-ylcarbamoylmethoxy-benzyl)-phenyl]-L-threitol was obtained as a colorless solid, MS: m/z 952.4 ([M+Na]$^+$), analogously to Example 12.A.-F. from tert.-butyl 4-(4-hydroxy-benzyl)-phenoxyacetate and 2,3-O-isopropylidene-1,4-di-O-(4-methyl-phenylsulfonyl)-L-threitol via the following intermediates:

1,4-bis-O-[4-(4-tert.-butoxycarbonylmethoxy-benzyl)-phenyl]-2,3-O-isopropylidene-L-threitol, colorless solid, which was processed without further characterization;

1,4-bis-O-[4-(4-carboxymethoxy-benzyl)-phenyl)-2,3-O-isopropylidene-L-threitol, colorless solid, MS: m/z 660.5 ([M+NH$_4$]$^+$);

1,4-bis-O-[4-(4-carboxymethoxy-benzyl)-phenyl]-L-threitol, colorless solid, MS: m/z 625.5 ([M+Na]$^+$);

2,3-di-O-acetyl-1,4-bis-O-[4-(4-carboxymethoxy-benzyl)-phenyl]-L-threitol, brownish, amorphous solid, MS: m/z 685.4 ([M–H]$^-$);

2,3-di-O-acetyl-1,4-bis-O-[4-[4-(2,3,4,5,6-penta-O-acetyl-D-glucit-1-ylcarbamoylmethoxy)-benzyl]-phenyl]-L-threitol, colorless amorphous solid, MS: m/z 1456.8 ([M+Na]$^+$).

C. The 1,4-bis-O-[4-(4-D-glucit-1-ylcarbamoylmethoxy-benzyl)-phenyl]-L-threitol obtained above was converted analogously to Example 1.B. into 1,4-bis-O-[4-[4-(2,3,4,5,6-penta-O-sulfo-D-glucit-1-ylcarbamoylmethoxy)-benzyl]-phenyl]-2,3-di-O-sulfo-L-threitol dodecasodium salt, [a]+0.50° (c 0.6; water), MS: m/z 2154.0 (reconstructed M).

EXAMPLE 16

A. 1,6-Bis-O-(6-D-glucit-1-ylcarbamoyl-naphthalen-2-yl)-galactitol was obtained as a reddish solid, MS: m/z 871.5 ([M+Na]$^+$), analogously to Example 3.A.-D. from methyl 6-hydroxy-naphthalene-2-carboxylate and 2,3:4,5-di-O-isopropylidene-1,6-bis-O-(4-methyl-phenylsulfonyl)-galactitol via the following intermediates:

2,3:4,5-Di-O-isopropylidene-1,6-bis-O-(6-methoxycarbonyl-naphthalen-2-yl)-galactitol, colorless solid, MS: m/z 630 ([M]$^+$);

1,6-bis-O-(6-carboxy-naphthalen-2-yl)-2,3:4,5-di-O-isopropylidene-galactitol, colorless solid, MS: m/z 601.3 ([M–H]$^-$);

1,6-bis-O-(6-D-glucit-1-ylcarbamoyl-naphthalen-2-yl)-2,3:4,5-di-O-isopropylidene-galactitol, colorless solid, MS: m/z 929.7 ([M+H]$^+$).

B. The 1,6-bis-O-(6-D-glucit-1-ylcarbamoyl-naphthalen-2-yl)-galactitol was converted analogously to Example 1.B. into 1,6-bis-O-[6-(2,3,4,5,6-penta-O-sulfo-D-glucit-1-ylcarbamoyl)-naphthalen-2-yl]-2,3,4,5-tetra-O-sulfo-galactitol tetradecasodium salt, [a]–4.1° (c 0.7; water)

EXAMPLE 17

A. 100 ml of sodium methylate solution in methanol (prepared with 2.6 g of sodium) followed by 22.29 g of 4-chloromethyl-biphenyl were added while stirring and with the exclusion of moisture to 16.82 g of methyl 3,5-dihydroxy-benzoate dissolved in 120 ml of methanol and the mixture was stirred at 90° C. for 4 hours. Thereupon, the reaction mixture was concentrated, and the residue was partitioned between methylene chloride and dilute hydrochloric acid. The combined methylene chloride phases were dried over magnesium sulfate and concentrated, and the residue was chromatographed on silica gel with methylene chloride/methanol. The thus-obtained product fraction was recrystallized from methylene chloride. There was thus obtained methyl 3-biphenyl-4-ylmethoxy-5-hydroxy-benzoate in the form of colorless crystals, MS:m/z 334 ([M]$^+$).

B. 1,6-Bis-O-(3-biphenyl-4-ylmethoxy-5-D-glucit-1-ylcarbamoyl-phenyl)-2,3:4,5-di-O-isopropylidene-galactitol was obtained in the form of colorless crystals, MS: m/z 1215.3 ([M+Na]$^+$), from methyl 3-biphenyl-4-ylmethoxy-5-hydroxy-benzoate and 2,3:4,5-di-O-isopropylidene-1,6-bis-O-(4-methyl-phenylsulfonyl)-galactitol via the following intermediates:

1,6-bis-O-(3-biphenyl-4-ylmethoxy-5-methoxycarbonyl-phenyl)-2,3:4,5-di-O-isopropylidene-galactitol, colorless solid, which was processed without further characterization;

1,6-bis-O-(3-biphenyl-4-ylmethoxy-5-carboxy-phenyl)-2,3:4,5-di-O-isopropylidene-galactitol, colorless solid, MS: m/z 865.2 ([M–H]$^-$).

C. 0,2 g of 1,6-bis-O-(3-biphenyl-4-ylmethoxy-5-D-glucit-1-ylcarbamoyl-phenyl)-2,3:4,5-di-O-isopropylidene-galactitol was suspended in 2 ml of dioxan, 0.5 ml of trifluoroacetic acid and 0.7 ml of water and stirred at room temperature for 72 hours. Thereupon, the reaction mixture was concentrated and the residue was treated with methanol and filtered. There was thus obtained 1,6-bis-O-(3-biphenyl-4-ylmethoxy-5-D-glucit-1-ylcarbamoyl-phenyl)-galactitol as a colorless solid, MS: m/z 1114.4 ([M+H]$^+$).

D. The 1,6-bis-O-(3-biphenyl-4-ylmethoxy-5-D-glucit-1-ylcarbamoyl-phenyl)-galactitol obtained above was converted analogously to Example 1.B. into 1,6-bis-O-[3-biphenyl-4-ylmethoxy-5-(2,3,4,5,6-penta-O-sulfo-D-glucit-1-ylcarbamoyl)-phenyl]-2,3,4,5-tetra-O-sulfo-galactitol tetradecasodium salt, [a]–2,4° (c 0.7; water), MS: m/z 2512.0 (reconstructed [M–Na]).

EXAMPLE 18

A. 1,4-Bis-O-(4-D-glucit-1-ylcarbamoyl-phenyl)-L-threitol was obtained as a colorless solid, MS: m/z 689.3 ([M+H]$^+$), analogously to Example 3.A.-D. from methyl 4-hydroxy-benzoate and 2,3-O-isopropylidene-1,4-bis-O-(4-methyl-phenylsulfonyl)-L-threitol via the following intermediates:

2,3-O-Isopropylidene-1,4-bis-O-(4-methoxycarbonyl-phenyl)-L-threitol, colorless solid, MS: m/z 430 ([M]$^+$);

1,4-bis-O-(4-carboxy-phenyl)-2,3-O-isopropylidene-L-threitol, colorless solid, MS: m/z 402 ([M]$^+$);

1,4-bis-O-(4-D-glucit-1-ylcarbamoyl-phenyl)-2,3-O-isopropylidene-L-threitol, colorless solid, MS: m/z 729.4 ([M+H]$^+$).

B. The 1,4-bis-O-(4-D-glucit-1-ylcarbamoyl-phenyl)-L-threitol obtained above was converted analogously to Example 1.B. into 1,4-bis-O-[4-(2,3,4,5,6-penta-O-sulfo-D-glucit-1-ylcarbamoyl)-phenyl]-2,3-di-O-sulfo-L-threitol dodecasodium salt, [a]–3.1° (c 0.7; water), MS: m/z 1913.5 (reconstructed M).

EXAMPLE 19

A. 1,6-Bis-O-(3-D-glucit-1-ylcarbamoyl-naphthalen-1-yl)-galactitol was obtained as a colorless solid, MS: m/z 872.4 ([M+Na]$^+$), analogously to Example 3.A.-D. from ethyl 4-hydroxy-naphthalene-2-carboxylate and 2,3:4,5-di-O-isopropylidene-1,6-bis-O-(4-methyl-phenylsulfonyl)-galactitol via the following intermediates:

2,3:4,5-Di-O-isopropylidene-1,6-bis-O-(3-ethoxycarbonyl-naphthalen-1-yl)-galactitol, colorless solid, MS: m/z 658 ([M]$^+$);

1,6-bis-O-(3-carboxy-naphthalen-1-yl)-2,3:4,5-di-O-isopropylidene-galactitol, colorless solid, MS: m/z 602 ([M]$^+$);

1,6-bis-O-(3-D-glucit-1-ylcarbamoyl-naphthalen-1-yl)-2,3:4,5-di-O-isopropylidene-D-galactitol, colorless solid, MS: m/z 9518 ([M+Na]$^+$)

B. The 1,6-bis-O-(3-D-glucit-1-ylcarbamoyl-naphthalen-1-yl)-galactitol obtained above was converted analogously to Example 1.B. into 1,6-bis-O-[3-(2,3,4,5,6-penta-O-sulfo-D-glucit-1-ylcarbamoyl)-naphthalen-1-yl]-2,3,4,5-tetra-O-sulfo-galactitol tetradecasodium salt, [a]–1.2° (c 0.5; water), MS: m/z 2277.0 (reconstructed M).

EXAMPLE 20

A. 6.55 g of 3-hydroxy-7-methoxy-naphthalene-2-carboxylic acid were dissolved in 20 ml of dimethylformamide, treated with 5.5 g of sodium hydrogen carbonate and 4.0 ml of dimethyl sulfate and stirred at 90° C. under argon for 10 minutes. Subsequently, the reaction mixture was poured on to ice-water and extracted with ether. The combined ether phases were washed with water, dried over magnesium sulfate and concentrated. The thus-obtained residue was recrystallized from ethyl acetate/hexane. Methyl 3-hydroxy-7-methoxy-naphthalene-2-carboxylate with m.p. 138° C. was thus obtained.

B. 1,6-Bis-O-(3-D-glucit-1-ylcarbamoyl-6-methoxy-naphthalen-2-yl)-galactitol was obtained as a colorless solid, MS: m/z 909.3 ([M+H]$^+$), analogously to Example 12.A.-F. from methyl 3-hydroxy-7-methoxy-naphthalene-2-carboxylate and 2,3:4,5-di-O-isopropyl-idene-1,6-bis-O-(4-methyl-phenylsulfonyl)-galactitol via the following intermediates:

1,6-bis-O-(6-methoxy-3-methoxycarbonyl-naphthalen-2-yl)-2,3:4,5-di-O-isopropylidene-galactitol, colorless solid, MS: m/z 690 ([M]$^+$);

1,6-bis-O-(3-carboxy-6-methoxy-naphthalen-2-yl)-2,3:4,5-di-O-isopropylidene-galactitol, colorless solid, MS: m/z 661.2 ([M–H]$^-$);

1,6-bis-O-(3-carboxy-6-methoxy-naphthalen-2-yl)-galactitol, colorless solid, MS: m/z 581.2 ([M–H]$^-$);

2,3,4,5-tetra-O-acetyl-1,6-bis-O-(3-carboxy-6-methoxy-naphthalen-2-yl)-galactitol, colorless solid, MS: m/z 749.1 ([M–H]$^-$);

2,3,4,5-tetra-O-acetyl-1,6-bis-O-(3-D-glucit-1-ylcarbamoyl-6-methoxy-naphthalen-2-yl)-galactitol, colorless solid, MS: m/z 1077.4 ([M+H]$^+$).

C. The 1,6-bis-O-(3-D-glucit-1-ylcarbamoyl-6-methoxy-naphthalen-2-yl)-galactitol obtained above was converted analogously to Example 1.B. into 1,6-bis-O-[6-methoxy-3-(2,3,4,5,6-penta-O-sulfo-D-glucit-1-ylcarbamoyl)-naphthalen-2-yl]-2,3,4,5-tetra-O-sulfo-galactitol tetradecasodium salt, [a]–5.7° (c 0.6; water), MS: m/z 2337.5 (reconstructed M).

EXAMPLE 21

A. Methyl 3-hydroxy-5-methoxy-naphthalene-2-carboxylate with m.p. 182° C. was obtained analogously to Example 20.A. from 3-hydroxy-5-methoxy-naphthalene-2-carboxylic acid.

B. 1,6-Bis-O-(3-D-glucit-1-ylcarbamoyl-8-methoxy-naphthalen-2-yl)-galactitol was obtained as a colorless solid, MS: f/z 909.2 ([M+H]$^+$), analogously to Example 12.A.-F. from methyl 3-hydroxy-5-methoxy-naphthalene-2-carboxylate and 2,3:4,5-di-O-isopropylidene-1,6-bis-O-(4-methyl-phenylsulfonyl)-galactitol via the following intermediates:

2,3:4,5-Di-O-isopropylidene-1,6-bis-O-(8-methoxy-3-methoxy-carbonyl-naphthalen-2-yl)-galactitol, colorless solid, MS: m/z 690 ([M]$^+$);

1,6-bis-O-(3-carboxy-8-methoxy-naphthalen-2-yl)-2,3:4,5-di-O-isopropylidene-galactitol, MS: m/z 661.1 ([M–H]$^-$);

1,6-bis-O-(3-carboxy-8-methoxy-naphthalen-2-yl)-galactitol, colorless solid, MS: m/z 581.2 ([M–H]$^-$);

2,3,4,5-tetra-O-acetyl-1,6-bis-O-(3-carboxy-5-methoxy-naphthalen-2-yl)-galactitol, colorless solid, MS: m/z 749.1 ([M–H]$^-$);

2,3,4,5-tetra-O-acetyl-1,6-bis-O-[8-methoxy-3-(2,3,4,5,6-penta-O-acetyl-D-glucit-1-ylcarbamoyl)-naphthalen-2-yl]-galactitol, colorless solid, MS: m/z 1497.2 ([M+H]$^+$).

C. The 1,6-bis-O-(3-D-glucit-1-ylcarbamoyl-8-methoxy-naphthalen-2-yl)-galactitol obtained above was converted analogously to Example 1.B. into 1,6-bis-O-[8-methoxy-3-(2,3,4,5,6-penta-O-sulfo-D-glucit-1-ylcarbamoyl)-naphthalen-2-yl]-2,3,4,5-tetra-O-sulfo-galactitol tetradecasodium salt, [a]–9.30 (c 0,7; water), MS: m/z 2337.0 (reconstructed M).

EXAMPLE 22

A. 25.0 g of 3,7-dihydroxy-naphthalene-2-carboxylic acid and 22.5 g of sodium hydrogen carbonate were dissolved in 125 ml of dimethylformamide, treated with 16.5 ml of dimethyl sulfate and stirred at 85° C. for 20 minutes. Thereupon, the reaction mixture was poured on to ice-water. The crystals formed were filtered off, there being thus obtained methyl 3,7-dihydroxy-naphthalene-2-carboxylate as a yellowish solid, MS m/z 218 ([M]$^+$).

B. 6.5 g of methyl 3,7-dihydroxy-naphthalene-2-carboxylate and 11.3 g of (R)-2,2-dimethyl-[1,3]dioxolan-4-ylmethyl toluene-4-sulfonate were stirred at 80° C. for 60 hours in 50 ml of acetonitrile with the addition of 5.4 g of potassium carbonate. The reaction mixture was poured on to ice-water and extracted with ether. The combined ether phases were washed with water, dried over magnesium sulfate, filtered and evaporated; the thus-obtained residue was chromatographed on silica gel with hexane/ether, there being thus obtained methyl 7-[(S)-2,2-dimethyl-[1,3]dioxolan-4-ylmethoxy]-3-hydroxy-naphthalene-2-carboxylate as a yellowish solid, MS: m/z 332 ([M]$^+$).

C. 1,6-Bis-O-[6-[(R)-2,3-dihydroxy-propoxy]-3-D-glucit-1-ylcarbamoyl-naphthalen-2-yl]-galactitol was obtained as a colorless solid, MS m/z 1051.3 ([M+Na]$^+$), analogously to Example 3.A.-D. from methyl 7-[(S)-2,2-dimethyl-[1,3]dioxolan-4-ylmethoxy]-3-hydroxy-naphthalene-2-carboxylate and 2,3:4,5-di-O-isopropylidene-1,6-bis-O-(4-methyl-phenylsulfonyl)-galactitol via the following intermediates:

1,6-bis-O-[6-[(S)-2,2-dimethyl-[1,3]dioxolan-4-ylmethoxy]-3-methoxycarbonyl-naphthalen-2-yl]-2,3:4,5-di-O-isopropylidene-galactitol, colorless solid, MS: m/z 891.3 ([M+H]$^+$);

1,6-bis-O-[3-carboxy-6-[(S)-2,2-dimethyl-[1,3]dioxolan-4-yl]-naphthalen-2-yl]-2,3:4,5-di-O-isopropylidene-galactitol, colorless solid, MS: m/z 861.4 ([M–H]$^-$);

1,6-bis-O-[6-[(S)-2,2-dimethyl-[1,3]dioxolan-4-yl]-3-D-glucit 1-ylcarbamoyl-naphthalen-yl]-2,3:4,5-di-O-isopropylidene-galactitol, colorless solid, MS: m/z 1211.6 ([M+Na]$^+$);

D. The 1,6-bis-O-[6-[(R)-2,3-dihydroxy-propoxyl-3-D-glucit-1-ylcarbamoyl-naphthalen-2-yl]-galactitol obtained above was converted analogously to Example 1.B. into 1,6-bis-O-[6-[(S)-2,3-bis-sulfooxy-propoxy]-3-(2,3,4,5,6-penta-O-sulfo-D-glucit 1-ylcarbamoyl)-naphthalen-2-yl]-2,3,4,5-tetra-O-sulfo-galactitol octadecasodium salt, [a]–4.6° (c 0.7; water), MS: m/z 2864.0 (reconstructed M).

EXAMPLE 23

A. Methyl 7-bromo-3-hydroxy-naphthalene-2-carboxylate was obtained as a yellowish solid, MS m/z 280.282 ([M]$^+$), analogously to Example 22.A. from 7-bromo-3-hydroxy-naphthalene-2-carboxylic acid (R. A. Murphy et al., J. Med. Chem. 33, 171 (1990)).

B. 1,6-Bis-O-(6-bromo-3-D-glucit-1-ylcarbamoyl-naphthalen-2-yl)-galactitol was obtained as a colorless solid, MS m/z 1029.1 ([M+Na]$^+$), analogously to Example 3.A.-D. from methyl 7-bromo-3-hydroxy-naphthalene-2-carboxylate and 2,3:4,5-di-O-isopropylidene-1,6-bis-O-(4-methyl-phenylsulfonyl)-galactitol via the following intermediates:

1,6-bis-O-(6-bromo-3-methoxycarbonyl-naphthalen-2-yl)-2,3:4,5-di-O-isopropylidene-galactitol, colorless solid, MS: m/z 773 ([M–CH$_3$]$^+$);

1,6-bis-O-(6-bromo-3-carboxy-naphthalen-2-yl)-2,3:4,5-di-O-isopropylidene-galactitol, colorless solid, MS: m/z 783.2 ([M+Na]$^+$);

1,6-bis-O-(6-bromo-3-D-glucit-1-ylcarbamoyl-naphthalen-2-yl)-2,3:4,5-di-O-isopropylidene-galactitol, colorless solid, which was processed without further purification.

C. The 1,6-bis-O-(6-bromo-3-D-glucit-1-ylcarbamoyl-naphthalen-2-yl)-galactitol obtained above was converted analogously to Example 1.B. into 1,6-bis-O-[6-bromo-3-(2,3,4,5,6-penta-O-sulfo-D-glucit-1-ylcarbamoyl)-naphthalen-2-yl]-2,3,4,5-tetra-O-sulfo-galactitol tetradecasodium salt, [a]–15.4° (c 0.7; water).

EXAMPLE 24

A. A suspension of 1.78 g of dimethyl L-tartrate and 4.85 g of tris-hydroxymethyl-methylamine in 50 ml of methanol was heated under reflux for 6 days and then concentrated. The residue was purified by chromatography over silica gel with ethyl acetate/methanol/water as the eluent and gave N,N'-bis-(2-hydroxy-1,1-bis-hydroxymethyl-ethyl)-L-tartaramide, [a]+101.00 (c 0.4; dimethyl sulfoxide), MS: m/z 357.3 ([M+H]$^+$).

B. A suspension of 0.36 g of N,N'-bis-(2-hydroxy-1,1-bis-hydroxymethyl-ethyl)-L-tartaramide and 2.23 g of sulfur trioxide-trimethylamine complex in 10 ml of absolute dimethylformamide was stirred at 70° C. for 24 hours. After cooling, the mixture was treated with 2.63 g of sodium acetate in 50 ml of methanol. The precipitate was filtered off under suction, washed with methanol and dried. The residue was taken up in water and chromatographed on Sephadex® LH20 and SP Sephadex® C-25. The product fractions were lyophilized and gave 2,3-di-O-sulfo-N,N'-bis-(2-sulfooxy-1,1-bis-sulfooxymethyl-ethyl)-L-tartaramide octasodium salt, [a]+31.20 (c 0.5; water), MS: m/z 1172 (reconstructed M).

EXAMPLE 25

A. Dimethyl L-tartrate and D-glucamine were reacted with one another as described under Ex. 24.A. and gave L-tartaric acid N,N'-bis-D-glucit-1-yl-amide, [[a]+52.0° (c 0.5; dimethyl sulfoxide), MS: m/z 477.6 ([M+H]$^+$).

B. A suspension of 0.48 g of L-tartaric acid N,N'-bis-D-glucit-1-yl-amide and 3.34 g of sulfur trioxide-trimethylamine complex in 15 ml of absolute dimethylformamide was stirred at 70° C. for 18 hours. After cooling, the upper phase was decanted off. The residue was treated with 1.97 g of sodium acetate in 20 ml of water and evaporated, and the residue was then taken up several times in water and evaporated. The thus-obtained residue was taken up in water and chromatographed on Sephadex® LH20 and SP Sephadex® C-25. The product fractions were lyophilized and gave N,N'-bis-(2,3,4,5,6-penta-O-sulfo-D-glucit-1-yl)-di-O-sulfo-L-tartaramide dodecasodium salt, [a]+18.6° (c 0.5; water), MS: m/z 1705 (reconstructed M).

EXAMPLE 26

A. A suspension of 2.0 g of dimethyl D-tartrate and 4.47 g of D-glucamine in 50 ml of methanol was heated under reflux for 8 days, filtered off under suction and washed with methanol. The suction filter material was dried and acetylated with 110 ml of acetic anhydride in 220 ml of pyridine at room temperature for 18 hours. The reaction product was concentrated and the residue was precipitated from water and dried to give 2,3-di-O-acetyl-N,N'-bis-(2,3,4,5,6-penta-O-acetyl-D-glucit-1-yl)-D-tartaramide, [a]+10.4° (c 0.5; dimethyl sulfoxide), MS: m/z 1003.5 ([M+Na]$^+$).

B. A solution of 4.8 g of 2,3-di-O-acetyl-N,N'-bis-(2,3,4,5,6-penta-O-acetyl-D-glucit-1-yl)-D-tartaramide in 50 ml of methanol and 50 ml of tetrahydrofuran was treated with 4.8 ml of a 2% methanolic sodium methanolate solution and stirred at room temperature for 5 hours. The resulting precipitate was filtered off under suction, washed with methanol and dried at 60° C. in a vacuum to give N,N'-di-D-glucit-1-yl-D-tartaramide, MS: n/z 499.6 ([M+Na]$^+$).

C. A suspension of 1.0 g of N,N'-di-D-glucit-1-yl-D-tartaramide and 9.07 g of sulfur trioxide-triethylamine complex in 50 ml of absolute dimethylformamide was stirred at 45° C. for 20 hours. After cooling, the mixture was concentrated in a high vacuum and the residue was treated with a solution of 8.2 g of sodium acetate in 90 ml of water and evaporated. The residue was treated several times with water and again evaporated. The thus-obtained residue was taken up in water and chromatographed on Sephadex® LH20 and SP Sephadex® C-25. The product fractions were lyophilized and gave N,N'-bis-(2,3,4,5,6-penta-O-sulfo-D-glucit-1-yl)-2,3-di-O-sulfo-D-tartaramide dodecasodium salt, [a]–28.8° (c 0.5; water), MS: m/z 1700.5 (reconstructed M).

EXAMPLE 27

A. Reaction of dimethyl meso-tartrate and D-glucamine as described in Ex. 26.A. gave 2,3-di-O-acetyl-N,N'-bis-(2,3,4,5,6-penta-O-acetyl-D-glucit-1-yl)-meso-tartaramide, [a]$^+$6.2° (c 0.5; dimethyl sulfoxide), MS: m/z 1003.8 ([M+Na]$^+$).

B. Deacetylation of 2,3-di-O-acetyl-N,N'-bis-(2,3,4,5,6-penta-O-acetyl-D-glucit-1-yl)-meso-tartaramide as described in Ex. 26.B. gave N,N'-di-D-glucit-1-yl-meso-tartaramide, MS: m/z 499.4 ([M+Na]$^+$).

C. Sulfation of N,N'-di-D-glucit-1-yl-meso-tartaramide as described in Ex. 26.C. gave N,N'-bis-(2,3,4,5,6-penta-O-sulfo-D-glucit-1-yl)-2,3-di-O-sulfo-meso-tartaramide dodecasodium salt, [a]–4.6° (c 0.5; water), MS: m/z 1700.5 (reconstructed M).

EXAMPLE 28

A. Reaction of dimethyl galactarate and tris-hydroxymethyl-methylamine as described in Ex. 25.A. gave N,N'-bis-(2- hydroxy-1,1-bis-hydroxymethyl-ethyl)-galactaramide, MS: m/z 417.1 ([M+H]$^+$).

B. Sulfation of N,N'-bis-(2-hydroxy-1,1-bis-hydroxymethyl-ethyl)-galactaramide as described in Ex. 25.B. gave 2,3,4,5-tetra-O-sulfo-N,N'-bis-(2-sulfooxy-1,1-bis-sulfooxymethyl-ethyl)-galactaramide decasodium salt, MS: m/z 1436.0 (reconstructed M).

EXAMPLE 29

A. Reaction of dimethyl galactarate and D-glucamine as described in Ex. 25.A. gave N,N'-di-D-glucit-1-yl-galactaramide, [a]-14.4° (c 0.5; water), MS: m/z 537.2 ([M+H]$^+$).

B. Sulfation of N,N'-di-D-glucit-1-yl-galactaramide as described in Ex. 25.B. gave N,N'-bis-(2,3,4,5,6-penta-O-sulfo-D-glucit-1-yl)-2,3,4,5-tetra-O-sulfo-galactaramide tetradecasodium salt, MS: m/z 1963.0 (reconstructed M).

EXAMPLE 30

A. 15 g of 4-aminomethyl-benzylamine were dissolved in 600 ml of methylene chloride and treated within 2.5 hours with a solution of 8.0 g of di-tert.-butyl dicarbonate in 80 ml of methylene chloride. Thereupon, the separated precipitate was filtered off and discarded and the mother liquor was evaporated. The thus-obtained residue was chromatographed on silica gel with hexane/ethyl acetate/methanol; there thus being obtained tert.-butyl (4-aminomethyl-benzyl)-carbamate, MS: m/z 179 ([M-tert.-butyl]$^+$).

B. 0.6 ml of diethyl D-tartrate and 1.81 g of tert.-butyl (4-aminomethyl-benzyl)-carbamate were dissolved in 20 ml of ethanol and heated under reflux at 85° C. for 44 hours. After cooling to 0° C., the separated crystals were filtered off and dried in a high vacuum; there was thus obtained N,N'-bis-(4-tert.-butoxycarbonylamino-methyl-benzyl)-D-tartaramide, MS: m/z 587.1 ([M+H]$^+$).

C. 0.594 g of N,N'-bis-(4-tert.-butoxycarbonylaminomethyl-benzyl)-D-tartaramide was dissolved in 0.8 ml of trifluoroacetic acid at 0° C. and subsequently stirred at room temperature for 5 hours; the mixture was subsequently evaporated and the residue was treated with methylene chloride/ether (1:1). The precipitate which formed was filtered off. There was obtained N,N'-bis-(4-aminomethyl-benzyl)-D-tartaramide di(trifluoroacetate), MS: m/z 387.4 ([M+H]$^+$).

D. 0.69 g of N,N'-bis-(4-aminomethyl-benzyl)-D-tartaramide di-(trifluoroacetate) was dissolved in 40 ml of ethanol, treated with 0.47 ml of triethylamine and 0.48 g of D-gluconic acid d-lactone and stirred at 85° C. for 16 hours. After cooling, the precipitate formed was filtered off, washed with ether and dried in a high vacuum. There was thus obtained N,N'-bis-(4-D-glucit-1-ylcarbamoylmethyl-benzyl)-D-tartaramide, MS m/z 743.4 ([M+H]$^+$).

E. The N,N'-bis-(4-D-glucit-1-ylcarbamoylmethyl-benzyl)-D-tartaramide obtained above was converted analogously to Example 1.B. into N,N'-bis-[4-(2,3,4,5,6-penta-O-sulfo-D-glucit-1-yl-carbamoylmethyl)-benzyl]-di-O-sulfo-D-tartaramide dodecasodium salt, MS: m/z 1967.0 (reconstructed M).

EXAMPLE 31

A. 0.97 g of 1-O-(4-amino-phenyl)-2,3:4,5-di-O-isopropylidene-D-arabinitol (prepared as described in European Patent Application 95 100 180.9 of 9.1.95) and 0.27 g of benzene-1,3,5-tricarboxylic acid trichloride were dissolved in 22 ml of methylene chloride, treated with 1.0 ml of triethylamine at 5° C. and stirred at room temperature for 60 hours. After concentration, the crude product was chromatographed on silica gel with methylene chloride and methanol. There was obtained benzene-1,3,5-tricarboxylic acid tris-[4-(2,3:4,5-di-O-isopropylidene-D-arabinit-1-yloxy)-phenylamide], MS: m/z 1127 ([M+H]$^+$).

B. 0.95 g of benzene-1,3,5-tricarboxylic acid tris-[4-(2,3:4,5-di-O-isopropylidene-D-arabinit-1-yloxy)-phenylamide] was dissolved in 20 ml of dioxan, treated with 3 ml of trifluoroacetic acid (35%) and stirred at reflux for 7 hours. Subsequently, 50 ml of toluene were added twice and the mixture was concentrated in a water-jet vacuum each time. The thus-obtained residue was dried in a high vacuum at room temperature over phosphorus pentoxide for 4 hours. There was thus obtained benzene-1,3,5-tricarboxylic acid tris-(4-D-arabinit-1-yloxy-phenylamide) which was used directly in the next step.

C. 0.98 g of benzene-1,3,5-tricarboxylic acid tris-(4-D-arabinit-1-yloxy-phenylamide) was reacted with sulfur trioxiode-trimethylamine complex in analogy to Example 1.B. There was thus obtained benzene-1,3,5-tricarboxylic acid tris-[4-(2,3,4,5-tetra-O-sulfo-D-arabinit-1yloxy)-phenylamide] dodecasodium salt, MS: m/z 2110.0 (reconstructed M).

EXAMPLE 32

A. 18.2 g of 5-hydroxyisophthalic acid were stirred at reflux for 18 hours in 300 ml of methanol with the addition of 5 ml of sulfuric acid (96%). After cooling to 5° C., the mixture was adjusted to pH 8 with saturated sodium bicarbonate solution and then the methanol was distilled off in a water-jet vacuum. The heterogeneous aqueous phase was exhaustively extracted with methylene chloride; the organic phase was dried over magnesium sulfate, filtered and concentrated. There was obtained dimethyl 5-hydroxy-isophthalate which was recrystallized from methylene chloride/n-hexane, m.p. 159°–161° C.

B. 2.1 g of dimethyl 5-hydroxy-isophthalate and 2.9 g of (R)-2,2-dimethyl-[1,3]dioxolan-4-ylmethyl toluene-4-sulfonate were stirred at reflux for 3 hours in 120 ml of dimethylformamide with the addition of 6.9 g of potassium carbonate. The reaction mixture was poured on to ice-water, extracted with methylene chloride, the combined methylene chloride phases were washed with water, dried over magnesium sulfate, filtered and evaporated. There was obtained dimethyl (S)-5-(2,2-dimethyl-[1,3] dioxolan-4-ylmethoxy)-isophthalate, MS: m/z 324 ([M]$^+$).

C. 1.40 g of dimethyl (S)-5-(2,2-dimethyl-[1,3]dioxolan-4-ylmethoxy)-isophthalate were stirred at room temperature for 16 hours with 4 ml of sodium hydroxide solution (28%) in 50 ml of methanol. After neutralization with 6N hydrochloric acid, the methanol was distilled off in a water-jet vacuum. The residue was poured on to ice-water, extracted with methylene chloride, the combined methylene chloride phases were washed with water, dried over magnesium sulfate, filtered and evaporated. There was obtained (S)-5-(2,2-dimethyl-[1,3]dioxolan-4-ylmethoxy)-isophthalic acid, MS: m/z 296 ([M]$^+$).

D. 0.59 g, of (S)-5-(2,2-dimethyl-[1,3]dioxolan-4-ylmethoxy)-isophthalic acid dissolved in 10 ml of acetonitrile was treated with 0.44 ml of 4-methylmorpholine at 0°–5° C. with the exclusion of moisture and stirred intensively for 10 minutes. Thereupon, 0.70 g of solid 2-chloro-4,6-dimethoxy-1,3,5-triazine was added and the mixture was stirred at 0°–5° C. for a further 2 hours. Subsequently, 1.29 g of 1-O-(4-amino-phenyl)-2,3:4,5-di-O-isopropylidene-D-arabinitol dissolved in 30 ml of acetonitrile/dimethylformamide (2:1) was added and the mixture was stirred at room temperature for a further 18 hours. After distillation of the solvent in a high vacuum, the residue was chromatographed on silica gel with methylene chloride and methanol. There was obtained (S)-N,N'-bis-[4-(2,3:4,5-di-O-isopropylidene-D-arabinit-1-yloxy)-phenyl]-5-(2,2-dimethyl-[1,3]dioxolan-4-ylmethoxy)-isophthalamide, MS: m/z 907 ([M+H]$^+$).

E. 2.05 g of (S)-N,N'-bis-[4-(2,3:4,5-di-O-isopropylidene-D-arabinit-1-yloxy)-phenyl]-5-(2,2-dimethyl-[1,3]dioxolan-4-ylmethoxy)-isophthalamide were dissolved in 50 ml of dioxan, treated with 15 ml of trifluoroacetic acid (70% in water) and stirred at reflux for 12 hours. Subsequently, 50 ml of toluene were added twice and the mixture was concentrated each time in a water-jet vacuum. The thus-obtained residue was dried in a high vacuum at room temperature over phosphorus pentoxide for 4 hours. There was obtained (R)-N,N'-bis-(4-D-arabinit-1-yloxy-phenyl)-5-(2,3-dihydroxy-propoxy)-isophthalamide, MS: m/z 707 ([M+H]$^+$).

F. 1.05 g of (R)-N,N'-bis-(4-D-arabinit-1-yloxy-phenyl)-5-(2,3-dihydroxy-propoxy)-isophthalamide were reacted with sulfur trioxide-trimethylamine complex in analogy to Example 1.B. There was thus obtained (S)-N,N'-bis-[4-(2,3,4,5-tetra-O-sulfo-D-arabinit-1yloxy)-phenyl]-5-(2,3-bis-sulfooxy-propoxy)-isophthalamide decasodium salt, MS: m/z, 1727.0 (reconstructed M).

EXAMPLE 33

A. 2.35 g of 2,3-O-isopropylidene-1,4-di-O-(4-methylphenylsulfonyl)-L-threitol and 1.52 g of methyl 4-hydroxy-benzoate were stirred at reflux for 3 hours in 75 ml of dimethylformamide with the addition of 3.46 g of potassium carbonate. The reaction mixture was poured on to ice-water, extracted with methylene chloride, the combined methylene chloride phases were washed with water, dried over magnesium sulfate, filtered and evaporated. The crude product was chromatographed on silica gel with methylene chloride and methanol. There was obtained 2,3-O-isopropylidene-1,4-bis-O-(4-methoxycarbonyl-phenyl)-L-threitol, MS: m/z 430 ([M]$^+$).

B. 1.81 g of 2,3-O-isopropylidene-1,4-bis-O-(4-methoxycarbonyl-phenyl)-L-threitol were stirred at 50° C. for 20 hours in 50 ml of methanol with the addition of 5 ml of sodium hydroxide solution (28%). The reaction mixture was thereafter cooled to 10° C., adjusted to pH 2 with hydrochloric acid and the methanol was distilled off in a water-jet vacuum. 100 ml of water were added to the residue, the mixture was stirred in an ice bath for 1 hour, then filtered and dried. There was obtained 1,4-bis-O-(4-carboxy-phenyl)-L-threitol, MS: m/z 361 ([M–H]$^-$).

C. 1.33 g of 1,4-bis-O-(4-carboxy-phenyl)-L-threitol were stirred at room temperature for 20 hours in 20 ml of pyridine with 3.8 ml of acetic anhydride. The reaction mixture was poured on to ice-water, extracted with methylene chloride, the combined methylene chloride phases were washed with water, dried over magnesium sulfate, filtered and evaporated. There was obtained 2,3-di-O-acetyl-1,4-bis-O-(4-carboxy-phenyl)-L-threitol which was recrystallized from methanol/methylene chloride, MS: m/z 387 ([M–AcO]$^-$).

D. 0.89 g of 2,3-di-O-acetyl-1,4-bis-O-(4-carboxy-phenyl)-L-threitol dissolved in 10 ml of acetonitrile was treated with 0.44 ml of 4-methylmorpholine at 0°–5° C. with the exclusion of moisture and stirred intensively for 10 minutes. Thereupon, 0.70 g of solid 2-chloro-4,6-dimethoxy-1,3,5-triazine was added and the mixture was stirred at 0°–5° C. for a further 2 hours. Subsequently, 1.29 g of 1-O-(4-amino-phenyl)2,3:4,5-di-O-isopropylidene-D-arabinitol dissolved in 30 ml of acetonitrile/dimethylformamide (2:1) were added and the mixture was stirred at room temperature for a further 18 hours. After distillation of the solvent in a high vacuum, the residue was chromatographed on silica gel with methylene chloride and methanol. There was obtained 2,3-di-O-acetyl-1,4-bis-O-[4-[4-(2,3:4,5-di-O-isopropylidene-D-arabinit-1-yloxy)-phenylcarbamoyl]-phenyl]-L-threitol, MS: m/z 1057 ([M+H]$^+$).

E. 2.9 g of 2,3-di-O-acetyl-1,4-bis-O-[4-[4-(2,3:4,5-di-O-isopropylidene-D-arabinit-1-yloxy)-phenylcarbamoyl]-phenyl]-L-threitol were dissolved in 40 ml of dioxan, treated with 2.8 ml of trifluoroacetic acid and 5.6 ml of distilled water and stirred under reflux for 3 hours; subsequently 100 ml of toluene were added twice and the mixture was concentrated in a water-jet vacuum each time. The thus-obtained residue was dried in a high vacuum at room temperature over phosphorus pentoxide for 4 hours. There was thus obtained 2,3-di-O-acetyl-1,4-bis-O-[4-(4-D-arabinit-1-yloxy-phenylcarbamoyl)-phenyl]-L-threitol which was used directly in the next step.

F. 2.08 g of 2,3-di-O-acetyl-1,4-bis-O-[4-(4-D-arabinit-1-yloxy-phenylcarbamoyl)-phenyl]-L-threitol were stirred at room temperature for 18 hours in 50 ml of methanol with 1.0 g of potassium carbonate with the addition of 15 ml of water/dimethylformamide (2:1). The solvent was distilled off in a high vacuum and the residue was then taken up in 50 ml of water, filtered and the residue was dried. There was obtained 1,4-bis-O-[4-(4-D-arabinit-1-yloxy-phenylcarbamoyl)-phenyl]-L-threitol. Elementary analysis calculated for $C_{40}H_{48}N_2O_{16}$: C=59.11%, H=5.95%, N=3.45%; found: C=58.69%, H=6.07%, N=3.10%.

G. 1.20 g of 1,4-bis-O-[4-(4-D-arabinit-1-yloxy-phenylcarbamoyl)-phenyl]-L-threitol were reacted with sulfur trioxide-trimethylamine complex in analogy to Example 1.B. There was thus obtained 1,4-bis-O-[4-[4-(2,3,4,5-tetra-O-sulfo-D-arabinit-1-yloxy)-phenyl-carbamoyl]-phenyl]-2,3-di-O-sulfo-L-threitol decasodium salt, MS: m/z 1833.0 (reconstructed M).

EXAMPLE 34

A. 16.7 g of 2,5-O-methylene-1,6-bis-O-(4-methyl-phenylsulfonyl)-D-mannitol (B. Lamm et al., Acta Chem. Scand. B 41, 202 (1987)) were stirred at room temperature under argon for 16 hours with the addition of 0.1 g of p-toluenesulfonic acid in 80 ml of trimethyl orthoformate. After neutralization with potassium carbonate and subsequent filtration, the filtrate was concentrated. The residue was recrystallized from methanol. There was obtained 3,4-O-methoxymethylene-2,5-O-methylene-1,6-bis-O-(4-methyl-phenylsulfonyl)-D-mannitol, MS: m/z 545 ([M+H]$^+$).

B. 4.36 g of 3,4-O-methoxymethylene-2,5-O-methylene-1,6-bis-O-(4-methyl-phenylsulfonyl)-D-mannitol were reacted with 2.44 g of methyl 4-hydroxy-benzoate and worked up in analogy to Example 33.A. The crude product was chromatographed on silica gel with methylene chloride and methanol. There was obtained 1,6-bis-O-(4-methoxycarbonyl-phenyl)-3,4-O- methoxymethylene-2,5-O-methylene-D-mannitol, MS: m/z 504 ([M]⁺).

C. 3.12 g of 1,6-bis-O-(4-methoxycarbonyl-phenyl)-3,4-O-methoxymethylene-2,5-O-methylene-D-mannitol were stirred at reflux for 6 hours in 100 ml of methanol with 6 ml of sodium hydroxide solution (28%). After cooling to 10° C., the reaction mixture was adjusted to pH 2 with dilute hydrochloric acid and the methanol was then distilled off in a water-jet vacuum. 100 ml of water were added to the residue, the mixture was stirred in an ice bath for 1 hour, then filtered and the residue was dried. There was thus obtained 1,6-bis-O-(4-carboxy-phenyl)-2,5-O-methylene-D-mannitol, MS: m/z 433 ([M−H]⁻).

D. 2.05 g of 1,6-bis-O-(4-carboxy-phenyl)-2,5-O-methylene-D-mannitol were stirred at reflux for 18 hours in 55 ml of 20% sulfuric acid in methanol. Then, after cooling to room temperature, 50 ml of ice-water were added and the methanol was distilled off in a water-jet vacuum. The residual heterogeneous aqueous phase was filtered and the residue was dried. There was obtained 1,6-bis-O-(4-methoxycarbonyl-phenyl)-D-mannitol, MS: m/z 449 ([M−H]⁻).

E. 2.33 g of 1,6-bis-O-(4-methoxycarbonyl-phenyl)-D-mannitol were reacted and worked up in analogy to Example 34.C. There was obtained 1,6-bis-O-(4-carboxy-phenyl)-D-mannitol, MS: m/z 421 ([M−H]⁻).

F. 2.10 g of 1,6-bis-O-(4-carboxy-phenyl)-D-mannitol were stirred at room temperature for 20 hours in 30 ml of pyridine with 5.1 ml of acetic anhydride. The reaction mixture was worked up extractively with ice-water and methylene chloride. The organic phase was dried over magnesium sulfate, filtered and concentrated. The residue was recrystallized from methanol and methylene chloride. There was obtained 2,3,4,5-tetra-O-acetyl-1,6-bis-O-(4-carboxy-phenyl)-D-mannitol, MS: m/z 589 ([M−H]⁻).

G. 1.18 g of 2,3,4,5-tetra-O-acetyl-1,6-bis-O-(4-carboxy-phenyl)-D-mannitol were reacted with 1-O-(4-amino-phenyl)-2,3:4,5-di-O-isopropylidene-D-arabinitol in analogy to Example 33.D. The crude product was chromatographed on silica gel with methylene chloride and methanol. There was obtained 2,3,4,5-tetra-O-acetyl-1,6-bis-O-[4-[4-(2,3:4,5-di-O-isopropylidene-D-arabinit-1-yloxy)-phenylcarbamoyl]-phenyl]-D-mannitol, MS: m/z 1201 ([M+H]⁺).

H. 2.28 g of 2,3,4,5-tetra-O-acetyl-1,6-bis-O-[4-[4-(2,3:4,5-di-O-isopropylidene-D-arabinit-1-yloxy)-phenylcarbamoyl]-phenyl]-D-mannitol were stirred at room temperature for 18 hours with 2.0 g of potassium carbonate in 60 ml of methanol with the addition of 10 ml of water. The methanol was distilled off in a water-jet vacuum, 50 ml of water were added to the residue and the mixture was filtered. After drying over phosphorus pentoxide, there was obtained 1,6-O-bis-[4-[4-(2,3:4,5-di-O-isopropylidene-D-arabinit-1-yloxy)-phenylcarbamoyl]-phenyl]-D-mannitol, MS: m/z 1033 ([M+H]⁺).

I. 1.67 g of 1,6-bis-O-[4-[4-(2,3:4,5-di-O-isopropylidene-D-arabinit-1-yloxy)-phenylcarbamoyl]-phenyl]-D-mannitol were dissolved in 50 ml of toluene, treated with 15 ml of trifluoroacetic acid (70% in water) and stirred at reflux for 3 hours. Subsequently, 50 ml of toluene were added twice and the mixture was concentrated in a water-jet vacuum each time. The thus-obtained residue was dried in a high vacuum at room temperature over phosphorus pentoxide for 4 hours. There was thus obtained 1,6-O-bis-[4-(4-D-arabinit-1-yloxy-phenylcarbamoyl)-phenyl]-D-mannitol, IR: (KBr, cm⁻¹): 3307, 1638, 1607, 1538, 1249, 1076, 826.

K. 1.31 g of 1,6-bis-O-[4-(4-D-arabinit-1-yloxy-phenyl-carbamoyl)-phenyl]-D-mannitol were reacted with sulfur trioxide-trimethylamine complex in analogy to Example 1.B. There was thus obtained 1,6-bis-O-[4-[4-(2,3,4,5-tetra-O-sulfo-D-arabinit-1-yloxy)-phenylcarbamoyl]-phenyl]-2,3,4,5-tetra-O-sulfo-D-mannitol dodecasodium salt, MS: m/z 2097.0 (reconstructed M).

EXAMPLE 35

A. 10.01 g of meso-tartaric acid monohydrate were stirred at reflux under argon for 15 minutes in 35 ml of acetic anhydride with the addition of 0.3 ml of concentrated sulfuric acid; after cooling the reaction mixture to 5° C. 150 ml of diethyl ether were added while stirring, the mixture was then filtered and the filtrate was concentrated. There was thus obtained di-O-acetyl-meso-tartaric anhydride, MS: m/z 235.2 ([M+H]⁺) (=dicarboxylic acid), IR: (KBr, cm⁻¹): 1800, 1752, 1214.

B. 2.16 g of di-O-acetyl-meso-tartaric anhydride and 2.60 g of 1-O-(4-amino-phenyl)-2,3:4,5-di-O-isopropylidene-D-arabinitol were stirred at room temperature for 16 hours in 120 ml of methylene chloride. After distillation of the solvent, the product was chromatographed on silica gel with methylene chloride and methanol. There was obtained a mixture of (2R,3S)- and (2S,3R)-di-O-acetyl-N-[4-(2,3:4,5-di-O-isopropylidene-D-arabinit-1-yloxy)-phenyl]-meso-tartaramic acid, MS: m/z 538.4 ([M−H]⁻).

C. 0.54 g of a mixture of (2R,3S)- and (2S,3R)-di-O-acetyl-N-[4-(2,3:4,5-di-O-isopropylidene-D-arabinit-1-yloxy)-phenyl]-meso-tartaramic acid in 15 ml of methylene chloride was reacted at −20° C. with 0.10 ml of oxalyl chloride with the addition of 1 drop of dimethylformamide; after 2 hours firstly 0.28 ml of triethylamine and then 0.32 g of 1-O-(4-amino-phenyl)-2,3:4,5-di-O-isopropylidene-D-arabinitol dissolved in 5 ml of methylene chloride were added dropwise at −25° C. After warming to room temperature, the solvent was distilled off and the residue was chromatographed on silica gel with methylene chloride and methanol. There was obtained di-O-acetyl-N,N'-bis-[4-(2,3:4,5-di-O-isopropylidene-D-arabinit-1-yloxy)-phenyl]-meso-tartaramide, MS: m/z 845.6 ([M+H]⁺).

D. 2.32 g of di-O-acetyl-N,N'-bis-[4-(2,3:4,5-di-O-isopropylidene-D-arabinit-1-yloxy)-phenyl]-meso-tartaramide were stirred at room temperature for 3 hours with 2.78 g of potassium carbonate in methanol/water in analogy to Example 34.H. The reaction mixture was worked up extractively with water and ethyl acetate. The crude product was chromatographed on silica gel with methylene chloride and acetonitrile. There was obtained N,N'-bis-[4-(2,3:4,5-di-O-isopropylidene-D-arabinit-1-yloxy)-phenyl]-meso-tartaramide, MS: m/z 761.3 ([M+H]⁺).

E. 1.40 g of N,N'-bis-[4-(2,3:4,5-di-O-isopropylidene-D-arabinit-1-yloxy)-phenyl]-meso-tartaramide were dissolved in 45 ml of dioxan, treated with 15 ml of trifluoroacetic acid (70% in water) and stirred at reflux for 3 hours. Subsequently, 50 ml of toluene were added twice and the mixture was concentrated in a water-jet vacuum each time. The thus-obtained residue was dried in a high vacuum at at 50° C. over phosphorus pentoxide for 16 hours. There was obtained N,N'-bis-(4-D-arabinit-1-yloxy-phenyl)-meso-tartaramide, IR: (KBr, cm⁻¹): 3390, 3304, 1661, 1604, 1539, 1513, 1241, 1077, 1042, 824.

F. 0.90 g of N,N'-bis-(4-D-arabinit-1-yloxy-phenyl)-meso-tartaramide was reacted with sulfur trioxide-trimethylamine complex in analogy to Example 1.B. There was thus obtained di-O-sulfo-N,N'-bis-[4-(2,3,4,5- tetra-O-sulfo-D-arabinit-1-yloxy)-phenyl]-meso-tartaramide decasodium salt, MS: m/z 1621.0 (reconstructed M).

EXAMPLE 36

A. 14.6 g of 2,3:4,5-di-O-isopropylidene-D-arabinitol (European Patent Application 247721 A1, 21st. Apr. 1987, DOW CHEMICAL COMPANY) were reacted with 12.7 g of p-toluenesulfonyl chloride in 55 ml of pyridine with the addition of 0.05 g of 4-(N,N-dimethylamino)-pyridine. After distillation of the solvent, the reaction mixture was worked up extractively with dilute hydrochloric acid/ice and ethyl acetate. There was obtained 2,3:4,5-di-O-isopropylidene-1-O-(4-methyl-phenylsulfonyl)-D-arabinitol which was recrystallized from ethyl acetate/n-hexane, elementary analysis calculated for $C_{18}H_{26}O_7S$: C=55.94%, H=6.78%; found: C=56.02%, H=6.77%.

B. 11.60 g of 2,3:4,5-di-O-isopropylidene-1-O-(4-methyl-phenylsulfonyl)-D-arabinitol were reacted with 8.50 g of 4'-benzyloxy-biphenyl-biphenyl-4-ol (H. Kapitza & R. Zentel, Makromol. Chem. 192, 1859 (1991)) and 20.7 g of potassium carbonate in 350 ml of N,N-dimethylformamide in analogy to Example 33.A. After distillation of the solvent, the crude product was chromatographed on silica gel with methylene chloride and methanol. There was obtained 1-O-(4'-benzyloxy-biphenyl-4-yl)-2,3:4,5-di-O-isopropylidene-D-arabinitol, MS: m/z 490 ([M]$^+$).

C. 9.80 g of 1-O-(4'-benzyloxy-biphenyl-4-yl)-2,3:4,5-di-O-isopropylidene-D-arabinitol were debenzylated by catalytic hydrogenation with 2.5 g of Pd-charcoal (10%) in ethyl acetate. There was obtained 1-O-(4'-hydroxy-biphenyl-4-yl)-2,3:4,5-di-O-isopropylidene-D-arabinitol, elementary analysis calculated for $C_{23}H_{28}O_6$: C=68.98%, H=7.05%; found: C=68.76%, H=7.10%.

D. 2.00 g of 1-O-(4'-hydroxy-biphenyl-4-yl)-2,3:4,5-di-O-isopropylidene-D-arabinitol and 1.18 g of 2,3-O-isopropylidene-1,4-bis-O-(4-methyl-phenylsulfonyl)-L-threitol were reacted and worked up as described in Example 33.A. The crude product was chromatographed on silica gel with n-hexane, methylene chloride and acetonitrile. There was obtained 1,4-bis-O-[4'-(2,3:4,5-di-O-isopropylidene-D-arabinit-1-yloxy)-biphenyl-4-yl]-2,3-O-isopropylidene-L-threitol, MS: m/z 927.4 ([M+H]$^+$).

E. 1.63 g of 1,4-bis-O-[4'-(2,3:4,5-di-O-isopropylidene-D-arabinit-1-yloxy)-biphenyl-4-yl]-2,3-O-isopropylidene-L-threitol were dissolved in 50 ml of dioxan, treated with 15 ml of trifluoroacetic acid (70% in water) and stirred at reflux for 3 hours. After cooling to room temperature, the mixture was concentrated and the residue was treated twice with 50 ml of toluene and azeotropically distilled. The thus-obtained residue was taken up in 50 ml of water, stirred at room temperature for 1 hour, then cooled to 10° C. and filtered. After drying at 50° C. over phosphorus pentoxide, there was obtained 1,4-bis-O-(4'-D-arabinit-1-yloxy-biphenyl-4-yl)-L-threitol, elementary analysis calculated for $C_{38}H_{46}O_{14}$: C=6.80%, H=6.38%; found: C=63.12%, H=6.21%.

F. 1.09 g of 1,4-bis-O-(4'-D-arabinit-1-yloxy-biphenyl-4-yl)-L-threitol were reacted with sulfur trioxide-trimethylamine complex in analogy to Example 1.B. There was thus obtained 2,3-di-O-sulfo-1,4-bis-O-[4'-(2,3,4,5-tetra-O-sulfo-D-arabinit-1-yloxy)-biphenyl-4-yl]-L-threitol decasodium salt, MS: m/z 1746.0 (reconstructed M).

EXAMPLE 37

A. 1.37 g of 2,3:4,5-di-O-isopropylidene-1,6-bis-O-(4-methyl-phenylsulfonyl)-galactitol and 1.96 g of 1-O-(4'-hydroxy-biphenyl-4-yl)-2,3:4,5-di-O-isopropylidene-D-arabinitol (Example 36.C.) were reacted in analogy to Example 33.A. The crude product was chromatographed on silica gel with n-hexane and methylene chloride. There was obtained 1,6-bis-O-[4'-(2,3:4,5-di-O-isopropylidene-D-arabinit-1-yloxy)-biphenyl-4-yl]-2,3:4,5-di-O-isopropylidene-galactitol, MS: m/z 1026.5 ([M]$^+$).

B. 1.70 g of 1,6-bis-O-[4'-(2,3:4,5-di-O-isopropylidene-D-arabinit-1-yloxy)-biphenyl-4-yl]-2,3:4,5-di-O-isopropylidene-galactitol were reacted with trifluoroacetic acid (75%) in dioxan in analogy to Example 35.E. and worked up analogously. There was obtained 1,4-bis-O-(4'-D-arabinit-1-yloxy-biphenyl-4-yl)-galactitol, elementary analysis calculated for $C_{40}H_{50}O_{16}$: C=61.06%, H=6.41%; found: C=60.99%, H=6.50%.

C. 1.10 g of 1,4-bis-O-(4'-D-arabinit-1-yloxy-biphenyl-4-yl)-galactitol were reacted with sulfur trioxide-trimethylamine complex in analogy to Example 1.B. There was thus obtained 2,3,4,5-tetra-O-sulfo-1,6-bis-O-[4'-(2,3,4,5-tetra-O-sulfo-D-arabinit-1-yloxy)-biphenyl-4-yl]-galactitol dodecasodium salt, MS: m/z 2011.0 (reconstructed M).

EXAMPLE 38

A. 1.96 g of 1-O-(4'-hydroxy-biphenyl-4-yl)-2,3:4,5-di-O-isopropylidene-D-arabinitol (Example 36.C.) and 0.56 g of 1,2:5,6-dianhydro-3,4-O-isopropylidene-D-mannitol (Y. Le Merrer et al. Heterocyles 25, 541 (1987)) were stirred at 100° C. under argon for 6 hours in 130 ml of dimethylformamide with the addition of 4.15 g of potassium carbonate. The reaction mixture was poured on to ice-water, extracted with methylene chloride, the combined methylene chloride phases were washed with water, dried over magnesium sulfate, filtered and evaporated. The thus-obtained crude product was chromatographed on silica gel with hexane and ethyl acetate. There was thus obtained 1,6-bis-O-[4'-(2,3:4,5-di-O-isopropylidene-D-arabinit-1-yloxy)-biphenyl-4-yl]-3,4-O-isopropylidene-D-mannitol, MS: m/z 1010.6 ([M+Na]$^+$).

B. 1.60 g of 1,6-bis-O-[4'-(2,3:4,5-di-O-isopropylidene-D-arabinit-1-yloxy)-biphenyl-4-yl]-3,4-O-isopropylidene-D-mannitol were reacted with trifluoroacetic acid (50%) in dioxan in analogy to Example 35.E. There was obtained 1,6-bis-O-(4'-D-arabinit-1-yloxy-biphenyl-4-yl)-D-mannitol, IR: (KBr, cm$^{-1}$): 3381, 1607, 1499, 1242, 1176, 1045, 823.

C. 1.18 g of 1,6-bis-O-(4'-D-arabinit-1-yloxy-biphenyl-4-yl)-D-mannitol were reacted with sulfur trioxide-trimethylamine complex in analogy to Example 1.B. There was thus obtained 2,3,4,5-tetra-O-sulfo-1,6-bis-O-[4'-(2,3,4,5-tetra-O-sulfo-D-arabinit-1-yloxy)-biphenyl-4-yl]-D-mannitol dodecasodium salt, MS: m/z 2011.0 (reconstructed M).

EXAMPLE 39

A. 30.1 g of anisole and 26.0 g of 1,1-dichloro-2,2-diethoxy-ethane were reacted at 5° C. under argon with the addition of 42 ml of concentrated sulfuric acid. The reaction mixture was poured on to 350 ml of ice-water and thereafter suction filtered; the crystal slurry was washed with water and dried. The thus-obtained crude product was recrystallized from methylene chloride and n-hexane. There was thus obtained 4,4'-dimethoxy-1,1'-(2,2-dichloro-ethylidene)-dibenzene, m.p.: 113°–160° C.

B. 6.0 g of 4,4'-dimethoxy-1,1'-(2,2-dichloro-ethylidene)-dibenzene were heated at 190° C. with 9.7 g of potassium tert.-butylate. After the addition of ice-water, the mixture was filtered and the residue was washed with water and recrystallized from methylene chloride and n-hexane. There was obtained 4,4'-dimethoxy-1,1'-ethyndiyl-dibenzene, m.p.: 140°–142° C.

C. 16.4 g of 4,4'-dimethoxy-1,1'-ethyndiyl-dibenzene in 240 ml of methylene chloride were reacted with 12.6 ml of boron tribromide at −75° C. under argon. After hydrolysis, the product was isolated by extraction with ether. The organic phase was dried over magnesium sulfate, filtered and concentrated. The crude product was chromatographed on silica gel with n-hexane and ethyl acetate. There was thus obtained 4,4'-ethyndiyl-diphenol, MS: m/z 210.0 ($[M]^+$).

D. 2.56 g of 4,4'-ethyndiyl-diphenol and 4.71 g of 2,3:4,5-di-O-isopropylidene-1-O-(4-methyl-phenylsulfonyl)-D-arabinitol (Example 36.A.) were reacted at 60° C. for 70 hours in 500 ml of dimethylformamide with the addition of 8.43 g of potassium carbonate. The reaction mixture was subsequently poured on to ice-water, extracted with methylene chloride, the combined methylene chloride phases were washed with water, dried over magnesium sulfate, filtered and concentrated. The thus-obtained crude product was chromatographed on silica gel with methylene chloride and acetonitrile. There was obtained 1-O-[4-(4-hydroxy-phenylethynyl)-phenyl]-2,3:4,5-di-O-isopropylidene-D-arabinitol, MS: m/z 424.0 ($[M]^+$).

E. 2.12 g of 1-O-[4-(4-hydroxy-phenylethynyl)-phenyl]-2,3:4,5-di-O-isopropylidene-D-arabinitol and 1.43 g of 2,3:4,5-di-O-isopropylidene-1,6-bis-O-(4-methyl-phenylsulfonyl)-galactitol were reacted in analogy to Example 33.A. with the addition of 1.73 g of potassium carbonate and worked up. The crude product was chromatographed on silica gel with n-hexane and methylene chloride. There was obtained 1,6-bis-O-[4-[4-(2,3:4,5-di-O-isopropylidene-D-arabinit-1-yloxy)-phenylethynyl]-phenyl]-2,3:4,5-di-O-isopropylidene-galactitol, IR: (KBr, $cm^{-1}$): 2230, 1608, 1516, 1246, 1173, 1064, 1025, 836.

F. 1.80 g of 1,6-bis-O-[4-[4-(2,3:4,5-di-O-isopropylidene-D-arabinit-1-yloxy)-phenylethynyl]-phenyl]-2,3:4,5-di-O-isopropyl-idene-galactitol were reacted at reflux for 7 hours in analogy to Example 35.E. and subsequently worked up analogously. There was obtained 1,6-bis-O-[4-(4-D-arabinit-1-yloxy-phenylethynyl)-phenyl]-galactitol, which was used directly in the next step.

G. 1.40 g of 1,6-bis-O-[4-(4-D-arabinit-1-yloxy-phenylethynyl)-phenyl]-galactitol were reacted with sulfur trioxide-trimethylamine complex in analogy to Example 1.B. There was thus obtained 2,3,4,5-tetra-O-sulfo-1,6-bis-O-[4-[4-(2,3,4,5-tetra-O-sulfo-D-arabinit-1-yloxy)-phenyl-ethynyl]-phenyl]-galactitol dodecasodium salt, MS: m/z 2060.0 (reconstructed M).

EXAMPLE 40

A. 9.61 g of 2,3-dihydroxy-naphthalene were dissolved in 70 ml of 0.95M sodium methylate solution in methanol, treated with 6.92 ml of benzyl chloride and stirred at reflux for 4 hours. After cooling to room temperature, the mixture was worked up extractively with water, dilute hydrochloric acid and methylene chloride. The crude product was chromatographed on silica gel with n-hexane and methylene chloride. There was thus obtained 3-benzyloxy-naphthalen-2-ol, MS: m/z 250.0 ($[M]^+$).

B. 2.80 g of 3-benzyloxy-naphthalen-2-ol and 4.33 g of 2,3:4,5-di-O-isopropylidene-1-O-(4-methyl-phenylsulfonyl)-D-arabinitol (Example 36.A.) were reacted at 100° C. for 6 hours in analogy to Example 33.A. and worked up analogously. The thus-obtained crude product was chromatographed on silica gel with methylene chloride. The product was recrystallized from n-hexane. There was obtained 1-O-(3-benzyloxy-naphthalen-2-yl)-2,3:4,5-di-O-isopropylidene-D-arabinitol, MS: m/z 464.0 ($[M]^+$).

C. 4.80 g of 1-O-(3-benzyloxy-naphthalen-2-yl)-2,3:4,5-di-O-isopropylidene-D-arabinitol were hydrogenated in methanol at room temperature and normal pressure for 5 hours using 1.0 g of Pd charcoal (10%) as the catalyst. After filtration of the catalyst, the solvent was distilled off in a water-jet vacuum and the residue was chromatographed on silica gel with methylene chloride and methanol. There was obtained 1-O-(3-hydroxy-naphthalen-2-yl)-2,3:4,5-di-O-isopropylidene-D-arabinitol, MS: m/z 374.0 ($[M]^+$).

D. 1.10 g of 1-O-(3-hydroxy-naphthalen-2-yl)-2,3:4,5-di-O-isopropylidene-D-arabinitol and 0.84 g of 2,3:4,5-di-O-isopropyl-idene-1,6-bis-O-(4-methyl-phenylsulfonyl)-galactitol were reacted at 100° C. for 6 hours in analogy to Example 33.A. and worked up analogously. The crude product was chromatographed on silica gel with n-hexane and ethyl acetate. There was thus obtained 1,6-bis-O-[3-(2,3:4,5-di-O-isopropylidene-D-arabinit-1-yloxy)-naphthalen-2-yl]-2,3:4,5-di-O-isopropylidene-galactitol, IR: (film, $cm^{-1}$): 1628, 1510, 1256, 1216, 1176, .1096, 1017, 747.

E. 0.90 g of 1,6-bis-O-[3-(2,3:4,5-di-O-isopropylidene-D-arabinit-1-yloxy)-naphthalen-2-yl]-2,3:4,5-di-O-isopropylidene-galactitol was reacted with 10 ml of trifluoroacetic acid (70% in water) in 25 ml of dioxan in analogy to Example 35.E. After working up, there was obtained 1,6-bis-O-(3-D-arabinit-1-yloxy-naphthalen-2-yl)-galactitol which was used directly in the next step.

F. 0.83 g of 1,6-bis-O-(3-D-arabinit-1-yloxy-naphthalen-2-yl)-galactitol was reacted with sulfur trioxide-trimethylamine complex in analogy to Example 1.B. There was thus obtained 1,6-bis-O-[3-(2,3,4,5-tetra-O-sulfo-D-arabinit-1-yloxy)-naphthalen-2-yl]-2,3,4,5-tetra-O-sulfo-galactitol dodecasodium salt, MS: m/z 1960.0 (reconstructed M).

EXAMPLE 41

A. 1.53 g of 1-O-(3-hydroxy-naphthalen-2-yl)-2,3:4,5-di-O-isopropylidene-D-arabinitol (Example 40.C.) and 0.97 g of 2,3-O-isopropylidene-1,4-di-O-(4-methyl-phenylsulfonyl)-L-threitol were stirred at 100° C. for 21 hours analogously to Example 33.A. and worked up analogously. The crude product was chromatographed on silica gel with toluene and ethyl acetate. There was thus obtained 1,4-bis-O-[3-(2,3:4,5-di-O-isopropylidene-D-arabinit-1-yloxy)-naphthalen-2-yl]-2,3-O-isopropylidene-L-threitol which was used directly in the next step.

B. 0.65 g of 1,4-bis-O-[3-(2,3:4,5-di-O-isopropylidene-D-arabinit-1-yloxy)-naphthalen-2-yl]-2,3-O-isopropylidene-L-threitol was stirred at reflux for 7 hours in analogy to Example 35.E. and worked up analogously. There was obtained 1,4-bis-O-(3-D-arabinit-1-yloxy-naphthalen-2-yl)-L-threitol which was used directly in the next step.

C. 0.50 g of 1,4-bis-O-(3-D-arabinit-1-yloxy-naphthalen-2-yl)-L-threitol was reacted with sulfur trioxide-trimethylamine complex in analogy to Example 1.B. There was thus obtained 2,3-di-O-sulfo-1,4-bis-O-[3-(2,3,4,5-tetra-O-sulfo-D-arabinit-1-yloxy)-naphthalen-2-yl]-L-threitol decasodium salt, MS: m/z 1695.0 (reconstructed M).

EXAMPLE 42

0.50 g of 2,3,4,5-tetra-O-sulfo-1,6-bis-O-[4-[4-(2,3,4,5-tetra-O-sulfo-D-arabinit-1-yloxy)-phenylethynyl]-phenyl]-galactitol dodecasodium salt (Example 39.G.) was hydrogenated at normal pressure using 0.35 g of palladium on charcoal (10%) in 5 ml of water. After filtration of the catalyst, the filtrate was lyophilized. There was thus obtained 2,3,4,5-tetra-O-sulfo-1,6-bis-O-[4-[2-[4-(2,3,4,5-tetra-O-sulfo-D-arabinit-1-yloxy)-phenyl]-ethyl]-phenyl]-galactitol dodecasodium salt, MS: m/z 2067.0 (reconstructed M).

EXAMPLE 43

A. 30.00 g of bis-(4-hydroxy-phenyl)-methane were dissolved in 240 ml of 0.82M sodium ethylate solution in ethanol, treated with 19.80 ml of benzyl bromide and stirred at reflux for 4 hours. After cooling to room temperature, the mixture was worked up extractively with ice-water, dilute hydrochoric acid and methylene chloride. The thus-obtained crude product was chromatographed on silica gel with methylene chloride and ether. There was thus obtained 4-(4-benzyloxy-benzyl)-phenol, MS: m/z 290.0 ([M]$^+$).

B. 2.98 g of 1,2:5,6-dianhydro-3,4-O-isopropylidene-D-mannitol and 9.30 g of 4-(4-benzyloxy-benzyl)-phenol were stirred at for 100° C. for 17 hours in analogy to Example 33.A. and worked up analogously. The crude product was chromatographed on silica gel with n-hexane and ethyl acetate. The pure product was recrystallized from ethyl acetate and n-hexane. There was thus obtained 1,6-bis-O-[4-(4-benzyloxy-benzyl)-phenyl]-3,4-O-isopropylidene-D-mannitol, MS: m/z 784.4 ([M+NH$_4$]$^+$).

C. 6.07 g of 1,6-bis-O-[4-(4-benzyloxy-benzyl)-phenyl]-3,4-O-isopropylidene-D-mannitol were hydrogenated in 250 ml of ethyl acetate at normal pressure and room temperature with the addition of 2.0 g of palladium on charcoal (5%). After filtration of the catalyst, the solvent was distilled off in a water-jet vacuum and the residue was chromatographed on silica gel with methylene chloride and methanol. There was obtained 1,6-bis-O-[4-(4-hydroxy-benzyl)-phenyl]-3,4-O-isopropylidene-D-mannitol, MS: m/z 604.4 ([M+NH$_4$]$^+$).

D. 1.20 g of 1,6-bis-O-[4-(4-hydroxy-benzyl)-phenyl]-3,4-O-isopropylidene-D-mannitol and 1.58 g 2,3:4,5-di-O-isopropylidene-1-O-(4-methyl-phenylsulfonyl)-D-arabinitol (Example 36.A.) were stirred at 100° C. for 21 hours analogously to Example 33.A. and worked up analogously. The crude product was chromatographed on silica gel with methylene chloride and methanol. There was thus obtained 1,6-bis-O-[4-[4-(2,3:4,5-di-O-isopropylidene-D-arabinit-1-yloxy)-benzyl]-phenyl]-3,4-O-isopropylidene-D-mannitol, MS: m/z 1032.5 ([M+NH$_4$]$^+$).

E. 1.30 g of 1,6-bis-O-[4-[4-(2,3:4,5-di-O-isopropylidene-D-arabinit-1-yloxy)-benzyl]-phenyl]-3,4-O-isopropylidene-D-mannitol were stirred at reflux for 3 hours analogously to Example 35.E. After cooling to room temperature, the separated crystals were filtered off under suction and dried in a high vacuum at 50° C. over phosphorus pentoxide. There was obtained 1,6-bis-O-[4-(4-D-arabinit-1-yloxy-benzyl)-phenyl]-D-mannitol, MS: m/z 832.4 ([M+NH$_4$]$^+$).

F. 0.81 g of 1,6-bis-O-[4-(4-D-arabinit-1-yloxy-benzyl)-phenyl]-D-mannitol was reacted with sulfur trioxide-trimethylamine complex in analogy to Example 1.B. There was thus obtained 2,3,4,5-tetra-O-sulfo-1,6-bis-O-[4-[4-(2,3,4,5-tetra-O-sulfo-D-arabinit-1-yloxy)-benzyl]-phenyl]-D-mannitol dodecasodium salt, MS: m/z 2039.0 (reconstructed M).

EXAMPLE 44

A. 3.65 g of methyl 4-hydroxy-benzoate and 7.73 g of 2,3:4,5-di-O-isopropylidene-1-O-(4-methyl-phenylsulfonyl)-D-arabinitol (Example 36.A.) were reacted at 100° C. for 3 hours in 300 ml of dimethylformamide with the addition of 13.82 g of potassium carbonate analogously to Example 33.A. and worked up. The crude product was chromatographed on silica gel with methylene chloride and methanol. There was thus obtained 2,3:4,5-di-O-isopropylidene-1-O-(4-methoxycarbonyl-phenyl)-D-arabinitol, MS: m/z 366.0 ([M]$^+$).

B. 7.37 g of 2,3:4,5-Di-O-isopropylidene-1-O-(4-methoxycarbonyl-phenyl)-D-arabinitol were stirred at 50° C. for 16 hours with 20 ml of sodium hydroxide solution (28%) in 300 ml of methanol. After neutralization with 6N hydrochloric acid, the methanol was distilled off in a water-jet vacuum. The residue was poured on to ice-water, extracted with methylene chloride and the combined methylene chloride phases were washed with water, dried over magnesium sulfate, filtered and evaporated. The crude product was chromatographed on silica gel with methylene chloride and methanol. There was thus obtained 1-O-(4-carboxy-phenyl)-2,3:4,5-di-O-isopropylidene-D-arabinitol, MS: m/z 352.0 ([M]$^+$).

C. 17.60 g of 2,3:4,5-di-O-isopropylidene-1,6-bis-O-(4-methyl-phenylsulfonyl)-galactitol and 16.00 g of sodium azide were stirred at 100° C. for 1 hour in 300 ml of dimethylformamide. The reaction mixture was subsequently worked up extractively with ice-water and ethyl acetate. The thus-obtained crude product was recrystallized from methylene chloride and n-hexane. There was thus obtained 1,6-diazido-1,6-didesoxy-2,3:4,5-di-O-isopropylidene-galactitol, MS: m/z 297.0 ([M–CH$_3$]$^+$).

D. 9.20 g of 1,6-diazido-1,6-didesoxy-2,3:4,5-di-O-isopropylidene-galactitol were hydrogenated in 250 ml of methanol at room temperature and normal pressure with the addition of 2.50 g of palladium-charcoal (10%). After filtration of the catalyst, the solvent was distilled off in a water-jet vacuum. The residue was taken up in ethanol. Two equivalents of hydrochloric acid (in ethanol) were added, the mixture was again concentrated and the product was recrystallized from methanol and ether. There was thus obtained 1,6-diamino-1,6-didesoxy-2,3:4,5-di-O-isopropylidene-galactitol dihydrochloride, MS: m/z 245.0 ([M–CH$_3$]$^+$).

E. 1.41 g of 1-O-(4-carboxy-phenyl)-2,3:4,5-di-O-isopropylidene-D-arabinitol and 0.70 g of 2-chloro-4,6-dimethoxy-1,3,5-triazine were stirred at 0°–5° C. in 40 ml of acetonitrile/dimethylformamide (3:1) for 2 hours with the addition of 0.88 ml of 4-methyl-morpholine. Subsequently, 0.67 g of 1,6-diamino-1,6-didesoxy-2,3:4,5-di-O-isopropylidene-galactitol dihydrochloride was added and the mixture was stirred at room temperature for a further 18 hours. The reaction mixture was worked up extractively with ice-water and methylene chloride. The crude product was chromatographed on silica gel with methylene chloride and methanol. By recrystallization from methylene chloride and n-hexane there was obtained 1,6-didesoxy-2,3:4,5-di-O-isopropylidene-1,6-bis-[4-(2,3:4,5-di-O-isopropylidene-D-arabinit-1-yloxy)-benzoylamino]-galactitol, MS: m/z 929.3 ([M+H]$^+$).

F. 1.32 g of 1,6-didesoxy-2,3:4,5-di-O-isopropylidene-1,6-bis-[4-(2,3:4,5-di-O-isopropylidene-D-arabinit-1-yloxy)- benzoylamino]-galactitol were stirred in 21 ml of glacial acetic acid/water 2:1 at 100° C. for 4 hours. After cooling to room temperature, 30 ml of water were added and the mixture was filtered. The product was washed twice with 5 ml of water each time and then dried at 50° C. over phosphorus pentoxide in a high vacuum for 3 hours. There was thus obtained 1,6-bis-(4-D-arabinit-1-yloxy-benzoylamino)-1,6-didesoxy-galactitol, MS: m/z 711.6 ([M+Na]$^+$).

G. 0.90 g of 1,6-bis-(4-D-arabinit-1-yloxy-benzoylamino)-1,6-didesoxy-galactitol was reacted with sulfur trioxide-trimethylamine complex in analogy to Example 1.B. There was thus obtained 1,6-didesoxy-2,3,4,5-tetra-O-sulfo-1,6-bis-[4-(2,3,4,5-tetra-O-sulfo-D-arabinit-1-yloxy)-benzoylamino)-galactitol dodecasodium salt, MS: m/z 1912.0 (reconstructed M).

EXAMPLE 45

A. 4.85 g of methyl 3-hydroxy-2-naphthalene-2-carboxylate and 7.73 g of 2,3:4,5-di-O-isopropylidene-1-O-(4-methyl-phenylsulfonyl)-D-arabinitol (Example 36.A.) were reacted in 300 ml of dimethylformamide at 100° C. for 4 hours with the addition of 13.82 g of potassium carbonate analogously to Example 33.A. and worked up . The crude product was chromatographed on silica gel with methylene chloride and methanol. There was thus obtained 2,3:4,5-di-O-isopropylidene-1-O-(3-methoxycarbonyl-naphthalen-2-yl)-D-arabinitol, MS: m/z 416.0 ([M]$^+$).

B. 6.00 g of 2,3:4,5-di-O-isopropylidene-1-O-(3-methoxycarbonyl-naphthalen-2-yl)-D-arabinitol were stirred at room temperature for 16 hours with 14.4 ml of sodium hydroxide solution (28%) in 250 ml of methanol. After neutralization with 6N hydrochloric acid, the methanol was distilled off in a water-jet vacuum. The residue was poured on to ice-water, extracted with methylene chloride, the combined methylene chloride phases were washed with water, dried over magnesium sulfate, filtered and evaporated. The crude product was chromatographed on silica gel with methylene chloride and methanol. There was thus obtained 1-O-(3-carboxy-naphthalen-2-yl)-2,3:4,5-di-O-isopropylidene-D-arabinitol, MS: m/z 402.0 ([M]$^+$).

C. 1.61 g of 1-O-(3-carboxy-naphthalen-2-yl)-2,3:4,5-di-O-isopropylidene-D-arabinitol and 0.70 g of 2-chloro-4,6-dimethoxy-1,3,5-triazine were reacted with 0.67 g of 1,6-diamino-1,6-didesoxy-2,3:4,5-di-O-isopropylidene-galactitol dihydrochloride with the addition of 0.88 ml of 4-methyl-morpholine analogously to Example 44.E. and worked up. The crude product was chromatographed on silica gel with methylene chloride and methanol. There was thus obtained 1,6-didesoxy-2,3:4,5-di-O-isopropylidene-1,6-bis-[3-(2,3:4,5-di-O-isopropylidene-D-arabinit-1-yloxy)-naphthalen-2-ylcarbonylamino]-galactitol, MS: m/z 1028.8 ([M]$^+$).

D. 1.95 g of 1,6-didesoxy-2,3:4,5-di-O-isopropylidene-1,6-bis-[3-(2,3:4,5-di-O-isopropylidene-D-arabinit-1-yloxy)-naphthalen-2-ylcarbonylamino]-galactitol were reacted and worked up analogously to Example 44.F. There was obtained 1,6-bis-(3-D-arabinit-1-yloxy-naphthalen-2-ylcarbonylamino)-1,6-didesoxy-galactitol, MS: m/z 788.8 ([M]$^+$).

E. 1.11 g of 1,6-bis-(3-D-arabinit-1-yloxy-naphthalen-2-ylcarbonylamino)-1,6-didesoxy-galactitol were reacted with sulfur trioxide-trimethylamine complex in analogy to Example 1.b. There was thus obtained 1,6-didesoxy-2,3,4,5-tetra-O-sulfo-1,6-bis-[3-(2,3,4,5-tetra-O-sulfo-D-arabinit-1-yloxy)-naphthalen-2-ylcarbonylamino]-galactitol dodecasodium salt, MS: m/z 2013.0 (reconstructed M).

EXAMPLE 46

A. 27.75 g of 3,4-di-O-isopropylidene-D-mannitol and 65.25 g of dibutyltin oxide were stirred at reflux for 2 hours in 2.5 l of benzene using a water separator. Thereupon, the mixture was concentrated in a water-jet vacuum to a total volume of 700 ml. Subsequently, 46.25 g of tetrabutylammonium iodide were added at room temperature, 37.50 ml of 3-bromo-propyn-1-yne were added dropwise and the reaction mixture was stirred at 70° C. for 7 hours. After concentration in a water-jet vacuum, the crude product was chromatographed on silica gel with n-hexane and ethyl acetate. There was thus obtained 1,6-di-O-prop-2-ynyl-3,4-O-isopropylidene-D-mannitol, MS: m/z 298.0 ([M]$^+$).

B. 21.20 g of 1,6-di-O-prop-2-ynyl-3,4-O-isopropylidene-D-mannitol were stirred at 100° C. for 3 hours in 300 ml of glacial acetic acid/water 2:1. The reaction mixture was concentrated in a water-jet vacuum. 50 ml of toluene were added twice and the water was distilled off azeotropically each time. The residue was dried in a high vacuum over phosphorus pentoxide for 18 hours. There was thus obtained 1,6-bis-O-prop-2-ynyl-D-mannitol which was used directly in the next step.

C. 27.00 g of 1,6-bis-O-prop-2-ynyl-D-mannitol were dissolved in 300 ml of pyridine, treated at room temperature under argon with 100 ml of acetic anhydride and stirred for 4 hours. Subsequently, the mixture was worked up extractively with water and ethyl acetate. The thus-obtained crude product was chromatographed on silica gel with methylene chloride and methanol. There was thus obtained 2,3,4,5-tetra-O-acetyl-1,6-bis-O-prop-2-ynyl-D-mannitol, MS: m/z 367.0 ([M–OAc]$^+$).

D. 9.80 g of 4-iodo-phenol and 15.80 g of 2,3:4,5-di-O-isopropylidene-1-O-(4-methyl-phenylsulfonyl)-D-arabinitol (Example 36.A.) were reacted at 100° C. for 6 hours in 500 ml of dimethylformamide with the addition of 56.00 g of potassium carbonate and worked up analogously to Example 33.A. The crude product was chromatographed on silica gel with hexane and ethyl acetate. There was thus obtained 1-O-(4-iodophenyl)-2,3:4,5-di-O-isopropylidene-D-arabinitol, MS: m/z 434.0 ([M]$^+$).

E. 14.90 g of 1-O-(4-iodo-phenyl)-2,3:4,5-di-O-isopropylidene-D-arabinitol were reacted and worked up analogously to Example 46.B. The crude product was suspended in ether, filtered and dried over phosphorus pentoxide in a high vacuum at 50° C. for 16 hours. The thus-obtained 1-O-(4-iodo-phenyl)-D-arabinitol was used directly in the next step.

F. 12.85 g of 1-O-(4-iodo-phenyl)-D-arabinitol were reacted and worked up analogously to Example 46.C. The crude product was recrystallized from ethyl acetate and hexane. There was thus obtained 2,3,4,5-tetra-O-acetyl-1-O-(4-iodo-phenyl)-D-arabinitol, MS: m/z 522.0 ([M]$^+$).

G. 2.61 g of 2,3,4,5-tetra-O-acetyl-1-O-(4-iodo-phenyl)-D-arabinitol, 0.58 g of palladium(O)-tetrakis-triphenylphosphine and 0.19 g of copper(I) iodide were stirred at room temperature under argon in 25 ml of diisopropylamine/dimethylformamide (1:1) for 45 minutes. Subsequently, a solution of 1.07 g of 2,3,4,5-tetra-O-acetyl-1,6-bis-O-prop-2-ynyl-D-mannitol in 10 ml of diisopropylamine/dimethylformamide (1:1) was added dropwise and the reaction mixture was stirred at room temperature for 70 hours. The mixture was thereupon concentrated with the addition of 100 ml of toluene and the dimethylformamide was then distilled off in a high vacuum. The thus-obtained crude product was chromatographed on silica gel with methylene chloride and methanol. There was thus obtained 2,3,4,5-tetra-O-acetyl-1,6-bis-O-[3-[4-(2,3,4,5-tetra-O-acetyl-D-arabinit-1-yloxy)-phenyl]-prop-2-ynyl]-D-mannitol which was used directly in the next step.

H. 3.42 g of 2,3,4,5-tetra-O-acetyl-1,6-bis-O-[3-[4-(2,3,4,5-tetra-O-acetyl-D-arabinit-1-yloxy)-phenyl]-prop-2-ynyl]-D-mannitol were dissolved in 100 ml of methanol, treated with 10 ml of sodium methylate solution (5.4 molar) and stirred at room temperature for 16 hours. The reaction solution was adjusted to pH 2–3 with aqueous hydrochloric acid and concentrated. The residue was suspended in water and filtered, and the residue was washed twice with 10 ml of water each time and dried over phosphorus pentoxide in a high vacuum for 5 hours. There was thus obtained 1,6-bis-O-[3-(4-D-arabinit-1-yloxy-phenyl)-prop-2-ynyl]-D-mannitol, MS: m/z 733.6 ([M+Na]$^+$).

I. 1.70 g of 1,6-bis-O-[3-(4-D-arabinit-1-yloxy-phenyl)-prop-2-ynyl]-D-mannitol were reacted with sulfur trioxide-trimethylamine complex in analogy to Example 1.B. There was thus obtained 2,3,4,5-tetra-O-sulfo-1,6-bis-O-[3-[4-(2,3,4,5-tetra-O-sulfo-D-arabinit-1-yloxy)-phenyl]-prop-2-ynyl]-D-mannitol dodecasodium salt, MS: m/z 1934.0 (reconstructed M).

EXAMPLE 47

A. 14.10 g of 2,3-O-isopropylidene-1,4-bis-O-(4-methyl-phenylsulfonyl)-L-threitol and 6.00 g of 4-benzyloxy-phenol were dissolved in 300 ml of dimethylformamide, treated with 20.70 g of potassium carbonate and stirred at 100° C. for 6 hours. The reaction mixture was worked up extractively with ice-water and methylene chloride. The crude product was subsequently chromatographed on silica gel with n-hexane and methylene chloride. There was thus obtained 1-O-(4-benzyloxy-phenyl)-2,3-O-isopropylidene-4-O-(4-methyl-phenylsulfonyl)-L-threitol, MS: m/z 498.0 ([M]$^+$).

B. 5.81 g of 4-(4-benzyloxy-benzyl)-phenol (Example 43.A.) and 7.73 g of 2,3:4,5-di-O-isopropylidene-1-O-(4-methyl-phenyl-sulfonyl)-D-arabinitol were reacted at 100° C. in dimethylformamide analogously to Example 47.A. and worked up analogously. The crude product was chromatographed on silica gel with n-hexane and methylene chloride. There was thus obtained 1-O-[4-(4-benzyloxy-benzyl)-phenyl]-2,3:4,5-di-O-isopropylidene-D-arabinitol, MS: m/z 504.0 ([M]$^+$).

C. 8.30 g of 1-O-[4-(4-benzyloxy-benzyl)-phenyl]-2,3:4,5-di-O-isopropylidene-D-arabinitol were hydrogenated in 85 ml of tetrahydrofuran at normal pressure and room temperature with the addition of 1.60 g of palladium on charcoal (10%). After filtration of the catalyst, the filtrate was concentrated. There was thus obtained 1-O-[4-(4-hydroxy-benzyl)-phenyl]-2,3:4,5-di-O-isopropylidene-D-arabinitol, MS: m/z 414.0 ([M]$^+$).

D. 1.66 g of 1-O-[4-(4-hydroxy-benzyl)-phenyl]-2,3:4,5-di-O-isopropylidene-D-arabinitol and 1.99 g of 1-O-(4-benzyloxy-phenyl)-2,3-O-isopropylidene-4-O-(4-methyl-phenylsulfonyl)-L-threitol were reacted at 100° C. in dimethylformamide analogously to Example 47.A. and worked up analogously. The crude product was chromatographed on silica gel with n-hexane and methylene chloride. There was thus obtained 1-O-(4-benzyloxy-phenyl)-4-O-[4-[4-(2,3:4,5-di-O-isopropylidene-D-arabinit-1-yloxy)-benzyl]-phenyl]-L-threitol, MS: m/z 740.0 ([M]$^+$).

E. 2.50 g of 1-O-(4-benzyloxy-phenyl)-4-O-[4-[4-(2,3:4,5-di-O-isopropylidene-D-arabinit-1-yloxy)-benzyl]-phenyl]-L-threitol were hydrogenated and worked up analogously to Example 47.C. There was thus obtained 1-O-(4-hydroxy-phenyl)-4-O-[4-[4-(2,3:4,5-di-O-isopropylidene-D-arabinit-1-yloxy)-benzyl]-phenyl]-L-threitol, MS: m/z 650.0 ([M]$^+$).

F. 1.80 g of 1-O-(4-hydroxy-phenyl)-4-O-[4-[4-(2,3:4,5-di-O-isopropylidene-D-arabinit-1-yloxy)-benzyl]-phenyl]-L-threitol and 0.79 g of 2,3:4,5-di-O-isopropylidene-1,6-bis-O-(4-methyl-phenylsulfonyl)-galactitol were reacted at reflux in 20 ml of dimethylformamide for 3 hours in analogy to Example 47.A. and worked up analogously. The crude product was chromatographed on silica gel with toluene and ethyl acetate. There was obtained 1,6-bis-O-[4-[4-O-[4-[4-(2,3:4,5-di-O-isopropylidene-D-arabinit-1-yloxy)-benzyl]-phenyl]-2,3-di-O-isopropylidene-L-threit-1-yloxy]-phenyl]-2,3:4,5-di-O-isopropylidene-galactitol which was used directly in the next step.

G. 0.35 g of 1,6-bis-O-[4-[4-O-[4-[4-(2,3:4,5-di-O-isopropylidene-D-arabinit-1-yloxy)-benzyl]-phenyl]-2,3-di-O-isopropyldene-L-threit-1-yloxy]-phenyl]-2,3:4,5-di-O-isopropylidene-galactitol was stirred at reflux for 3 hours in analogy to Example 35.E. and worked up analogously. There was thus obtained 1,6-bis-O-[4-[4-O-[4-[4-(D-arabinit-1-yloxy)-benzyl]-phenyl]-L-threit-1-yloxy]-phenyl]-galactitol which was used directly in the next step.

H. 0.27 g of 1,6-bis-O-[4-[4-O-[4-[4-(D-arabinit-1-yloxy)-benzyl]-phenyl]-L-threit-1-yloxy]-phenyl]-galactitol was reacted with sulfur trioxide-trimethylamine complex in analogy to Example 1.B. There was thus obtained 2,3,4,5-tetra-O-sulfo-1,6-bis-O-[4-[4-O-[4-[4-(2,3,4,5-tetra-O-sulfo-D-arabinit-1-yloxy)-benzyl]-phenyl]-2,3-di-O-sulfo-L-threit-1-yloxy]-phenyl]-galactitol hexadecasodium salt, MS: m/z 2840.0 (reconstructed M).

EXAMPLE 48

A. 5.0 g of 2,3:4,5-di-O-isopropylidene-1,6-bis-O-(4-methyl-phenylsulfonyl)-galactitol, 5.26 g of 4-benzyloxy-phenol and 3.6 g of finely ground anhydrous potassium carbonate were suspended in 60 ml of dimethylformamide and stirred at 130° C. under argon for 18 hours. Subsequently, the reaction mixture was diluted with water and the thus-formed crystals were filtered off. There was obtained 1,6-bis-O-(4-benzyloxy-phenyl)-2,3:4,5-di-O-isopropylidene-galactitol in the form of colorless crystals, MS: m/z 625 ([M–H]$^+$).

B. 4.0 g of 1,6-bis-O-(4-benzyloxy-phenyl)-2,3:4,5-di-O-isopropylidene-galactitol were exhaustively hydrogenated in 150 ml of tetrahydrofuran in a hydrogen atmosphere with the addition of 0.5 g of palladium on charcoal (10%). Subsequently, the reaction mixture was filtered over a 0.8µ cellulose filter. The filtrate was concentrated and the residue was crystallized from ether; there was thus obtained 1,6-bis-O-(4-hydroxy-phenyl)-2,3:4,5-di-O-isopropylidene-galactitol as a colorless solid, MS: m/z 446 ([M]$^+$).

C. 1.78 g of 1,6-bis-O-(4-hydroxy-phenyl)-2,3:4,5-di-O-isopropylidene-galactitol, 3.2 g of 1-O-benzyl-2,3-O-isopropylidene-4-O-(4-methyl-phenylsulfonyl)-D-threitol (E. Hungerbühler & D. Seebach, Helvetica Chimica Acta 64, 687 (1981)) and 1.2 g of finely ground anhydrous potassium carbonate were suspended in 25 ml of dimethylformamide and stirred at 130° C. under argon for 24 hours. The reaction mixture was subsequently diluted with water and the aqueous phase was extracted with ether. The combined ether phases were dried over magnesium sulfate and concentrated. The thus-obtained crude product was chromatographed on silica gel with 5% ether in methylene chloride. There was thus obtained 1,6-bis-O-[4-(4-O-benzyl-2,3-O-isopropylidene-D-threit-1-yloxy)-phenyl]-2,3:4,5-di-O-isopropylidene-galactitol in the form of colorless crystals, MS: m/z 932.6 ([M+NH$_4$]$^+$).

D. 2.3 g of 1,6-bis-O-[4-(4-O-benzyl-2,3-O-isopropylidene-D-threit-1-yloxy)-phenyl]-2,3:4,5-di-O-isopropylidene-galactitol were exhaustively hydrogenated in 20 ml of tetrahydrofuran in a hydrogen atmosphere with the addition of 0.2 g of palladium on charcoal (10%). Subsequently, the reaction mixture was filtered over a 0.8μ cellulose filter and concentrated; there was thus obtained 2,3:4,5-di-O-isopropylidene-1,6-bis-O-[4-(2,3-O-isopropylidene-D-threit-1-yloxy)-phenyl]-galactitol as a colorless oil, MS: m/z 734 ([M]$^+$).

E. 1.74 g of 2,3:4,5-di-O-isopropylidene-1,6-bis-O-[4-(2,3-O-isopropylidene-D-threit-1-yloxy)-phenyl]-galactitol dissolved in 15 ml of pyridine were treated at 0° C. with a solution of 1.35 g of p-toluenesulfonyl chloride in 5 ml of pyridine and stirred at room temperature for 60 hrs. Thereupon, the reaction mixture was treated with ice-water, stirred at room temperature for 1.5 hours and extracted with ether. The combined ether phases were washed with 1N hydrochloric acid and water, dried over magnesium sulfate and concentrated. The thus-obtained crude product was chromatographed on silica gel with 5% ether in methylene chloride. There was thus obtained 2,3:4,5-di-O-isopropylidene-1,6-bis-O-[4-[2,3-O-isopropylidene-4-O-(4-methyl-phenyl-sulfonyl)-D-threit-1-yloxy]-phenyl]-galactitol as a colorless oil, MS: m/z 870 ([M–TosOH]$^+$).

F. 2.21 g of 2,3:4,5-di-O-isopropylidene-1,6-bis-O-[4-[2,3-O-isopropylidene-4-O-(4-methyl-phenyl-sulfonyl)-D-threit-1-yloxy]-phenyl]-galactitol, 1.13 g of methyl (E)-3-(4-hydroxy-phenyl)-acrylate and 0.87 g of finely ground anhydrous potassium carbonate were suspended in 10 ml of dimethyl-formamide and stirred at 130° C. under argon for 20 hours. Subsequently, the reaction mixture was concentrated, diluted with water and extracted with methylene chloride. The combined methylene chloride phases were washed with 1N sodium hydroxide solution and water, dried over magnesium sulfate and concentrated. The thus-obtained crude product, 2,3:4,5-di-O-isopropylidene-1,6-bis-O-[4-[2,3-O-isopropylidene-4-O-[(E)-2-methoxycarbonyl-vinyl]-phenyl]-D-threit-1-yloxy]-phenyl]-galactitol, was thereupon dissolved in 30 ml of methanol, treated with 3 ml of concentrated sodium hydroxide solution and 3 ml of water and heated under reflux for 3 hours. Thereupon, the mixture was acidified with 1N hydrochloric acid while cooling with ice and the thus-obtained precipitate was filtered off. There was thus obtained 1,6-bis-O-[4-[4-O-[4-[(E)-2-carboxy-vinyl]-phenyl]-2,3-O-isopropylidene-D-threit-1-yloxy]-phenyl]-2,3:4,5-di-O-isopropylidene-galactitol in form of colorless crystals, MS: m/z 1025.4 ([M–H]$^-$).

G. 1.02 g of 1,6-bis-O-[4-[4-O-[4-[(E)-2-carboxy-vinyl]-phenyl]-2,3-O-isopropylidene-D-threit-1-yloxy]-phenyl]-2,3:4,5-di-O-isopropylidene-galactitol dissolved in 5 ml of dimethylformamide were treated with 0.3 ml of 4-methylmorpholine at 0°–5° C. with the exclusion of moisture and stirred intensively for 10 minutes. Thereupon, 0.40 g of solid 2-chloro-4,6-dimethoxy-1,3,5-triazine was added and the mixture was stirred at 0°–5° C. for a further 2 hours. Subsequently, 0.40 g of D-glucamine was added and the mixture was stirred at room temperature for a further 18 hours. Thereupon, the reaction mixture was diluted with water and concentrated, the residue was treated with water and the mixture was boiled briefly and filtered. There was thus obtained 1,6-bis-O-[4-[4-O-[4-[(E)-2-D-glucit-1-ylcarbamoyl-vinyl]-phenyl]-2,3-O-iso-propylidene-D-threit-1-yloxy]-phenyl]-2,3:4,5-di-O-isopropylidene-galactitol as a brownish solid, MS: m/z 1353.6 ([M+H]$^+$).

H. 0.20 g of 1,6-bis-O-[4-[4-O-[4-[(E)-2-D-glucit-1-ylcarbamoyl-vinyl]-phenyl]-2,3-O-isopropylidene-D-threit-1-yloxy]-phenyl]-2,3:4,5-di-O-isopropylidene-galactitol was suspended in 3 ml of dioxan, 0.5 ml of trifluoroacetic acid and 0.7 ml of water and heated under reflux at 95° C. for 18 hours. Subsequently, the reaction mixture was concentrated to dryness; there was thus obtained 1,6-bis-O-[4-[4-O-[4-[(E)-2-D-glucit-1-ylcarbamoyl-vinyl]-phenyl]-D-threit-1-yloxy]-phenyl]-galactitol as a colorless solid, MS: m/z 1215.9 ([M+Na]$^+$).

I. The 1,6-bis-O-[4-[4-O-[4-[(E)-2-D-glucit-1-ylcarbamoyl-vinyl]-phenyl]-D-threit-1-yloxy]-phenyl]-galactitol obtained above was converted analogously to Example 1.B. into 1,6-bis-O-[4-[4-O-[4-[(E)-2-(2,3,4,5,6-penta-O-sulfo-D-glucit-1-ylcarbamoyl)-vinyl]-phenyl]-2,3-di-O-sulfo-D-threit-1-yloxy]-phenyl]-2,3,4,5-tetra-O-sulfo-galactitol octadecasodium salt, [a]–3.6° (c 0.7; water).

EXAMPLE 49

A. 0.15 g of 1,6-bis-O-[4-[4-O-[4-[(E)-2-(2,3,4,5,6-penta-O-sulfo-D-glucit-1-ylcarbamoyl)-vinyl]-phenyl]-2,3-di-O-sulfo-D-threit-1-yloxy]-phenyl]-2,3,4,5-tetra-O-sulfo-galactitol octadecasodium salt in 5 ml of distilled water was exhaustively hydrogenated in a hydrogen atmosphere with the addition of 100 mg of palladium on charcoal (10%). Subsequently, the reaction mixture was filtered over a 0.8μ cellulose filter and the filtrate was lyophilized; there was thus obtained 1,6-bis-O-[4-[4-O-[4-[2-(2,3,4,5,6-penta-O-sulfo-D-glucit-1-ylcarbamoyl)-ethyl]-phenyl]-2,3-di-O-sulfo-D-threit-1-yloxy]-phenyl]-2,3,4,5-tetra-O-sulfo-galactitol octadecasodium salt, [a]–3.4° (c 0.5; water).

EXAMPLE 50

A. 37.6 g of 2,3-O-isopropylidene-1,4-di-O-(4-methyl-phenyl-sulfonyl)-L-threitol, 16.0 g of methyl 3-hydroxy-naphthalene-2-carboxylate and 13 g of finely ground anhydrous potassium carbonate were suspended in 300 ml of acetonitrile and stirred at 100° C. under argon for 60 hours. Subsequently, the reaction mixture was diluted with water and the aqueous phase was extracted with ether. The combined ether phases were dried over magnesium sulfate and concentrated. The thus-obtained crude product was chromatographed on silica gel with ether in methylene chloride. There was thus obtained crude 2,3-O-isopropylidene-1-O-(3-methoxycarbonyl-naphthalen-2-yl)-4-O-(4-methyl-phenylsulfonyl)-L-threitol. This was dissolved in 100 ml of dimethylformamide and, after the addition of 15.6 g of 4-benzyloxy-phenol and 15.6 g of finely ground anhydrous potassium carbonate, stirred at 130° C. under argon for 18 hours. The reaction mixture was subsequently diluted with water and the aqueous phase was extracted with ether. The combined ether phases were dried over magnesium sulfate and concentrated. The thus-obtained crude product was chromatographed on silica gel with ether in methylene chloride.

There were thus obtained 15.6 g of 1-O-(4-benzyloxy-phenyl)-2,3-O-isopropylidene-4-O-(3-methoxycarbonyl-naphthalen-2-yl)-L-threitol as a colorless oil, MS: m/z 528 ([M]+).

B. 1.72 g of 1-O-(4-benzyloxy-phenyl)-2,3-O-isopropylidene-4-O-(3-methoxycarbonyl-naphthalen-2-yl)-L-threitol in 40 ml of tetrahydrofuran were exhaustively hydrogenated in a hydrogen atmosphere with the addition of 0.2 g of palladium on charcoal (10%). Subsequently, the reaction mixture was filtered over a 0.8µ cellulose filter and the filtrate was concentrated; there was thus obtained 1-O-(4-hydroxy-phenyl)-2,3-O-isopropylidene-4-O-(3-methoxycarbonyl-naphthalen-2-yl)-L-threitol as a colorless oil, MS: m/z 438 ([M]+).

C. 0.57 g of 2,3:4,5-di-O-isopropylidene-1,6-bis-O-(4-methyl-phenylsulfonyl)-galactitol, 0.95 g of 1-O-(4-hydroxy-phenyl)-2,3-O-isopropylidene-4-O-(3-methoxycarbonyl-naphthalen-2-yl)-L-threitol and 0.3 g of finely ground anhydrous potassium carbonate were suspended in 10 ml of acetonitrile and stirred at 130° C. under argon for 100 hours. The reaction mixture was subsequently diluted with water and the aqueous phase was extracted with methylene chloride. The combined methylene chloride phases were dried over magnesium sulfate and concentrated. The thus-obtained crude product was chromatographed on silica gel with ether in methylene chloride. There was thus obtained 2,3:4,5-di-O-isopropylidene-1,6-bis-O-[4-[2,3-O-isopropylidene-4-O-(3-methoxycarbonyl-naphthalen-2-yl)-L-threit-1-yloxy]-phenyl]-galactitol as a colorless solid, MS: m/z 1120.4 ([M–NH$_4$]+).

D. 0.58 g of 2,3:4,5-di-O-isopropylidene-1,6-bis-O-[4-[2,3-O-isopropylidene-4-O-(3-methoxycarbonyl-naphthalen-2-yl)-L-threit-1-yloxy]-phenyl]-galactitol was dissolved in 5 ml of 2-methoxy-ethanol, treated with 5 ml of concentrated sodium hydroxide solution and heated under reflux for 5 hours. Thereupon, the mixture was acidified with 1N hydrochloric acid while cooling with ice, extracted with methylene chloride and the combined methylene chloride phases were dried over magnesium sulfate and concentrated. The thus-obtained crude product was chromatographed on silica gel with methanol in methylene chloride. There was thus obtained 1,6-bis-O-[4-[4-O-(3-carboxy-naphthalen-2-yl)-2,3-O-isopropylidene-L-threit-1-yloxy]-phenyl]-2,3:4,5-di-O-isopropylidene-galactitol as a colorless solid, MS: m/z 1073.2 ([M–H]).

E. 0.30 g of 1,6-bis-O-[4-[4-O-(3-carboxy-naphthalen-2-yl)-2,3-O-isopropylidene-L-threit-1-yloxy]-phenyl]-2,3:4,5-di-O-isopropylidene-galactitol dissolved in 3 ml of dimethylformamide was treated with 0.7 ml of 4-methylmorpholine at 0°–5° C. with the exclusion of moisture and stirred intensively for 10 minutes. Thereupon, 0.105 g of solid 2-chloro-4,6-dimethoxy-1,3,5-triazine was added and the mixture was stirred at 0°–5° C. for a further 2 hours. Subsequently, 0.109 g of D-glucamine was added and the mixture was stirred at room temperature for a further 18 hours. Thereupon, the reaction mixture was diluted with water and concentrated, the residue was treated with water and the mixture was boiled briefly and filtered. There was thus obtained 1,6-bis-O-[4-[4-O-(3-D-glucit-1-ylcarbamoyl-naphthalen-2-yl)-2,3-O-isopropylidene-L-threit-1-yloxy]-phenyl]-2,3:4,5-di-O-iso-propylidene-galactitol as a colorless solid, MS: m/z 1401.7 ([M+H]+).

F. 0.34 g of 1,6-bis-O-[4-[4-O-(3-D-glucit-1-ylcarbamoyl-naphthalen-2-yl)-2,3-O-isopropylidene-L-threit- 1-yloxy]-phenyl]-2,3:4,5-di-O-isopropylidene-galactitol was suspended in 4 ml of dioxan, 0.5 ml of trifluoroacetic acid and 0.3 ml of water and heated under reflux at 110° C. for 18 hours. Subsequently, the reaction mixture was concentrated to dryness; there was thus obtained 1,6-bis-O-[4-[4-O-(3-D-glucit-1-ylcarbamoyl-naphthalen-2-yl)-L-threit-1-yloxy]-phenyl]-galactitol as a colorless solid, MS: m/z 1242.7 ([M+H]+).

G. The 1,6-bis-O-[4-[4-O-(3-D-glucit-1-ylcarbamoyl-naphthalen-2-yl)-L-threit-1-yloxy]-phenyl]-galactitol obtained above was converted analogously to Example 1.B. into 1,6-bis-O-[4-[4-O-[3-(2,3,4,5,6-penta-O-sulfo-D-glucit-1-ylcarbamoyl)-naphthalen-2-yl]-2,3-di-O-sulfo-L-threit-1-yloxy]-phenyl]-2,3,4,5-tetra-O-sulfo-galactitol octadecasodium salt, [a]+2.3° (c 0.6; water), MS: m/z 3075.0 (reconstructed M).

EXAMPLE 51

A. 5.0 g of bis-(4-hydroxy-phenyl)-methane were dissolved in 40 ml of ethanol, 33 ml of 1 molar sodium ethanolate solution in ethanol and subsequently 3.6 ml of benzyl chloride were added and the reaction mixture was heated under reflux with the exclusion of moisture for 4 hours. Thereupon, the mixture was acidified with 1N hydrochloric acid while cooling with ice, extracted with methylene chloride and the combined methylene chloride phases were dried over magnesium sulfate and concentrated. The thus-obtained crude product was chromatographed on silica gel with ether in methylene chloride. There was thus obtained 4-(4-benzyloxy-benzyl)-phenol in the form of colorless crystals, MS: m/z 290 ([M]+).

B. 6.0 g of 2,3-O-isopropylidene-1,4-di-O-(4-methyl-phenyl-sulfonyl)-L-threitol, 2.13 g of methyl 4-hydroxybenzoate and 1.94 g of finely ground anhydrous potassium carbonate were suspended in 100 ml of acetonitrile and stirred at 100° C. under argon for 18 hours. Subsequently, the reaction mixture was diluted with water, extracted with methylene chloride and the combined methylene chloride phases were dried over magnesium sulfate and concentrated. The residue was chromatographed on silica gel with 5% ether in methylene chloride. There was thus obtained 2,3-O-isopropylidene-1-O-(4-methoxycarbonyl-phenyl)-4-O-(4-methyl-phenylsulfonyl)-L-threitol as a colorless oil, MS: m/z 450 ([M]+).

C. 2.54 g of 2,3-O-isopropylidene-1-O-(4-methoxycarbonyl-phenyl)-4-O-(4-methyl-phenylsulfonyl)-L-threitol, 1.80 g 4-(4-benzyloxy-benzyl)-phenol and 0.86 g of finely ground anhydrous potassium carbonate were suspended in 10 ml of dimethylformamide and stirred at 130° C. under argon for 18 hours. Subsequently, the reaction mixture was diluted with water and extracted with methylene chloride. The combined methylene chloride phases were dried over magnesium sulfate, concentrated and the residue was chromatographed on silica gel with methylene chloride. There was thus obtained 1-O-[4-(4-benzyloxy-benzyl)-phenyl]-2,3-O-isopropylidene-4-O-(4-methoxycarbonyl-phenyl)-L-threitol as a colorless solid, MS: m/z 568 ([M]+).

D. 2.1 g of 1-O-[4-(4-benzyloxy-benzyl)-phenyl]-2,3-O-isopropylidene-4-O-(4-methoxycarbonyl-phenyl)-L-threitol were exhaustively hydrogenated in 40 ml of tetrahydrofuran in a hydrogen atmosphere with the addition of 0.2 g of palladium on charcoal (10%). Subsequently, the reaction mixture was filtered over a 0.8µ cellulose filter, the filtrate was concentrated and chromatographed with 5% ether in methylene chloride; there was thus obtained 1-O-[4-(4-hydroxy-benzyl)-phenyl]-2,3-O-iso-propylidene-4-O-(4-methoxycarbonyl-phenyl)-L-threitol as a colorless solid, MS: m/z 478 ([M]+).

E. 0.8 g of 2,3:4,5-di-O-isopropylidene-1,6-bis-O-(4-methyl-phenylsulfonyl)-galactitol, 1.47 g of 1-O-[4-(4-hydroxy-benzyl)-phenyl]-2,3-O-isopropylidene-4-O-(4-methoxycarbonyl-phenyl)-L-threitol and 0.42 g of finely ground anhydrous potassium carbonate were suspended in 10 ml of acetonitrile and stirred under reflux and under argon for 200 hours. Subsequently, the reaction mixture was diluted with water, extracted with methylene chloride and the combined methylene chloride phases were dried over magnesium sulfate and concentrated. The residue was chromatographed on silica gel with 7% ether in methylene chloride. There was thus obtained 2,3:4,5-di-O-isopropylidene-1,6-bis-O-[4-[4-[4-O-(4-methoxycarbonyl-phenyl)-2,3-O-isopropylidene-L-threit-1-yloxy]-benzyl]-phenyl]-galactitol in the form of colorless crystals, MS: m/z 1207.1 ([M+Na]+).

F. 1.05 g of 2,3:4,5-di-O-isopropylidene-1,6-bis-O-[4-[4-[4-O-(4-methoxycarbonyl-phenyl)-2,3-O-isopropylidene-L-threit-1-yloxy]-benzyl]-phenyl]-galactitol were dissolved in 10 ml of 2-methoxyethanol, treated with 1 ml of concentrated sodium hydroxide solution and 5 ml of water and heated under reflux for 5 hours. Thereupon, the mixture was acidified with 1N hydrochloric acid while cooling with ice and the precipitate formed was filtered off. There was thus obtained 1,6-bis-O-[4-[4-[4-O-(4-carboxy-phenyl)-2,3-O-isopropylidene-L-threit-1-yloxy]-benzyl]-phenyl]-2,3:4,5-di-O-isopropylidene-galactitol as a colorless solid, MS: m/z 1178.1 ([M+Na]+).

G. 0.6 g of 1,6-bis-O-[4-[4-[4-O-(4-carboxy-phenyl)-2,3-O-isopropylidene-L-threit-1-yloxy]-benzyl]-phenyl]-2,3:4,5-di-O-isopropylidene-galactitol dissolved in 5 ml of dimethylformamide was treated with 0.13 ml of 4-methylmorpholine at 0°–5° C. with the exclusion of moisture and stirred intensively for 10 minutes. Thereupon, 0.20 g of solid 2-chloro-4,6-dimethoxy-1,3,5-triazine was added and the mixture was stirred at 0°–5° C. for a further 2 hours. Subsequently, 0.21 g of D-glucamine was added and the mixture was stirred at room temperature for a further 18 hours. Thereupon, the reaction mixture was diluted with water and concentrated, the residue was treated with water and the mixture was boiled briefly and filtered. There was thus obtained 1,6-bis-O-[4-[4-[4-O-(4-D-glucit-1-ylcarbamoyl-phenyl)-2,3-O-isopropylidene-L-threit-1-yloxy]-benzyl]-phenyl]-2,3:4,5-di-O-isopropylidene-galactitol as a colorless solid, MS: m/z 1481.0 ([M]+).

H. 0.7 g of 1,6-bis-O-[4-[4-[4-O-(4-D-glucit-1-ylcarbamoyl-phenyl)-2,3-O-isopropylidene-L-threit-1-yloxy]-benzyl]-phenyl]-2,3:4,5-di-O-isopropylidene-galactitol was suspended in 5 ml of dioxan, 1 ml of trifluoroacetic acid and 1 ml of water and heated under reflux at 100° C. for 18 hours. Subsequently, the reaction mixture was concentrated to dryness, suspended in water and filtered; there was thus obtained 1,6-bis-O-[4-[4-[4-O-(4-D-glucit-1-ylcarbamoyl-phenyl)-L-threit-1-yloxy]-benzyl]-phenyl]-galactitol as a colorless solid, MS: m/z 1344.3 ([M+Na]+).

I. The 1,6-bis-O-[4-[4-[4-O-(4-D-glucit-1-ylcarbamoyl-phenyl)-L-threit-1-yloxy]-benzyl]-phenyl]-galactitol obtained above was converted analogously to Example 1.B. into 1,6-bis-O-[4-[4-[4-O-[4-(2,3,4,5,6-penta-O-sulfo-D-glucit-1-ylcarbamoyl)-phenyl]-2,3-di-O-sulfo-L-threit-1-yloxy]-benzyl]-phenyl]-2,3,4,5-tetra-O-sulfo-galactitol octadecasodium salt, [a]0.0° (c 0.6; water), MS: m/z 3158.0 (reconstructed M).

EXAMPLE 52

A. 0.50 g of 1,6-bis-O-[4-[4-O-[4-[(E)-2-carboxy-vinyl]-phenyl]-2,3-O-isopropylidene-D-threit-1-yloxy]-phenyl]-2,3:4,5-di-O-isopropylidene-galactitol (Example 48.F.) dissolved in 5 ml of dimethylformamide was treated with 0.11 ml of 4-methyl-morpholine at 0°–5° C. with the exclusion of moisture and stirred intensively for 10 minutes. Thereupon, 0.18 g of solid 2-chloro-4,6-dimethoxy-1,3,5-triazine was added and the mixture was stirred at 0°–5° C. for a further 2 hours. Subsequently, 0.21 g of N-methyl-D-glucamine was added and the mixture was stirred at room temperature for a further 18 hours. Thereupon, the reaction mixture was diluted with water and concentrated, the residue was treated with water and the mixture was boiled briefly and filtered. There was thus obtained 1,6-bis-O-[4-[4-O-[4-[(E)-2-(D-glucit-1-yl-methyl-carbamoyl)-vinyl]-phenyl]-2,3-O-isopropylidene-D-threit-1-yloxy]-phenyl]-2,3:4,5-di-O-isopropylidene-galactitol as a colorless solid, MS: m/z 1403.7 ([M+Na]+).

B. 0.64 g of 1,6-bis-O-[4-[4-O-[4-[(E)-2-(D-glucit-1-yl-methyl-carbamoyl)-vinyl]-phenyl]-2,3-O-isopropylidene-D-threit-1-yloxy]-phenyl]-2,3:4,5-di-O-isopropylidene-galactitol was suspended in 4 ml of dioxan, 1 ml of trifluoroacetic acid and 1 ml of water and heated under reflux at 110° C. for 18 hours. Subsequently, the reaction mixture was concentrated to dryness, treated with 10 ml of water and 0.2 ml of triethylamine and filtered; the thus-obtained residue was dissolved in 10 ml of acetic anhydride and 10 ml of pyridine and stirred at room temperature for 18 hrs. The reaction mixture was subsequently diluted with water, the aqueous phase was extracted with methylene chloride and the combined methylene chloride phases were dried over magnesium sulfate and concentrated. The thus-obtained crude product was chromatographed on silica gel with 5% isopropanol in methylene chloride. There was thus obtained 2,3,4,5-tetra-O-acetyl-1,6-bis-O-[4-[2,3-di-O-acetyl-4-O-[4-[(E)-2-[(2,3,4,5,6-penta-O-acetyl-D-glucit-1-yl)-methyl-carbamoyl]-vinyl]-phenyl]-D-threit-1-yloxy]-phenyl]-galactitol as a colorless solid, MS: m/z 1978.6 ([M+H]+).

C. 0.34 g of 2,3,4,5-tetra-O-acetyl-1,6-bis-O-[4-[2,3-di-O-acetyl-4-O-[4-[(E)-2-[(2,3,4,5,6-penta-O-acetyl-D-glucit-1-yl)-methyl-carbamoyl]-vinyl]-phenyl]-D-threit-1-yloxy]-phenyl]-galactitol was dissolved in 4 ml of methanol and 4 ml of tetrahydrofuran, treated with 0.3 ml of 1 molar sodium methylate solution in methanol and stirred at room temperature for 18 hours. The thus-formed precipitate was filtered off and washed with methanol. There was thus obtained 1,6-bis-O-[4-[4-O-[4-[(E)-2-(D-glucit-1-yl-methyl-carbamoyl)-vinyl]-phenyl]-D-threit-1-yloxy]-phenyl]-galactitol as a colorless solid, MS: m/z 1244.0 ([M+Na]+).

D. The 1,6-bis-O-[4-[4-O-[4-[(E)-2-(D-glucit-1-yl-methyl-carbamoyl)-vinyl]-phenyl]-D-threit-1-yloxy]-phenyl]-galactitol obtained above was converted analogously to Example 1.B. into 1,6-bis-O-[4-[4-O-[4-[(E)-2-[methyl-(2,3,4,5,6-penta-O-sulfo-D-glucit-1-yl)-carbamoyl]-vinyl]-phenyl]-2,3-di-O-sulfo-D-threit-1-yloxy]-phenyl]-2,3,4,5-tetra-O-sulfo-galactitol octadecasodium salt, [a]+2.4° (c 0.8; water).

EXAMPLE 53

A. 0.23 g of 1,6-bis-O-[4-[4-O-[4-[(E)-2-[methyl-(2,3,4,5,6-penta-O-sulfo-D-glucit-1-yl)-carbamoyl]-vinyl]- phenyl]-2,3-di-O-sulfo-D-threit-1-yloxy]-phenyl]-2,3,4,5-tetra-O-sulfo-galactitol octadecasodium salt (Example 52.D.) was exhaustively hydrogenated in 5 ml of distilled water in a hydrogen atmosphere with the addition of 50 mg of palladium on charcoal (10%). Subsequently, the reaction mixture was filtered over a 0.8µ cellulose filter and the filtrate was lyophilized; there was thus obtained 1,6-bis-O-[4-[4-O-[4-[2-[methyl-(2,3,4,5,6-penta-O-sulfo-D-glucit-1-yl)-carbamoyl]-ethyl]-phenyl]-2,3-di-O-sulfo-D-threit-1-yloxy]-phenyl]-2,3,4,5-tetra-O-sulfo-galactitol octadecasodium salt, [a]–2.5° (c 0.6; water), MS: m/z 3060.5 (reconstructed M).

EXAMPLE 54

A. 1.42 g of 2,3:4,5-di-O-isopropylidene-1,6-bis-O-(4-methyl-phenylsulfonyl)-galactitol, 1.25 g 3-benzyloxy-naphthalen-2-ol (E. Weber et al., Chem. Ber. 122, 959 (1989)) and 1.40 g of finely ground anhydrous potassium carbonate were suspended in 20 ml of dimethylformamide and stirred at 100° C. under argon for 16 hours. Subsequently, the reaction mixture was diluted with ice-water and the precipitate formed was filtered off and dissolved in methylene chloride. The methylene chloride phase was dried over magnesium sulfate and concentrated. There was obtained 1,6-bis-O-(3-benzyloxy-naphthalen-2-yl)-2,3:4,5-di-O-isopropylidene-galactitol in the form of colorless crystals, MS: m/z 726 ([M]$^+$).

B. 1.4 g of 1,6-bis-O-(3-benzyloxy-naphthalen-2-yl)-2,3:4,5-di-O-isopropylidene-galactitol were exhaustively hydrogenated in 50 ml of ethyl acetate in a hydrogen atmosphere with the addition of 0.25 g of palladium on charcoal (10%). The reaction mixture was subsequently filtered over a 0.8µ cellulose filter, the filtrate was concentrated and the residue was recrystallized from ether/hexane; there was thus obtained 1,6-bis-O-(3-hydroxy-naphthalen-2-yl)-2,3:4,5-di-O-isopropylidene-galactitol as a colorless solid, MS: m/z 546 ([M]$^+$).

C. 3.76 g of 2,3-O-isopropylidene-1,4-bis-O-(4-methyl-phenylsulfonyl)-L-threitol, 1.60 g of methyl 3-hydroxy-naphthalene-2-carboxylate and 1.3 g of finely ground anhydrous potassium carbonate were suspended in 50 ml of acetonitrile and stirred under reflux and under argon for 60 hours. The reaction mixture was subsequently diluted with water and extracted with methylene chloride. The combined methylene chloride phases were dried over magnesium sulfate, concentrated and the residue was chromatographed on silica gel with 5% ether in methylene chloride. There was thus obtained 2,3-O-isopropylidene-1-O-(3-methoxycarbonyl-naphthalen-2-yl)-4-O-(4-methyl-phenylsulfonyl)-L-threitol as a colorless oil, MS: m/z 500 ([M]$^+$).

D. 1.3 g of 2,3-O-isopropylidene-1-O-(3-methoxycarbonyl-naphthalen-2-yl)-4-O-(4-methyl-phenylsulfonyl)-L-threitol, 0.62 g of 1,6-bis-O-(3-hydroxy-naphthalen-2-yl)-2,3:4,5-di-O-isopropylidene-galactitol and 0.48 g of finely ground anhydrous potassium carbonate were suspended in 20 ml of dimethyl-formamide and stirred at 100° C. under argon for 8 hours. Subsequently, the reaction mixture was diluted with water and extracted with methylene chloride. The combined methylene chloride phases were dried over magnesium sulfate and concentrated, and the residue was chromatographed on silica gel with 5% ether in methylene chloride. There was thus obtained 2,3:4,5-di-O-isopropylidene-1,6-bis-O-[3-[2,3-O-isopropylidene-4-O-(3-methoxycarbonyl-naphthalen-2-yl)-L-threit-1-yloxy]-naphthalen-2-yl]-galactitol as a colorless solid, MS: m/z 1220.5 ([M+NH$_4$]$^+$).

E. 0.9 g of 2,3:4,5-di-O-isopropylidene-1,6-bis-O-[3-[2,3-O-isopropylidene-4-O-(3-methoxycarbonyl-naphthalen-2-yl)-L-threit-1-yloxy]-naphthalen-2-yl]-galactitol was dissolved in 10 ml of 2-methoxyethanol, treated with 1.5 ml of concentrated sodium hydroxide solution and 2 ml of water and heated under reflux for 16 hrs. Thereupon, the mixture was acidified with 1N acid while acid while cooling with ice and the precipitate formed was filtered off. There was thus obtained 1,6-bis-O-[3-[4-O-(3-carboxy-naphthalen-2-yl)-2,3-O-isopropylidene-L-threit-1-yloxy]-naphthalen-2-yl]-2,3:4,5-di-O-isopropylidene-galactitol as a colorless solid, MS: m/z 1173.2 ([M–H]$^-$).

F. 0.9 g of 1,6-bis-O-[3-[4-O-(3-carboxy-naphthalen-2-yl)-2,3-O-isopropylidene-L-threit-1-yloxy]-naphthalen-2-yl]-2,3:4,5-di-O-isopropylidene-galactitol was suspended in 16 ml of dioxan, 2 ml of trifluoroacetic acid and 2 ml of water and heated under reflux at 110° C. for 18 hours. The reaction mixture was subsequently concentrated to dryness and the residue was suspended in water and filtered off; there was thus obtained 1,6-bis-O-[3-[4-O-(3-carboxy-naphthalen-2-yl)-L-threit-1-yloxy]-naphthalen-2-yl]-galactitol as a colorless solid, MS: m/z 1013.0 ([M–H]$^-$).

G. 0.75 g of 1,6-bis-O-[3-[4-O-(3-carboxy-naphthalen-2-yl)-L-threit-1-yloxy]-naphthalen-2-yl]-galactitol was dissolved in 10 ml of acetic anhydride and 10 ml of pyridine and stirred at room temperature for 24 hrs. The reaction mixture was subsequently diluted with water and the precipitate formed was filtered off. This was thereupon suspended in 20 ml of dioxan, treated with 10 ml of pyridine and 5 ml of water and stirred at room temperature for 3 hours. Now, the reaction mixture was again concentrated, the residue was treated with ice-cold 1N hydrochloric acid and the thus-formed precipitate was filtered off. There was obtained 2,3,4,5-tetra-O-acetyl-1,6-bis-O-[3-[2,3-di-O-acetyl-4-O-(3-carboxy-naphthalen-2-yl)-L-threit-1-yloxy]-naphthalen-2-yl]-galactitol as a colorless solid, MS: m/z 1349.2 ([M–H]$^-$).

H. 0.96 g of 2,3,4,5-tetra-O-acetyl-1,6-bis-O-[3-[2,3-di-O-acetyl-4-O-(3-carboxy-naphthalen-2-yl)-L-threit-1-yloxy]-naphthalen-2-yl]-galactitol dissolved in 7 ml of dimethylformamide was treated with 0.19 ml of 4-methylmorpholine at 0°–5° C. with the exclusion of moisture and stirred intensively for 10 minutes. Thereupon, 0.29 g of solid 2-chloro-4,6-dimethoxy-1,3,5-triazine was added and the mixture was stirred at 0°–5° C. for a further 2 hours. Subsequently, 0.31 g of D-glucamine was added and the mixture was stirred at room temperature for a further 18 hours. Thereupon, the reaction mixture was diluted with water and concentrated, the residue was treated with water and the mixture was boiled briefly and filtered. There was thus obtained 2,3,4,5-tetra-O-acetyl-1,6-bis-O-[3-[2,3-di-O-acetyl-4-O-(3-D-glucit-1-ylcarbamoyl-naphthalen-2-yl)-L-threit-1-yloxy]-naphthalen-2-yl]-galactitol as a colorless solid, MS: m/z 1678 ([M+H]$^+$).

I. 0.50 g of 2,3,4,5-tetra-O-acetyl-1,6-bis-O-[3-[2,3-di-O-acetyl-O-(3-D-glucit-1-ylcarbamoyl-naphthalen-2-yl)-L-threit-1-yloxy]-naphthalen-2-yl]-galactitol was dissolved in 8 ml of methanol and 8 ml of tetrahydrofuran, treated with 0.6 ml of 1 molar sodium methylate solution in methanol and the reaction mixture was stirred at room temperature for 18 hours. The precipitate which thereby formed was filtered off and washed with methanol. There was thus obtained 1,6-bis-O-[3-[4-O-(3-D-glucit-1-ylcarbamoyl-naphthalen-2-yl)-L-threit-1-yloxy]-naphthalen-2-yl]-galactitol as a colorless solid, MS: m/z 1341.2 ([M+H]$^+$).

K. The 1,6-bis-O-[3-[4-O-(3-D-glucit-1-ylcarbamoyl-naphthalen-2-yl)-L-threit-1-yloxy]-naphthalen-2-yl]-galactitol obtained above was converted analogously to Example 1.B. into 1,6-bis-O-[3-[4-O-[3-(2,3,4,5,6-penta-O-sulfo-D-glucit-1-ylcarbamoyl)-naphthalen-2-yl]-2,3-di-O-sulfo-L-threit-1-yloxy]-naphthalen-2-yl]-2,3,4,5-tetra-O-sulfo-galactitol octadecasodium salt, [a]+6.1° (c 0.9; water).

EXAMPLE 55

A. 9.5 g of 2,3-O-isopropylidene-1,4-bis-O-(4-methyl-phenyl-sulfonyl)-L-threitol and 5.86 g of 4-(4-benzyloxy-benzyl)-phenol (Example 51.A.) were reacted at 100° C. for 6 hours in 300 ml of dimethylformamide with the addition of 27.9 g of potassium carbonate. The reaction mixture was subsequently worked up extractively with ice-water and methylene chloride. The crude product was chromatographed on silica gel with n-hexane/ethyl acetate. There was thus obtained 1-O-[4-(4-benzyloxy-benzyl)-phenyl]-2,3-O-isopropylidene-4-O-(4-methyl-phenylsulfonyl)-L-threitol as a colorless oil, MS: m/z 588.0 ([M]$^+$).

B. 3.0 g of 1-O-[4-(4-benzyloxy-benzyl)-phenyl]-2,3-O-isopropylidene-4-O-(4-methyl-phenylsulfonyl)-L-threitol, 1.0 g of 1,6-bis-O-(4-hydroxy-phenyl)-2,3:4,5-di-O-isopropylidene-galactitol (Example 48.B.) and 0.93 g of finely ground anhydrous potassium carbonate were suspended in 30 ml of dimethylformamide and stirred at 100° C. under argon for 48 hours. The reaction mixture was subsequently diluted with water and extracted with ether. The combined ether phases were dried over magnesium sulfate, concentrated and the residue was chromatographed on silica gel with 5% ether in methylene chloride. There was thus obtained 1,6-bis-O-[4-[4-O-[4-(4-benzyloxy-benzyl)-phenyl]-2,3-O-isopropylidene-L-threit-1-yloxy]-phenyl]-2,3:4,5-di-O-isopropylidene-galactitol as a yellowish oil, MS: m/z 1296.4 ([M+NH$_4$]$^+$).

C. 0.5 g of 1,6-bis-O-[4-[4-O-[4-(4-benzyloxy-benzyl)-phenyl]-2,3-O-isopropylidene-L-threit-1-yloxy]-phenyl]-2,3:4,5-di-O-isopropylidene-galactitol was exhaustively hydrogenated in 10 ml of tetrahydrofuran in a hydrogen atmosphere with the addition of 0.1 g of palladium on charcoal (10%). Subsequently, the reaction mixture was filtered over a 0.8μ cellulose filter and the filtrate was concentrated: there was thus obtained 1,6-bis-O-[4-[4-O-[4-(4-hydroxy-benzyl)-phenyl]-2,3-O-isopropylidene-L-threit-1-yloxy]-phenyl]-2,3:4,5-di-O-isopropylidene-galactitol as a colorless solid, MS: m/z 1097.2 ([M–H]$^-$).

D. 1.0 g of 1,6-bis-O-[4-[4-O-[4-(4-hydroxy-benzyl)-phenyl]-2,3-O-isopropylidene-L-threit-1-yloxy]-phenyl]-2,3:4,5-di-O-isopropylidene-galactitol, 0.9 g of 2,3-O-isopropylidene-1-O-(4-methoxycarbonyl-phenyl)-4-O-(4-methyl-phenylsulfonyl)-L-threitol (Example 51.B.) and 1.0 g of finely ground anhydrous potassium carbonate were suspended in 3 ml of dimethylformamide and stirred at 100° C. under argon for 18 hours. The reaction mixture was subsequently diluted with water and extracted with ether. The combined ether phases were dried over magnesium sulfate and concentrated. The residue was chromatographed on silica gel with 2%-5% ether in methylene chloride. There was thus obtained 2,3:4,5-di-O-isopropylidene-1,6-bis-O-[4-[2,3-O-isopropylidene-4-O-[4-[2,3-O-isopropylidene-4-O-(4-methoxycarbonyl-phenyl)-L-threit-1-yloxy]-benzyl]-phenyl]-L-threit-1-yloxy]-phenyl]-galactitol as a colorless solid, MS: m/z 1673.8 ([M+NH$_4$]$^+$).

E. 0.428 g of 2,3:4,5-di-O-isopropylidene-1,6-bis-O-[4-[2,3-O-isopropylidene-4-O-[4-[4-[2,3-O-isopropylidene-4-O-(4-methoxycarbonyl-phenyl)-L-threit-1-yloxy]-benzyl]-phenyl]-L-threit-1-yloxy]-phenyl]-galactitol was dissolved in 5 ml of 2-methoxyethanol, treated with 1 ml of concentrated sodium hydroxide solution and 0.5 ml of water and heated under reflux for 3 hrs. Thereupon, the mixture was acidified with 1N hydrochloric acid while cooling with ice and the precipitate which formed was filtered off. There was thus obtained 1,6-bis-O-[4-[4-O-[4-[4-[4-O-(4-carboxy-phenyl-2,3-O-isopropylidene-L-threit-1-yloxy]-benzyl]-phenyl]-2,3-O-isopropylidene-L-threit-1-yloxy]-phenyl]-2,3:4,5-di-O-isopropylidene-galactitol as a colorless solid, MS: m/z 1626.5 ([M–H]$^-$).

F. 0.345 g of 1,6-bis-O-[4-[4-O-[4-[4-[4-O-(4-carboxy-phenyl)-2,3-O-isopropylidene-L-threit-1-yloxy]-benzyl]-phenyl]-2,3-O-isopropylidene-L-threit-1-yloxy]-phenyl]-2,3:4,5-di-O-isopropylidene-galactitol dissolved in 2 ml of dimethylformamide was treated with 0.1 ml of 4-methylmorpholine at 0°–5° C. with the exclusion of moisture and stirred intensively for 10 minutes.

Thereupon, 0.08 g of solid 2-chloro-4,6-dimethoxy-1,3,5-triazine was added and the mixture was stirred at 0°–5° C. for a further 2 hours. Subsequently, 0.085 g of D-glucamine was added and the mixture was stirred at room temperature for a further 18 hours. Thereupon, the reaction mixture was diluted with water and concentrated, the residue was treated with water and the mixture was boiled briefly and filtered. There was thus obtained 1,6-bis-O-[4-[4-O-[4-[4-[4-O-(4-D-glucit-1-ylcarbamoyl-phenyl)-2,3-O-isopropylidene-L-threit-1-yloxy]-benzyl]-phenyl]-2,3-O-isopropylidene-L-threit-1-yloxy]-phenyl]-2,3:4,5-di-O-isopropylidene-galactitol as a colorless solid, MS: m/z 1953.4 ([M+H]$^+$).

G. 0.38 g of 1,6-bis-O-[4-[4-O-[4-[4-[4-O-(4-D-glucit-1-ylcarbamoyl-phenyl)-2,3-O-isopropylidene-L-threit-1-yloxy]-benzyl]-phenyl]-2,3-O-isopropylidene-L-threit-1-yloxy]-phenyl]-2,3:4,5-di-O-isopropylidene-galactitol was suspended in 9 ml of dioxan, 1.6 ml of trifluoroacetic acid and 3 ml of water and heated at 110° C. under reflux for 18 hours. Subsequently, the reaction mixture was concentrated to dryness, the residue was suspended in water and the suspension was filtered; there was thus obtained 1,6-bis-O-[4-[4-O-[4-[4-[4-O-(4-D-glucit-1-ylcarbamoyl-phenyl)-L-threit-1-yloxy]-benzyl]-phenyl]-L-threit-1-yloxy]-phenyl]-galactitol as a colorless solid, MS: m/z 1737.8 ([M+Na]$^+$).

H. The 1,6-bis-O-[4-[4-O-[4-[4-[4-O-(4-D-glucit-1-ylcarbamoyl-phenyl)-L-threit-1-yloxy]-benzyl]-phenyl]-L-threit-1-yloxy]-phenyl]-galactitol obtained above was converted analogously to Example 1.B. into 1,6-bis-O-[4-[4-O-[4-[4-[4-O-[4-(2,3,4,5 sulfo-D-glucit-1-ylcarbamoyl)-phenyl]-2,3-di-O-sulfo-L-threit-1-yloxy]-benzyl]-phenyl]-2,3-di-O-sulfo-L-threit-1-yloxy]-phenyl]-2,3,4,5-tetra-O-sulfo-galactitol docosodium salt, [a]+4.7° (c 0.6; water), MS: m/z 3959.0 (reconstructed M).

EXAMPLE 56

A. 1.2 g of 1,6-bis-O-(3-carboxy-naphthalen-1-yl)-2,3:4,5-di-O-isopropylidene-galactitol (Example 19.A.) were suspended in 15 ml of dioxan, 5 ml of trifluoroacetic acid and 5 ml of water and heated under reflux at 110° C. for 17 hours. Thereupon, the reaction mixture was concentrated the residue was treated with water and the mixture was filtered. There was thus obtained 1,6-bis-O-(3-carboxy-naphthalen-1-yl)-galactitol as a colorless solid, MS: m/z 521.2 ([M–H]$^-$).

B. 0.96 g of 1,6-bis-O-(3-carboxy-naphthalen-1-yl)-galactitol 2,3,4,5-tetra-O-acetyl-1,6-bis-O-(3-carboxy-naphthalen-1-yl)-galactitol was stirred at room temperature in a mixture of 6 ml of acetic anhydride and 11 ml of pyridine for 18 hours. Thereupon, the reaction mixture was concentrated, the residue was treated with ice-water and dilute hydrochloric acid and the thus-formed precipitate was filtered off. There was thus obtained 2,3,4,5-tetra-O-acetyl-1,6-bis-O-(3-carboxy-naphthalen-1-yl)-galactitol as a colorless solid, MS: m/z 689.2 ([M–H]⁻).

C. A solution of 30 g of benzyl 2-benzyloxycarbonylamino-2-desoxy-a-D-glucopyranoside (Heyns and Paulsen, Chem. Ber. 88, 188 (1955)) in 116 ml of pyridine was treated at 0° C. with a solution of 19.85 g of p-tolylsulfonyl chloride in 30 ml of dichloromethane and stirred at room temperature for 4 hours. Then, the mixture was poured into ice-cold 2N sulfuric acid and extracted with dichloromethane. The organic phases were washed with aqueous sodium hydrogen carbonate solution, dried over magnesium sulfate and concentrated. The residue was chromatographed over silica gel with hexane/ethyl acetate and gave benzyl 2-benzyloxycarbonylamino-2-desoxy-6-O-(p-tolylsulfonyl)-a-D-glucopyranoside, [a]+101.8° (c 0.5; dioxan), MS: m/z 580 ([M+Na]⁺).

D. A solution of 32.14 g benzyl 2-benzyloxycarbonylamino-2-desoxy-6-O-(p-tolylsulfonyl)-a-D-glucopyranoside in 75 ml of dimethyl sulfoxide was treated at room temperature with 7.5 g of sodium azide and stirred at 90° C. for 3 hours. The mixture was then poured on to ice/water. Separated crystals were filtered off under suction, washed with water and dried. There was obtained benzyl 6-azido-2-benzyloxycarbonylamino-2,6-didesoxy-a-D-glucopyranoside, [a]+119.60° (c 0.5; dioxan), MS: m/z 428 ([M+H]⁺).

E. A solution of 1.1 g of benzyl 6-azido-2-benzyloxycarbonyl-amino-2,6-didesoxy-a-D-glucopyranoside in 7.5 ml of tetra-hydrofuran and 69 µl water was treated with 674 mg of triphenylphosphine at room temperature and stirred for 24 hours. Then, 1 ml of water was added to the thick slurry and the mixture was stirred for a further 30 minutes and concentrated. The residue was crystallized from methanol and gave benzyl 6-amino-2-benzyloxycarbonylamino-2,6-didesoxy-a-D-glucopyranoside, [a]+124.2° (c 0.6; acetone), MS: m/z 403 ([M+H]⁺).

F. A suspension of 3.0 g of benzyl 6-amino-2-benzyloxycarbonylamino-2,6-didesoxy-a-D-glucopyranoside and 1.33 g of D-gluconic acid g-lactone in 60 ml of dioxan was brought into solution at 80° C. and held at this temperature for a further 18 hours. The separated product was filtered off under suction, washed with dioxan and dried to give D-gluconic acid (benzyl 2-benzyloxycarbonylamino-2,6-didesoxy-a-D-glucopyranosid-6-yl)-amide, [a]+120.0° (c 0.2; dioxan), MS: m/z 603.2 ([M+Na]⁺).

G. A solution of 1.4 g of D-gluconic acid (benzyl 2-benzyloxy-carbonylamino-2,6-didesoxy-a-D-glucopyranosid-6-yl)-amide in 5 ml of pyridine was acetylated with 2 ml of acetic acid for 18 hours and concentrated to give 2,3,4,5,6-penta-O-acetyl-D-gluconic acid (benzyl 3,4-di-O-acetyl-2-benzyloxycarbonylamino-2,6-didesoxy-a-D-glucopyranosid-6-yl)-amide, [a]+84.0° (c 0.2; dioxan), MS: m/z 897.3 ([M+Na]⁺).

H. A solution of 250 mg of 2,3,4,5,6-penta-O-acetyl-D-gluconic acid (benzyl 3,4-di-O-acetyl-2-benzyloxycarbonylamino-2,6-didesoxy-a-D-glucopyranosid-6-yl)-amide in 20 ml of dioxan and 2 ml water was hydrogenated at room temperature in the presence of palladium on charcoal (10%). After 2 hours, the catalyst was filtered off over a filter aid and the filtrate was concentrated. The residue was crystallized from ethyl acetate/ether and gave 2,3,4,5,6-penta-O-acetyl-D-gluconic acid (benzyl 3,4-di-O-acetyl-2-amino-2,6-didesoxy-a-D-glucopyranosid-6-yl)-amide, [a]+96.0° (c 0.2; dioxan), MS: m/z 741.1 ([M+H]⁺).

I. A solution of 0.60 g of 2,3,4,5-tetra-O-acetyl-1,6-bis-O-(3-carboxy-naphthalen-1-yl)-galactitol in 8 ml of dimethylformamide was treated with 0.21 ml of 4-methylmorpholine at 0°–5° C. with the exclusion of moisture and stirred intensively for 10 minutes. Thereupon, 0.31 g of solid 2-chloro-4,6-dimethoxy-1,3,5-triazine was added and the mixture was stirred at 0°–5° C. for a further 2 hours. Subsequently, 1.27 g of 2,3,4,5,6-penta-O-acetyl-D-gluconic acid (benzyl 3,4-di-O-acetyl-2-amino-2,6-didesoxy-a-D-gluco-pyranosid-6-yl)-amide were added and the mixture was stirred at room temperature for a further 18 hours. Thereupon, the reaction mixture was diluted several times with water, evaporated at 40°–50° C. under reduced pressure and the residue was partitioned between water/methanol and methylene chloride. The combined methylene chloride phases were dried over magnesium sulfate, filtered and concentrated, and the thus-obtained residue was chromatographed on silica gel with methylene chloride/methanol; there was thus obtained 1,6-bis-O-[3-[benzyl 2,6-didesoxy-6-(2,3,4,5,6-penta-O-acetyl-D-gluconoylamino)-3,4-di-O-acetyl-a-D-glucopyranosid-2-ylcarbamoyl]-naphthalen-1-yl]-2,3,4,5-tetra-O-acetyl-galactitol as a colorless solid, MS: m/z 2157.4 ([M+Na]⁺).

K. 0.71 g of 1,6-bis-O-[3-[benzyl 2,6-didesoxy-6-(2,3,4,5,6-penta-O-acetyl-D-gluconoylamino)-3,4-di-O-acetyl-a-D-glucopyranosid-2-ylcarbamoyl]-naphthalen-1-yl]-2,3,4,5-tetra-O-acetyl-galactitol was dissolved in 8 ml of methanol and 8 ml of tetrahydrofuran, treated with 0.3 ml of 1 molar sodium methylate solution in methanol and stirred at room temperature for 18 hours. The precipitate which thereby formed was filtered off. There was thus obtained 1,6-bis-O-[3-(benzyl 2,6-didesoxy-6-D-gluconoylamino-a-D-glucopyranosid-2-ylcarbamoyl)-naphthalen-1-yl]-galactitol as a colorless solid, MS: m/z 1401.7 ([M+Na]⁺).

L. The 1,6-bis-O-[3-(benzyl 2,6-didesoxy-6-D-gluconoylamino-a-D-glucopyranosid-2-ylcarbamoyl)-naphthalen-1-yl]-galactitol obtained above was converted analogously to Example 1.B. into 1,6-bis-O-[3-[benzyl 2,6-didesoxy-6-(2,3,4,5,6-penta-O-sulfo-D-gluconoylamino)-3,4-di-O-sulfo-a-D-glucopyranosid-2-ylcarbamoyl]-naphthalen-1-yl]-2,3,4,5-tetra-O-sulfo-galactitol octadecasodium salt, [a]+60.9° (c 0.7; water), MS: m/z 3216.5 (reconstructed M).

EXAMPLE 57

A. 5.3 g of 2,3:4,5-di-O-isopropylidene-1,6-bis-O-[(E)-4-(2-methoxycarbonyl-vinyl)-phenyl]-galactitol (Example 3.A.) were suspended in 120 ml of dioxan, 15 ml of trifluoroacetic acid and 30 ml of water and heated under reflux at 110° C. for 4 hours. Thereupon, the reaction mixture was concentrated, the residue was treated with water and the mixture was filtered. There was thus obtained 1,6-bis-O-[4-[(E)-2-methoxycarbonyl-vinyl]-phenyl]-galactitol as a colorless solid, MS: m/z 502 ([M]⁺).

B. 4.5 g of 1,6-bis-O-[4-[(E)-2-methoxycarbonyl-vinyl]-phenyl]-galactitol, 50 ml of methanol and 40 ml of concentrated aqueous sodium hydroxide solution were heated under reflux at 110° C. for 24 hours. Thereupon, the majority of the methanol was distilled off under reduced pressure, the residue was diluted with ice-water, acidified with dilute aqueous hydrochloric acid and the crystals which thereby formed were filtered off. There was thus obtained 1,6-bis-O-[4-[(E)-2-carboxy-vinyl]-phenyl]-galactitol in the form of colorless crystals, MS: m/z 473.4 ([M−H]⁻).

C. 4.23 g of 1,6-bis-O-[4-[(E)-2-carboxy-vinyl]-phenyl]-galactitol were stirred at room temperature in a mixture of 25 ml of acetic anhydride and 50 ml of pyridine for 18 hours. Thereupon, the reaction mixture was concentrated and the residue was treated with ice-water and dilute hydrochloric acid. The thus-formed precipitate was filtered off, dissolved in 95 ml of dioxan, treated with 50 ml of pyridine and 15 ml of water and stirred at room temperature for a further 3 hours; thereupon the mixture was concentrated, the residue was treated with ice-water and dilute hydrochloric acid and the thus-formed precipitate was filtered off. There was thus obtained 2,3,4,5-tetra-O-acetyl-1,6-bis-O-[4-[(E)-2-carboxy-vinyl]-phenyl]-galactitol as a colorless solid, MS: m/z 641.2 ([M−H]⁻).

D. 0.55 g of 2,3,4,5-tetra-O-acetyl-1,6-bis-O-[4-[(E)-2-carboxy-vinyl]-phenyl]-galactitol in 8 ml of dimethylformamide was treated with 0.21 ml of 4-methylmorpholine at 0°–5° C. with the exclusion of moisture and stirred intensively for 10 minutes. Thereupon, 0.31 g of solid 2-chloro-4,6-dimethoxy-1,3,5-triazine was added and the mixture was stirred at 0°–5° C. for a further 2 hours. Subsequently, 1.27 g of 2,3,4,5,6-penta-O-acetyl-D-gluconic acid (benzyl 3,4-di-O-acetyl-2-amino-2,6-didesoxy-a-D-glucopyranosid-6-yl)-amide (Example 56.H.) were added and the mixture was stirred at room temperature for a further 18 hours. Thereupon, the reaction mixture was diluted several times with water, evaporated at 40°–50° C. under reduced pressure and the residue was partitioned between water/methanol and methylene chloride. The combined methylene chloride phases were dried over magnesium sulfate, filtered and concentrated, and the thus-obtained residue was chromatographed on silica gel with methylene chloride/methanol; there was thus obtained 2,3,4,5-tetra-O-acetyl-1,6-bis-O-[4-[(E)-2-[benzyl 3,4-di-O-acetyl-2,6-didesoxy-6-(2,3,4,5,6-penta-O-acetyl-D-gluconoylamino)-a-D-glucopyranosid-2-ylcarbamoyl]-vinyl]-phenyl]-galactitol as a colorless solid, MS: m/z 2088.4 ([M+H]⁺).

E. 0.44 g of 2,3,4,5-tetra-O-acetyl-1,6-bis-O-[4-[(E)-2-[benzyl-3,4-di-O-acetyl-2,6-didesoxy-6-(2,3,4,5,6-penta-O-acetyl-D-gluconoylamino)-a-D-glucopyranosid-2-ylcarbamoyl]-vinyl]-phenyl]-galactitol was dissolved in 5 ml of methanol and 5 ml of tetrahydrofuran, treated with 0.2 ml of 1 molar sodium methylate solution in methanol and stirred at room temperature for 18 hours. The precipitate which thereby formed was filtered off. There was thus obtained 1,6-bis-O-[4-[(E)-2-(benzyl 2,6-didesoxy-6-D-gluconoylamino-a-D-glucopyranoside-2-ylcarbamoyl)-vinyl]-phenyl]-galactitol as a colorless solid, MS: m/z 1354.5 ([M+Na]⁺).

F. The 1,6-bis-O-[4-[(E)-2-(benzyl-2,6-didesoxy-6-D-gluconoylamino-a-D-glucopyranosid-2-ylcarbamoyl)-vinyl]-phenyl]-galactitol obtained above was converted analogously to Example 1.B. into 1,6-bis-O-[4-[(E)-2-[benzyl 2,6-didesoxy-6-(2,3,4,5,6-penta-O-sulfo-D-gluconoylamino)-3,4-di-O-sulfo-a-D-glucopyranosid-2-ylcarbamoyl]-vinyl]-phenyl]-2,3,4,5-tetra-O-sulfo-galactitol octadecasodium salt, [a]+45.6° (c 0.7; water), MS: m/z 316.75 (reconstructed M).

EXAMPLE 58

A. 0.88 g of 2,3,4,5-tetra-O-acetyl-1,6-bis-O-[4-[(E)-2-[benzyl-3,4-di-O-acetyl-2,6-didesoxy-6-(2,3,4,5,6-penta-O-acetyl-D-gluconoylamino)-a-D-glucopyranosid-2-ylcarbamoyl]-vinyl]-phenyl]-galactitol (Example 57.D.) was exhaustively hydrogenated in 20 ml of tetrahydrofuran in a hydrogen atmosphere with the addition of 350 mg of palladium on charcoal (10%). Subsequently, the reaction mixture was filtered over a 0.8µ cellulose filter and concentrated. The thus-obtained residue was chromatographed on silica gel with methylene chloride/ methanol; there was thus obtained 2,3,4,5-tetra-O-acetyl-1,6-bis-O-[4-[2-[benzyl 3,4-di-O-acetyl-2,6-didesoxy-6-(2,3,4,5,6-penta-O-acetyl-gluconoylamino)-a-D-glucopyranosid-2-ylcarbamoyl]-ethyl]-phenyl]-galactitol as a colorless oil, MS: m/z 2114.5 ([M+Na]⁺).

B. 0.24 g of 2,3,4,5-tetra-O-acetyl-1,6-bis-O-[4-[2-[benzyl 3,4-di-O-acetyl-2,6-didesoxy-6-(2,3,4,5,6-penta-O-acetyl-gluconoylamino)-a-D-glucopyranosid-2-ylcarbamoyl]-ethyl]-phenyl]-galactitol was dissolved in 2 ml of methanol and 2 ml of tetrahydrofuran, treated with 0.15 ml of 1 molar sodium methylate solution in methanol and stirred at room temperature for 18 hours. The precipitate which thereby formed was filtered off. There was thus obtained 1,6-bis-O-[4-[2-(benzyl 2,6-didesoxy-6-gluconoylamino-a-D-glucopyranosid-2-ylcarbamoyl)-ethyl]-phenyl]-galactitol as a colorless solid, MS: m/z 1357.4 ([M+Na]⁺).

C. The 1,6-bis-O-[4-[2-(benzyl 2,6-didesoxy-6-gluconoylamino-a-D-glucopyranosid-2-ylcarbamoyl)-ethyl]-phenyl]-galactitol obtained above was converted analogously to Example 1.B. into 1,6-bis-O-[4-[2-[benzyl-2,6-didesoxy-6-(2,3,4,5,6-penta-O-sulfo-D-gluconoylamino)-3,4-di-O-sulfo-a-D-glucopyranosid-2-ylcarbamoyl]-ethyl]-phenyl]-2,3,4,5-tetra-O-sulfo-galactitol octadecasodium salt, [a]+48.8° (c 0.5; water), MS: m/z 3172.5 (reconstructed M).

EXAMPLE 59

A. A solution of 7.4 g of 4-fluoro-3-nitro-benzoic acid in 100 ml of dimethylformamide was treated with 16.0 g of D-glucamine and stirred at room temperature for 4 hours. After the addition of 6 ml of triethylamine, the mixture was stirred at 40° C. for a further 16 hours. The reaction solution was evaporated. The residue was stirred at room temperature with 400 ml of pyridine and 200 ml of acetic anhydride for 5 hours. After concentration, the residue obtained was treated with water and acidified to pH 2–3 with 5% hydrochloric acid solution and extracted with ethyl acetate. The organic extracts were washed with ice-water and saturated sodium chloride solution, dried over magnesium sulfate and evaporated. The residue was chromatographed over silica gel with ethyl acetate. The product fractions were concentrated and the residue was crystallized from ether to give 4-(2,3,4,5,6-penta-O-acetyl-D-glucit-1-ylamino)-3-nitro-benzoic acid as yellow crystals, [a]−23.0° (c 0.5; DMSO), MS: m/z 579.7 ([M+Na]⁺).

B. 8.78 g of 2-chloro-2,4-dimethoxy-1,3,5-triazine were added to a solution of 27.8 g of 4-(2,3,4,5,6-penta-O-acetyl-D-glucit-1-ylamino)-3-nitro-benzoic acid and 5.32 g of 4-methylmorpholine in 150 ml of absolute dimethylformamide at 0°C. The reaction mixture was stirred at this temperature for 2 hours and then treated with 14.0 g of benzyl 2-amino-2-desoxy-a-D-glucopyranoside (Meyer zu Reckendorf, Chem. Ber. 107, 869 (1974)). The mixture was stirred for a further 18 hours and then concentrated in a vacuum. The residual syrup was purified by chromatography on silica gel with methylene chloride/ isopropanol and gave benzyl 2-desoxy-2-[3-nitro-4-(2,3,4,5,6-penta-O-acetyl-D-glucit-1-ylamino)-benzoylamino]-a-D-glucopyranoside, [a]+33.6° (c 0.5; DMSO), MS: m/z 808.4 ([M+H]$^+$).

C. 10.9 g of p-toluenesulfonyl chloride were added in portions to a solution of 30.0 g of benzyl 2-desoxy-2-[3-nitro-4-(2,3,4,5,6-penta-O-acetyl-D-glucit-1-ylamino)-benzoylamino]-a-D-glucopyranoside in 250 ml of absolute pyridine. After completion of the addition, the reaction mixture was stirred at room temperature for 7 hours and then concentrated. The residue was taken up in ethyl acetate and extracted with water. The organic phases were washed with dilute sulfuric acid, water and saturated sodium chloride solution, dried over magnesium sulfate and evaporated. The residue was chromatographed on silica gel with methylene chloride/isopropanol and gave benzyl 2-desoxy-2-[3-nitro-4-(2,3,4,5,6-penta-O-acetyl-D-glucit-1-ylamino)-benzoylamino]-6-O-(p-tolylsulfonyl)-a-D-gluco-pyranoside, [a]+31.4° (c 0.5; DMSO), MS: m/z 984.7 ([M+K]$^+$).

D. 6.5 g of sodium azide were added to a solution of 31.0 g of benzyl 2-desoxy-2-[3-nitro-4-(2,3,4,5,6-penta-O-acetyl-D-glucit-1-ylamino)-benzoylamino]-6-O-(p-tolylsulfonyl)-a-D-glucopyranoside in 250 ml of absolute dimethylformamide. The reaction mixture was stirred at 65° C. for 6 hours and then concentrated. The residue was poured into ice-water and extracted with ethyl acetate. The organic phases were washed with water and saturated sodium chloride solution, dried over magnesium sulfate and evaporated. The residue was chromatographed on silica gel with methylene chloride/isopropanol and gave benzyl 6-azido-2,6-didesoxy-2-[3-nitro-4-(2,3,4,5,6-penta-O-acetyl-D-glucit-1-ylamino)-benzoylamino]-a-D-glucopyranoside, [a]+30.2° (c 0.5; DMSO), MS: m/z 855.6 ([M+Na]$^+$).

E. 2.15 g of triphenylphosphine were added to a solution of 4.16 g of benzyl 6-azido-2,6-didesoxy-2-[3-nitro-4-(2,3,4,5,6-penta-O-acetyl-D-glucit-1-ylamino)-benzoylamino]-a-D-glucopyranoside in 50 ml of tetrahydrofuran and 1.8 ml of water and the mixture was stirred at room temperature for 20 hours and then concentrated. The residue was chromatographed over silica gel with ethyl acetate/methanol and gave benzyl 6-amino-2,6-didesoxy-2-[3-nitro-4-(2,3,4,5,6-penta-O-acetyl-D-glucit-1-ylamino)-benzoylamino]-a-D-glucopyranoside, [a]+37.4° (c 0.5; DMSO), MS: m/z 829.7 ([M+Na]$^+$).

F. 2-Chloro-2,4-dimethoxy-1,3,5-triazine was added to a solution of 301 mg of 1,6-bis-O-(6-carboxy-naphthalen-2-yl)-2,3:4,5-di-O-isopropylidene-galactitol (Example 16.A.) and 137 mg of N-methylmorpholine in 3 ml of absolute dimethylformamide at 0° C. The reaction mixture was stirred at this temperature for 2 hours and then treated with 1.21 g of benzyl 6-amino-2,6-didesoxy-2-[3-nitro-4-(2,3,4,5,6-penta-O-acetyl-D-glucit-1-ylamino)-benzoylamino]-a-D-glucopyranoside. The reaction mixture was stirred at room temperature for 20 hours and then concentrated. The residue was acetylated with 20 ml of acetic anhydride in 30 ml of pyridine and, after 5 hours at room temperature, concentrated. The residue was then taken up in ethyl acetate and extracted with water. The organic phases were washed with dilute sulfuric acid, water and saturated sodium bicarbonate solution, dried over magnesium sulfate and evaporated. The residue was chromatographed over silica gel with ethyl acetate/methanol and gave 1,6-bis-O-[6-[benzyl-3,4-di-O-acetyl-2,6-didesoxy-2-[3-nitro-4-(2,3,4,5,6-penta-O-acetyl-D-glucit-1-ylamino)-benzoylamino]-a-D-glucopyranosid-6-ylcarbamoyl]-naphthalen-2-yl]-2,3:4,5-di-O-isopropylidene-galactitol, [a]+43.6° (c 0.5; chloroform), MS: m/z 2370.9 ([M+Na]$^+$).

G. A solution of 1.0 g 1,6-bis-O-[6-[benzyl-3,4-di-O-acetyl-2,6-didesoxy-2-[3-nitro-4-(2,3,4,5,6-penta-O-acetyl-D-glucit 1-ylamino)-benzoylamino]-a-D-glucopyranosid-6-ylcarbamoyl]-naphthalen-2-yl]-2,3:4,5-di-O-isopropylidene-galactitol in 100 ml of 80% acetic acid was heated on a steam bath for 3 hours and then concentrated. The residue was acetylated with 20 ml of acetic anhydride in 30 ml of pyridine and, after 18 hours at room temperature, concentrated. The residue was then taken up in ethyl acetate and extracted with water. The organic phases were washed with dilute sulfuric acid, saturated sodium bicarbonate solution and saturated sodium chloride solution, dried over magnesium sulfate and evaporated. The residue was chromatographed over silica gel with methylene chloride/isopropanol and gave 2,3,4,5-tetra-O-acetyl-1,6-bis-O-[6-[benzyl-3,4-di-O-acetyl-2,6-didesoxy-2-[3-nitro-4-(2,3,4,5,6-penta-O-acetyl-D-glucit-1-ylamino)-benzoylamino]-a-D-glucopyranosid-6-ylcarbamoyl]-naphthalen-2-yl]-galactitol, [a]+44.6°(c 0.5; chloroform), MS: m/z 2358.9 ([M+Na]$^+$).

H. A solution of 820 mg of 2,3,4,5-tetra-O-acetyl-1,6-bis-O-[6-[benzyl-3,4-di-O-acetyl-2,6-didesoxy-2-[3-nitro-4-(2,3,4,5,6-penta-O-acetyl-D-glucit-1-ylamino)-benzoylamino]-a-D-glucopyranosid-6-ylcarbamoyl]-naphthalen-2-yl]-galactitol in 24 ml of methanol and 6 ml of dimethoxyethane was treated with 1 ml of a 2% methanolic sodium methanolate solution and stirred at room temperature for 6 hours. The resulting precipitate was filtered off under suction, washed with methanol and dried at 60° C. in a vacuum to give 1,6-bis-O-[6-[benzyl 2,6-didesoxy-2-(4-D-glucit-1-ylamino-3-nitro-benzoylamino)-a-D-glucopyranosid-6-ylcarbamoyl]-naphthalen-2-yl]-galactitol, [a]+33.5° (c 0.5; dimethyl sulfoxide), MS: m/z 1701.8 (M+Na)$^+$.

I. Sulfation of 1,6-bis-O-[6-[benzyl 2,6-didesoxy-2-(4-D-glucit-1-ylamino-3-nitro-benzoylamino)-a-D-glucopyranosid-6-ylcarbamoyl]-naphthalen-2-yl]-galactitol as described in Ex. 26.C. gave 1,6-bis-O-[6-[benzyl 2,6-didesoxy-2-[3-nitro-4-(2,3,4,5,6-penta-O-sulfo-D-glucit-1-ylamino)-benzoylamino]-3,4-di-O-sulfo-a-D-glucopyranosid-6-ylcarbamoyl]-naphthalen-2-yl]-2,3,4,5-tetra-O-sulfo-galactitol octadecasodium salt, [a]+43.2° (c 0.5; water), MS: m/z 3515 (reconstructed M).

EXAMPLE 60

A. Reaction of benzyl 6-amino-2,6-didesoxy-2-[3-nitro-4-(2,3,4,5,6-penta-O-acetyl-D-glucit-1-ylamino)-benzoylamino]-a-D-glucopyranoside (Example 59.E.) with 4,4'-dioxo-5,5'-(2-acetoxy-propan-1,3-diyldioxy)-di-4H-1-benzopyran-2-carboxylic acid (prepared from 4,4'-dioxo-5,5'-(2-hydroxy-propane-1 ,3-diyldioxy)-di-4H-1-benzopyran-2-carboxylic acid analogously to Example 57.C.) as described under Ex. 59.F. gave 4,4'-dioxo-5,5'-(2-acetoxy-propane-1,3-diyldioxy)-di-4H-1-benzopyran-2-carboxylic acid N,N'-bis-[benzyl 3,4-di-O-acetyl-2,6-didesoxy-2-[4-(2,3,4,5,6-penta-O-acetyl-D-glucit-1-ylamino)-3-nitro-benzoylamino]-a-D-glucopyranosid-6-yl]-amide], [a]+80.0° (c 0.5; chloroform), MS: m/z 2370.9 ([M+Na]$^+$).

B. Deacetylation of 4,4'-dioxo-5,5'-(2-acetoxy-propane-1,3-diyldioxy)-di-4H-1-benzopyran-2-carboxylic acid N,N'-bis-[benzyl 3,4-di-O-acetyl-2,6-didesoxy-2-[4-(2,3,4,5,6-penta-O-acetyl-D-glucit-1-ylamino)-3-nitro-benzoylamino]-a-D-glucopyranosid-6-yl]-amide] as described under Ex. 59.H. gave 4,4'-dioxo-5,5'-(2-hydroxy-propane-1,3-diyldioxy)-di-4H-1-benzopyran-2-carboxylic acid N,N'-bis-[[benzyl 2,6-didesoxy-2-(4-D-glucit-1-yl]-amino-3-nitro-benzoylamino)-a-D-glucopyranosid-6-yl]-amide], [a]+47.00 (c 0.5; dimethylsulfoxide), MS: m/z 1648.8 ([M+Na]+).

C. Sulfation of 4,4'-dioxo-5,5'-(2-hydroxy-propane-1,3-diyldioxy)-di-4H-1-benzopyran-2-carboxylic acid N,N'-bis-[[benzyl 2,6-didesoxy-2-(4-D-glucit-1-ylamino-3-nitro-benzoylamino)-a-D-glucopyranosid-6-yl]-amide] as described under Ex. 59.1. gave 4,4'-dioxo-5,5'-(2-sulfooxy-propane-1,3-diyldioxy)-di-4H-1-benzopyran-2-carboxylic acid N,N'-bis-[[benzyl-2,6-didesoxy-2-[4-(2,3,4,5,6-penta-O-sulfo-D-glucit-1-ylamino)-3-nitro-benzoylamino]-3,4-di-O-sulfo-a-D-glucopyranosid-6-yl] -amide] pentadecasodium salt, [a]+87.0°(c 0.2; water), MS: m/z 3156.5 (reconstructed M).

EXAMPLE 61

A. Reaction of benzyl 6-amino-2,6-didesoxy-2-[3-nitro-4-(2,3,4,5,6-penta-O-acetyl-D-glucit-1-ylamino)-benzoylamino]-a-D-glucopyranoside (Example 59.E.) with 2,3,4,5-tetra-O-acetyl-1,6-bis-O-[4-((E)-2-carboxy-vinyl)-phenyl]-galactitol (Example 57.C.) as described under Ex. 59.F. gave 2,3,4,5-tetra-O-acetyl-1,6-bis-O-[4-[(E)-2-[benzyl-3,4-di-O-acetyl-2,6-didesoxy-2-[4-(2,3,4,5,6-penta-O-acetyl-D-glucit-1-ylamino)-3-nitro-benzoylamino]-a-D-glucopyranosid-6-ylcarbamoyl]-vinyl]-phenyl]-galactitol, [a]+42.4° (c 0.5; chloroform), MS: m/z 2411.9 ([M+Na]+).

B. Deacetylation of 2,3,4,5-tetra-O-acetyl-1,6-bis-O-[4-[(E)-2-[benzyl-3,4-di-O-acetyl-2,6-didesoxy-2-[4-(2,3,4,5,6-penta-O-acetyl-D-glucit-1-ylamino)-3-nitro-benzoylamino]-a-D-glucopyranosid-6-ylcarbamoyl]-vinyl]-phenyl]-galactitol as described under Ex. 26.C. gave 1,6-bis-O-[4-[(E)-2-[benzyl 2,6-didesoxy-2-(4-D-glucit-1-ylamino-3-nitro-benzoylamino)-a-D-glucopyranosid-6-ylcarbamoyl]-vinyl]-phenyl]-galactitol, [a]+45.6° (c 0.5; dimethyl sulfoxide), MS: m/z 1654.8 ([M+Na]+).

C. Sulfation of 1,6-bis-O-[4-[(E)-2-[benzyl 2,6-didesoxy-2-(4-D-glucit-1-ylamino-3-nitro-benzoylamino)-a-D-glucopyranosid-6-ylcarbamoyl]-vinyl]-phenyl]-galactitol as described under Example 26.C. gave 1,6-bis-O-[4-[(E)-2-[benzyl 2,6-didesoxy-2-[4-(2,3,4,5,6-penta-O-sulfo-D-glucit-1-ylamino)-3-nitro-benzoyl-amino]-3,4-di-O-sulfo-a-D-glucopyranosid-6-ylcarbamoyl]-vinyl]-phenyl]-2,3,4,5-tetra-O-sulfo-galactitol octadecasodium salt, [a]+40.2° (c 0.2; water), MS: m/z 3469.0 (reconstructed M).

EXAMPLE 62

A. Reaction of benzyl 6-amino-2,6-didesoxy-2-[3-nitro-4-(2,3,4,5,6-penta-O-acetyl-D-glucit-1-ylamino)-benzoylamino]-a-D-glucopyranoside (Example 59.E.) with 1,4-bis-O-[3-carboxy-naphthalen-2-yl)-2,3-O-isopropylidene-L-threitol (Example 13.A.) as described under Ex. 59.F. gave 1,4-bis-O-[3-[benzyl-3,4-di-O-acetyl-2,6-didesoxy-2-[4-(2,3,4,5,6-penta-O-acetyl-D-glucit-1-ylamino)-3-nitro-benzoylamino]-a-D-glucopyranosid-6-ylcarbamoyl]-naphthalen-2-yl]-2,3-O-isopropylidene-L-threitol, [a]+63,4° (c 0,5; chloroform), MS: m/z 2271.0 ([M+Na]+).

B. Reaction of 1,4-bis-O-[3-[benzyl-3,4-di-O-acetyl-2,6-didesoxy-2-[4-(2,3,4,5,6-penta-O-acetyl-D-glucit-1-ylamino)-3-nitro-benzoylamino]-a-D-glucopyranosid-6-ylcarbamoyl]-naphthalen-2-yl]-2,3-O-isopropylidene-L-threitol as described under Ex. 59.G. gave 2,3-di-O-acetyl-1,4-bis-O-[3-[benzyl 3,4-di-O-acetyl-2,6-didesoxy-2-[4-(2,3,4,5,6-penta-O-acetyl-D-glucit-1-ylamino)-3-nitro-benzoylamino]-a-D-glucopyranosid-6-ylcarbamoyl]-naphthalen-2-yl]-L-threitol, [a]+62.4° (c 0.5; chloroform), MS: n/z 2315.9 ([M+Na]+).

C. Deacetylation of 2,3-di-O-acetyl-1,4-bis-O-[3-[benzyl 3,4-di-O-acetyl-2,6-didesoxy-2-[4-(2,3,4,5,6-penta-O-acetyl-D-glucit-1-ylamino)-3-nitro-benzoylamino]-a-D-glucopyranosid-6-ylcarbamoyl]-naphthalen-2-yl]-L-threitol as described under Ex. 59.H. gave 1,4-bis-O-[3-[benzyl-2,6-didesoxy-2-(4-D-glucit-1-ylamino)-3-nitro-benzoylamino)-a-D-glucopyranosid-6-yl-carbamoyl]-naphthalen-2-yl]-L-threitol, [a]+68.8° (c 0.5; dimethyl sulfoxide), MS: m/z 1642.3 ([M+Na]+).

D. Sulfation of 1,4-bis-O-[3-[benzyl 2,6-didesoxy-2-(4-D-glucit-1-ylamino)-3-nitro-benzoylamino)-a-D-glucopyranosid-6-ylcarbamoyl]-naphthalen-2-yl]-L-threitol as described under Ex. 26.C. gave 1,4-bis-O-[3-[benzyl-2,6-didesoxy-2-[4-(2,3,4,5,6-penta-O-sulfo-D-glucit-1-ylamino)-3-nitro-benzoylamino]-3,4-di-O-sulfo-a-D-glucopyranosid-6-ylcarbamoyl]-naphthalen-2-yl]-2,3-di-O-sulfo-L-threitol hexadecasodium salt, [a]+49.6° (c 0.5; water), MS: m/z 3252.5 (reconstructed M).

EXAMPLE 63

A. Reaction of benzyl 6-amino-2,6-didesoxy-2-[3-nitro-4-(2,3,4,5,6-penta-O-acetyl-D-glucit-1-ylamino)-benzoylamino]-a-D-glucopyranoside (Example 59.E.) with 1,6-bis-O-(4'-carboxy-biphenyl-4-yl)-2,3:4,5-di-O-isopropylidene-galactitol (Example 1 2.B.) as described under Ex. 59.F. gave 1,6-bis-O-[4'-[benzyl 3,4-di-O-acetyl-2,6-didesoxy-2-[3-nitro-4-(2,3,4,5,6-penta-O-acetyl-D-glucit-1-ylamino)-benzoylamino]-a-D-glucopyranosid-6-ylcarbamoyl]-biphenyl-4-yl]-2,3:4,5-di-O-isopropylidene-galactitol, MS: m/z 2422.8 ([M+Na]+).

B. Reaction of 1,6-bis-O-[4'-[benzyl 3,4-di-O-acetyl-2,6-didesoxy-2-[3-nitro-4-(2,3,4,5,6-penta-O-acetyl-D-glucit-1-ylamino)-benzoylamino]-a-D-glucopyranosid-6-ylcarbamoyl]-biphenyl-4-yl]-2,3:4,5-di-O-isopropylidene-galactitol as described under Ex. 59.G. gave 2,3,4,5-tetra-O-acetyl-1,6-bis-O-[4'-[benzyl 3,4-di-O-acetyl-2,6 -didesoxy-2-[3-nitro-4-(2,3,4, 5,6-penta-O-actyl-D-glucit-1-ylamino)-benzoylamino]-a-D-glucopyranosid-6-ylcarbamoyl]-biphenyl-4-yl]-galactitol, [a]+49.8° (c 0.5; chloroform), MS: m/z 2510.8 ([M+Na]+).

C. Deacetylation of 2,3,4,5-tetra-O-acetyl-1,6-bis-O-[4'-[benzyl-3,4-di-O-acetyl-2,6-didesoxy-2-[3-nitro-4-(2,3,4,5,6-penta-O-acetyl-D-glucit-1-ylamino)-benzoylamino]-a-D-glucopyranosid-6-ylcarbamoyl]-biphenyl-4-yl]-galactitol as described under Ex. 59.H. gave 1,6-bis-O-[4'-[benzyl-2,6-didesoxy-2-(4-D-glucit-1-ylamino-3-nitro-benzoylamino)-a-D-glucopyranosid-6-ylcarbamoyl]-biphenyl-4-yl]-galactitol, [a]+32.0° (c 0.5; dimethyl sulfoxide).

D. Sulfation of 1,6-bis-O-[4'-[benzyl 2,6-didesoxy-2-(4-D-glucit-1-ylamino-3-nitro-benzoylamino)-a-D-glucopyranosid-6-ylcarbamoyl]-biphenyl-4-yl]-galactitol as described under Ex. 26.C. gave 1,6-bis-O-[4'-[benzyl 2,6-didesoxy-2-[3-nitro-4-(2,3,4,5,6-penta-O-sulfo-D-glucit-1-ylamino)-benzoylamino]-3,4-di-O-sulfo-a-D- glucopyranosid-6-ylcarbamoyl]-biphenyl-4-yl]-2,3,4,5-tetra-O-sulfo-galactitol octadecasodium salt, [α]+41.5° (c 0.5; water), MS: m/z 3269.0 (reconstructed M).

EXAMPLE 64

A. 13.80 g of 4-hydroxy-benzoic acid and 45.20 g of tert.-butyl-dimethylchlorosilane were stirred at room temperature under argon for 18 hours with the addition of 40.80 g of imidazole in 500 ml of dimethylformamide. The solvent was distilled off in a water-jet vacuum and the residue was worked up extractively with ice-water and methylene chloride. The thus-obtained crude product was chromatographed on silica gel with methylene chloride and acetonitrile. There was thus obtained 4-(tert.-butyl-dimethylsilanyloxy)-benzoic acid, elementary analysis calculated for $C_{13}H_{20}O_3Si$: C=61.87%, H=7.99%; found: C=61.71%, H=8.00%.

B. 15.60 g of Fmoc-2,4-dimethoxy-4'-(carboxymethyloxy)-benzohydrylamine bonded to an aminomethyl-polystyrene resin (0.55 mmol/g, Bachem AG, Bubendorf, Switzerland; No D-1675) was stirred at room temperature for 30 minutes with 20 ml of piperidine in 80 ml of dimethylformamide and then filtered. The resin was washed twice with 20 ml of dimethylformamide each time and dried in a high vacuum for 15 minutes. The thus-obtained resin was suspended in 80 ml of dimethylformamide, 4.42 g of 4-(tert.-butyl-dimethylsilanyloxy)-benzoic acid, 5.20 g of 2-(2-oxo-2H-pyridin-1-yl)-1,1,3,3-tetramethyl-uronium tetrafluoroborate and 7.53 ml of ethyl-diisopropyl-amine were added and the mixture was stirred at room temperature for 1 hour; after filtration of the reaction mixture the resin was washed in succession with water, isopropanol and methylene chloride and dried at 40° C. in a water-jet vacuum for 18 hours.

C. 14.50 g of resin from paragraph B. were treated in 50 ml of tetrahydrofuran with 50 ml of tetrabutyl-ammonium fluoride solution (1 molar in tetrahydrofuran) and stirred at room temperature for 1 hour. After filtration and washing with tetrahydrofuran, the resin was dried at 40° C. in a water-jet vacuum for 6 hours.

D. 28.40 g of the resin from paragraph C. and 47.00 g of 2,3-O-isopropylidene-1,4-di-O-(4-methyl-phenylsulfonyl)-L-threitol were stirred at 100° C. for 6 hours with the addition of 34.80 g of potassium carbonate in 100 ml of dimethylformamide. After cooling to room temperature, the mixture was filtered and the residue was washed in succession with water, isopropanol and methylene chloride and dried at 40° C. in a water-jet vacuum for 18 hours.

E. 23.00 g of the resin from paragraph D. and 24.65 g of bis-(4-hydroxy-phenyl)-methane were stirred at 100° C. for 6 hours with the addition of 34.80 g of potassium carbonate in 100 ml of dimethylformamide and worked up analogously to Example 64.D.

F. 22.00 g of the resin from paragraph E. were reacted and worked up analogously to Example 64.D.

G. 23.40 g of the resin from paragraph F. were reacted and worked up analogously to Example 64.E.

H. 22.85 g of the resin from paragraph G. were reacted at 140° C. for 6 hours with 32.93 g of (R)-2,2-dimethyl-[1,3]dioxolan-4-ylmethyl toluene-4-sulfonate with the addition of 33.40 g of potassium carbonate in 100 ml of dimethylformamide and worked up analogously to Example 64.D.

I. 24.60 g of the resin from paragraph H. were stirred at room temperature in 250 ml of 95 per cent aqueous trifluoroacetic acid for 1 hour; thereafter the mixture was filtered and the filtrate was concentrated. The thus-obtained residue was dissolved in 75 ml of pyridine with 25 ml of acetic anhydride and stirred at room temperature for 16 hours. Thereupon, the reaction mixture was worked up extractively with ice-water and methylene chloride and the crude product was chromatographed on silica gel with methylene chloride and methanol. There was thus obtained (S)-2,2',3,3'-tetra-O-acetyl-4-O-[4-[4-(2,3-bis-acetoxy-propoxy)-benzyl]-phenyl]-4'-O-(4-carbamoyl-phenyl)-1,1'-(4,4'-methylene-diphenylene)-di-L-threitol, MS: m/z 1058.8 ([M+Na]⁺).

K 1.50 g of (S)-2,2',3,3'-tetra-O-acetyl-4-O-[4-[4-(2,3-bis-acetoxy-propoxy)-benzyl]-phenyl]-4'-O-(4-carbamoyl-phenyl)-1,1'-(4,4'-methylene-diphenylene)-di-L-threitol in 50 ml of methanol were treated with I ml of sodium methylate solution (5.4 molar in methanol) and stirred at room temperature for 22 hours. The reaction mixture was adjusted to pH 4–5 with hydrochloric acid and concentrated. The thus-obtained (R)-4'-O-(4-carbamoyl-phenyl)-4-O-[4-[4-(2,3-dihydroxy-propoxy)-benzyl]-phenyl]-1,1'-(4,4'-methylene-diphenylene)-di-L-threitol was dried over phosphorus pentoxide at room temperature in a high vacuum for 4 hours and was used directly in the next step.

L. 1.00 g of (R)-4'-O-(4-carbamoyl-phenyl)-4-O-[4-[4-(2,3-dihydroxy-propoxy)-benzyl]-phenyl]-1,1'-(4,4'-methylene-diphenylene)-di-L-threitol were reacted with sulfur trioxide-trimethylamine complex in analogy to Example 1.B. There was thus obtained (S)-4-O-[4-[4-(2,3-bis-sulfooxy-propoxy)-benzyl]-phenyl]-4'-O-(4-carbamoyl-phenyl)-2,2',3,3'-tetra-O-sulfo-1,1'-(4,4'-methylene-diphenylene)-di-L-threitol hexasodium salt, MS: m/z 1396.0 (reconstructed M).

Example A

| Tablets: | | |
|---|---|---|
| 1 | Compound of formula Ia or Ib | 500 mg |
| 2 | Anhydrous lactose | 150 mg |
| 3 | Microcrystalline cellulose | 150 mg |
| 4 | Polyvinylpyrrolidone | 40 mg |
| 5 | Talc | 50 mg |
| 6 | Magnesium stearate | 10 mg |
| | Tablet weight | 900 mg |

Ingredients 1–4 are sieved and mixed. This mixture is granulated with demineralized water and the dried granulate is mixed with ingredients 5 and 6. The mixture is pressed to tablets of suitable form.

Example B

| Pellets: | | |
|---|---|---|
| 1 | Compound of formula Ia or Ib | 500 mg |
| 2 | Microcrystalline cellulose | 200 mg |
| 3 | PRIMOJEL | 70 mg |
| 4 | Flavour powder | 10 mg |
| 5 | Talc | 20 mg |

Mixed and sieved ingredients 1–3 are moistened sufficiently with demineralized water and pressed by means of an extruder through a suitable perforated disc. The extrudate is transferred to a pelleting plate, rounded-off to beadlets and subsequently dried. The mixture is treated with sieved ingredients 4 and 5 and filled into paper sachets (or similar).

EXAMPLE C

Injection solution

For the production of an injection solution, 50 mg of compound of formula I as well as 0.5 mg of Tris buffer are dissolved in water for injection ad 1 ml and the pH value is adjusted to 7.4. The solution is filtered sterile and, after filling into ampules, autoclaved.

We claim:

1. A compound of formula $$(A^1-X^1)_m{}^1-(Y^1-X^2-)_n{}^1-(Q^1-X^3-)_m{}^2-(Y^2-X^4)_n{}^2-(-Z^1-X^5-)_m{}^3-(Y^3-X^6)_n{}^3 \quad \text{Ia}$$
$$|$$
$$D$$
$$|$$
$$(A^2-X^7)_m{}^4-(Y^4-X^8-)_n{}^4-(Q^2-X^9-)_m{}^5-(Y^5-X^{10})_n{}^5-(-Z^2-X^{11}-)_m{}^6-(Y^6-X^{12})_n{}^6$$

or $$(A^1-X^1)_m{}^1-(Y^1-X^2-)_n{}^1-(Q^1-X^3-)_m{}^2-(Y^2-X^4)_n{}^2-(-Z^1-X^5-)_m{}^3-(Y^3-X^6)_n{}^3 \quad \text{Ib}$$
$$|$$
$$(A^2-X^7)_m{}^4-(Y^4-X^8-)_n{}^4-(Q^2-X^9-)_m{}^5-(Y^5-X^{10})_n{}^5-(-Z^2-X^{11}-)_m{}^6-(Y^6-X^{12})_n{}^6-W$$
$$|$$
$$(A^3-X^{13})_m{}^7-(Y^7-X^{14}-)_n{}^7-(Q^3-X^{15}-)_m{}^8-(Y^8-X^{16})_n{}^8-(-Z^3-X^{17}-)_m{}^9-(Y^9-X^{18})_n{}^9$$

wherein $n^1-n^9$ are each independently 0 or 1;

$m^1-m^9$ are each independently 0 or 1, but with the proviso that at least one of $m^1$, $m^2$ and $m^3$, at least one of $m^4$, $m^5$ and $m^6$ and, at least one of $m^7$, $m^8$ and $m^9$ is 1; and wherein $X^1-X^{18}$ each independently is —O—, —CONR$^1$—,—NR$^1$CO— or —NR$^1$—;

$R^1$ is hydrogen or lower alkyl;

W is a benzene or s-triazine;

$Y^1-Y^9$ each independently is an aromatic ring system;

$A^1-A^3$ each independently is a residue of a sugar alcohol devoid of the 1-hydroxy group or a derivative thereof, a residue of a sugar acid devoid of the 1-carboxy group or a derivative thereof or tris-(hydroxymethyl)-methyl;

D is the di-residue of a sugar alcohol devoid of 2 hydroxy groups or a derivative thereof or the di-residue of a sugar dicarboxylic acid devoid of 2 carboxy group or a derivative thereof;

$Q^1-Q^3$ and $Z^1-Z^3$ each independently are the di-residue of a sugar alcohol devoid of 2 hydroxy groups or a derivative thereof or the di-residue of a sugar dicarboxylic acid devoid of 2 carboxy groups or a derivative thereof or didesoxyglycopyranoside or a derivative thereof, wherein at least one hydroxy group of residues $A^1-A^3$, D, $Q^1-Q^3$ and $Z^1-Z^3$ is esterified with sulfuric acid with the proviso that a carbon atom which is not present in a ring system and which is bonded to hydroxy or hydroxy esterified with sulfuric acid is not bonded to another hetero atom, or pharmaceutically acceptable salts thereof.

2. A compound in accordance with claim 1, wherein each of $Y^1-Y^9$ are a)

b)

c)

d)

e)

f)

g)

h)

wherein $R^2$ is hydrogen, halogen, nitro, lower alkyl, lower alkoxy, lower aralkoxy, carbamoyl or glycerol, wherein the hydroxy groups present are sulfated or nonsulfated, $G^1$ and $G^2$ are lower alkylene, lower alkenylene, lower alkynylene or lower alkyleneoxy;

E is a carbon-carbon bond; —O—, —CO—, —CH$_2$—, —CH$_2$—CH$_2$—,—CH=CH—, —C≡C—, —NR$^3$—CO— or —CO—NR$^3$—; and $R^3$ is hydrogen or lower alkyl.

3. A compound in accordance with claim 1, wherein in formula Ia,
$(A^1-X^1)_m{}^1-(Y^1-X^2-)_n{}^{1-(Q^1}-X^3-)_m{}^2-(Y^2-X^4)_n{}^2-(-Z^1-X^5-)_m{}^3-(Y^3-X^6)_n{}^3$ is the same as
$(A^2-X^7)_m{}^4-(Y^4-X^8-)_n{}^4-(Q^2-X^9-)_m{}^5-(Y^5-X^{10})_n{}^5-(-Z^2-X^{11}-)_m{}^6-(Y^6-X^{12})_n{}^6$; and in formula Ib,
$(A_1-X^1)_m{}^1-(Y^1-X^2-)_n{}^1-(Q^1-X^3-)_m{}^2-(Y^2-X^4)_n{}^2-(Z^1-X^5-)_m{}^3-(Y^3-X^6)_n{}^3$;

$(A^2-X^7)_m{}^4-(Y^4-X^8-)_n{}^4-(Q^2-X^9-)_m{}^5-(Y^5-X^{10})_n{}^5-(-Z^2-X^{11}-)_m{}^6-(Y^6-X^{12})_n{}^6$; and
$(A^3-X^{13})_m{}^7-(Y^7-X^{14}-)_n{}^7-(Q^3-X^{15}-)_m{}^8-(Y^8-X^{16})_n{}^8-(Y^8-X^{16})_n{}^8-(-Z^3-X^{17}-)_m{}^9-(Y^9-X^{18})_n{}^9$ are the same.

4. A compound in accordance claim 1, wherein $m^2$, $m^3$, $m^5$, $m^6$, $m^8$, $m^9$ and $n^2$, $n^3$, $n^5$, $n^6$, $n^8$, $n^9$ in formula Ib are 0.

5. A compound in accordance with claim 3, wherein $m^2$, $m^3$, $m^5$, $m^6$, $m^8$, $m^9$ and $n^2$, $n^3$, $n^5$, $n^6$, $n^8$, $n^9$ in formula Ib are 0.

6. A compound in accordance with claim 1, wherein $A^1–A^3$, D, $Q^1–Q^3$, $Z^1–Z^3$ are derived from a hexitol, a pentitol, a tetritol, glycerol or tris-(hydroxymethyl)-methane.

7. A compound in accordance with claim 6, wherein $A^1–A^3$, D, $Q^1–Q^3$, $Z^1–Z^3$ are glucitol, galactitol, mannitol, gulitol, arabinitol, ribitol, xylitol, threitol, erythritol, glycerol, or tris-(hydroxymethyl)methane.

8. A compound in accordance with claim 1, wherein $A^1–A^3$ are derived from ribonic acid, gluconic acid or gulonic acid.

9. A compound in accordance with claim 3, wherein $A^1–A^3$ are derived from ribonic acid, gluconic acid or gulonic acid.

10. A compound in accordance with claim 1, wherein D, $Q^1–Q^3$, $Z^1–Z^3$ are derived from tartaric acid, galactaric acid or glucaric acid.

11. A compound in accordance with claim 1, wherein $Q^1–Q^3$, $Z^1–Z^3$ are derived from a glycopyranoside.

12. A compound in accordance with claim 1, which is 1,6-Bis-O-[4-[2-(2,3,4,5,6-penta-O-sulfo-D-glucit-1-ylcarbamoyl)-ethyl]-phenyl]-2,3,4,5-tetra-O-sulfo-galactitol.

13. A compound in accordance with claim 1, which is 1,6-bis-O-[4-[2-[4-(2,3,4,5,6-penta-O-sulfo-D-glucit-1-ylcarbamoyl)-phenyl]-ethyl]-phenyl]-2,3,4,5-tetra-O-sulfo-galactitol.

14. A compound in accordance with claim 1, which is 1,6-bis-O-[3-(2,3,4,5,6-penta-O-sulfo-D-glucit-1-ylcarbamoyl)-naphthalen-2-yl]-2,3,4,5-tetra-O-sulfo-galactitol.

15. A compound in accordance with claim 1, which is 1,6-bis-O-[6-(2,3,4,5,6-penta-O-sulfo-D-glucit-1-ylcarbamoyl)-naphthalen-2-yl]-2,3,4,5-tetra-O-sulfo-galactitol.

16. A compound in accordance with claim 1, which is 1,6-bis-O-[3-biphenyl-4-ylmethoxy-5-(2,3,4,5,6-penta-O-sulfo-D-glucit-1-ylcarbamoyl)-phenyl]-2,3,4,5-tetra-O-sulfo-galactitol.

17. A compound in accordance with claim 1, which is 1,6-bis-O-[6-[(S)-2,3-bis-sulfooxy-propoxy]-3-(2,3,4,5,6-penta-O-sulfo-D-glucit-1-ylcarbamoyl)-naphthalen-2-yl]-2,3,4,5-tetra-O-sulfo-galactitol.

18. A compound in accordance with claim 1, which is 1,6-bis-O-[3-(2,3,4,5-tetra-O-sulfo-D-arabinit-1-yloxy)-naphthalen-2-yl]-2,3,4,5-tetra-O-sulfo-galactitol.

19. A compound in accordance with claim 1, which is 2,3,4,5-tetra-O-sulfo-1,6-bis-O-[4-[4-(2,3,4,5-tetra-O-sulfo-D-arabinit-1-yloxy)-benzyl]-phenyl]-D-mannitol.

20. A compound in accordance with claim 1, which is 1,6-didesoxy-2,3,4,5-tetra-O-sulfo-1,6-bis-[3-(2,3,4,5-tetra-O-sulfo-D-arabinit-1-yloxy)-naphthalen-2-ylcarbonylamino]-galactitol.

21. A compound in accordance with claim 1, which is 1,6-bis-O-[4-[4-O-[4-[(E)-2-(2,3,4,5,6-penta-O-sulfo-D-glucit-1-ylcarbamoyl)-vinyl]-phenyl]-2,3-di-O-sulfo-D-threit-1-yloxy]-phenyl]-2,3,4,5-tetra-O-sulfo-galactitol.

22. A compound in accordance with claim 1, which is 1,6-bis-O-[4-[4-O-[4-[(E)-2-[methyl-(2,3,4,5,6-penta-O-sulfo-D-glucit-1-yl)-carbamoyl]-vinyl]-phenyl]-2,3-di-O-sulfo-D-threit-1-yloxy]-phenyl]-2,3,4,5-tetra-O-sulfo-galactitol.

23. A compound in accordance with claim 1, which is 1,6-bis-O-[3-[benzyl 2,6-didesoxy-6-(2,3,4,5,6-penta-O-sulfo-D-gluconoyl-amino)-3,4-di-O-sulfo-a-D-glucopyranosid-2-ylcarbamoyl]-naphthalen-1-yl]-2,3,4,5-tetra-O-sulfo-galactitol.

24. A compound in accordance with claim 1, which is 1,6-bis-O-[4-[2-[benzyl 2,6-didesoxy-6-(2,3,4,5,6-penta-O-sulfo-D-gluconoylamino)-3,4-di-O-sulfo-a-D-glucopyranosid-2-ylcarbamoyl]-ethyl]-phenyl]-2,3,4,5-tetra-O-sulfo-galactitol.

25. A compound in accordance with claim 1, which is 1,6-bis-O-[6-[benzyl 2,6-didesoxy-2-[3-nitro-4-(2,3,4,5,6-penta-O-sulfo-D-glucit-1-ylamino)-benzoylamino]-3,4-di-O-sulfo-a-D-glucopyranosid-6-ylcarbamoyl]-naphthalen-2-yl]-2,3,4,5-tetra-O-sulfo-galactitol.

26. A compound in accordance with claim 1, which is 1,6-bis-O-[4-[(E)-2-[benzyl 2,6-didesoxy-2-[4-(2,3,4,5,6-penta-O-sulfo-D-glucit-1-ylamino)-3-nitro-benzoylamino]-3,4-di-O-sulfo-a-D-glucopyranosid-6-ylcarbamoyl]-vinyl]-phenyl]-2,3,4,5-tetra-O-sulfo-galactitol.

27. A pharmaceutical composition comprising an effective amount of a compound of the formula $$(A^1-X^1)_m{}^1-(Y^1-X^2-)_n{}^1-(Q^1-X^3-)_m{}^2-(Y^2-X^4)_n{}^2-(-Z^1-X^5-)_m{}^3-(Y^3-X^6)_n{}^3 \quad \text{Ia}$$
$$|$$
$$D$$
$$|$$
$$(A^2-X^7)_m{}^4-(Y^4-X^8-)_n{}^4-(Q^2-X^9-)_m{}^5-(Y^5-X^{10})_n{}^5-(-Z^2-X^{11}-)_m{}^6-(Y^6-X^{12})_n{}^6$$

or $$(A^1-X^1)_m{}^1-(Y^1-X^2-)_n{}^1-(Q^1-X^3-)_m{}^2-(Y^2-X^4)_n{}^2-(-Z^1-X^5-)_m{}^3-(Y^3-X^6)_n{}^3 \quad \text{Ib}$$
$$|$$
$$(A^2-X^7)_m{}^4-(Y^4-X^8-)_n{}^4-(Q^2-X^9-)_m{}^5-(Y^5-X^{10})_n{}^5-(-Z^2-X^{11}-)_m{}^6-(Y^6-X^{12})_n{}^6-W$$
$$|$$
$$(A^3-X^{13})_m{}^7-(Y^7-X^{14}-)_n{}^7-(Q^3-X^{15}-)_m{}^8-(Y^8-X^{16})_n{}^8-(-Z^3-X^{17}-)_m{}^9-(Y^9-X^{18})_n{}^9$$

wherein $n^1–n^9$ are each independently 0 or 1;

$m^1–m^9$ are each independently 0 or 1, but with the proviso that at least one of $m^1$, $m^2$ and $m^3$, at least one of $m^4$, $m^5$ and $m^6$ and, at least one of $m^7$, $m^8$ and $m^9$ is 1; and wherein $X^1–X^{18}$ each independently is —O—, —CONR$^1$—,—NR$^1$CO— or —NR$^1$—;

$R^1$ is hydrogen or lower alkyl;

W is benzene or s-triazine;

$Y^1–Y^9$ each independently is an aromatic ring system;

$A^1–A^3$ each independently is a residue of a sugar alcohol devoid of the 1-hydroxy group or a derivative thereof, a residue of a sugar acid devoid of the 1-carboxy group or a derivative thereof or tris-(hydroxymethyl)-methyl;

D is the di-residue of a sugar alcohol devoid of 2 hydroxy groups or a derivative thereof or the di-residue of a sugar dicarboxylic acid devoid of 2 carboxy group or a derivative thereof;

$Q^1–Q^3$ and $Z^1–Z^3$ each independently is the di-residue of a sugar alcohol devoid of 2 hydroxy groups or a derivative thereof or the di-residue of a sugar dicarboxylic acid devoid of 2 carboxy groups or a derivative thereof or didesoxyglycopyranoside or a derivative thereof, wherein at least one hydroxy group of residues $A^1$–$A^3$, D, $Q^1$–$Q^3$ and $Z^1$–$Z^3$ is esterified with sulfuric acid with the proviso that a carbon atom which is not present in a ring system and which is bonded to hydroxy or hydroxy esterified with sulfuric acid is not bonded to another hetero atom, and pharmaceutically acceptable salts thereof and an inert carrier.

* * * * *

UNITED STATES PATENT AND TRADEMARK OFFICE
CERTIFICATE OF CORRECTION

PATENT NO. : 5,830,920
DATED : November 3, 1998
INVENTOR(S) : Alexander Chucholowski, et al.

It is certified that error appears in the above-identified patent and that said Letters Patent is hereby corrected as shown below:

On the title page, Item [57] Abstract:

Formula Ib, replace line 6 with -- $(A^2-X^7)_m{}^4-(Y^4-X^8-)_n{}^4-(Q^2-X^9-)_m{}^5-(Y^5-X^{10})_n{}^5-(-Z^2-X^{11}-)_m{}^6-(Y^6-X^{12})_n{}^6-W$ --.

<u>In the Claims</u>

Claim 1, column 77, formula Ib, replace line 19 with -- $(A^2-X^7)_m{}^4-(Y^4-X^8-)_n{}^4-(Q^2-X^9-)_m{}^5-(Y^5-X^{10})_n{}^5-(-Z^2-X^{11}-)_m{}^6-(Y^6-X^{12})_n{}^6-W$ --.

Claim 3, column 78, replace line 62 with -- $(A^1-X^1)_m{}^1-(Y^1-X^2-)_n{}^1-(Q^1-X^3-)_m{}^2-(Y^2-X^4)_n{}^2-$ --.

Claim 3, column 78, replace lines 66-67 with -- $(A^1-X^1)_m{}^1-(Y^1-X^2-)_n{}^1-(Q^1-X^3-)_m{}^2-(Y^2-X^4)_n{}^2-(-Z^1-X^5-)_m{}^3-(Y^3-X^6)_n{}^3;$ --.

UNITED STATES PATENT AND TRADEMARK OFFICE
CERTIFICATE OF CORRECTION

PATENT NO. : 5,830,920
DATED : November 3, 1998
INVENTOR(S) : Alexander Chucholowski et al.

It is certified that error appears in the above-identified patent and that said Letters Patent is hereby corrected as shown below:

Claim 3, column 79, replace lines 3-4 with -- $(A^3-X^{13})_m 7-(Y^7-X^{14}-)_n 7-(Q^3-X^{15}-)_m 8-(Y^8-X^{16})_n 8-(-Z^3-X^{17}-)_m 9-(Y^9-X^{18})_n 9$ are the same. --.

Claim 27, column 80, formula Ib, replace line 44 with -- $(A^2-X^7)_m{}^4-(Y^4-X^8-)_n{}^4-(Q^2-X^9-)_m{}^5-(Y^5-X^{10})_n{}^5-(-Z^2-X^{11}-)_m{}^6-(Y^6-X^{12})_n{}^6-W$ --.

Signed and Sealed this

Thirteenth Day of July, 1999

Attest:

Attesting Officer

Q. TODD DICKINSON

Acting Commissioner of Patents and Trademarks